US009512180B2

(12) United States Patent
Morikis et al.

(10) Patent No.: US 9,512,180 B2
(45) Date of Patent: Dec. 6, 2016

(54) COMPSTATIN ANALOGS

(71) Applicants: THE REGENTS OF THE UNIVERSITY OF CALIFORNIA, Oakland, CA (US); THE TRUSTEES OF PRINCETON UNIVERSITY, Princeton, NJ (US); UNIVERSITY OF CYPRUS, Cyprus (GR)

(72) Inventors: Dimitrios Morikis, Riverside, CA (US); Ronald D. Gorham, Riverside, CA (US); Christodoulos A. Floudas, Princeton, NJ (US); Meghan L. Bellows-Peterson, Livermore, CA (US); George A. Khoury, Schnecksville, PA (US); Georgios Archontis, Cyprus (GR); Phanourios Tamamis, Cyprus (GR)

(73) Assignees: The Regents of the University of California, Oakland, CA (US); The Trustees of Princeton University, Princeton, NJ (US); University of Cyprus, Cyprus (GR)

( * ) Notice: Subject to any disclaimer, the term of this patent is extended or adjusted under 35 U.S.C. 154(b) by 0 days.

(21) Appl. No.: 14/652,076

(22) PCT Filed: Dec. 19, 2013

(86) PCT No.: PCT/US2013/076543
§ 371 (c)(1),
(2) Date: Jun. 12, 2015

(87) PCT Pub. No.: WO2014/100407
PCT Pub. Date: Jun. 26, 2014

(65) Prior Publication Data
US 2015/0329594 A1 Nov. 19, 2015

Related U.S. Application Data

(60) Provisional application No. 61/739,438, filed on Dec. 19, 2012.

(51) Int. Cl.
*C07K 7/08* (2006.01)
*C07K 14/47* (2006.01)
*A61K 38/00* (2006.01)

(52) U.S. Cl.
CPC .............. *C07K 7/08* (2013.01); *C07K 14/472* (2013.01); *A61K 38/00* (2013.01)

(58) Field of Classification Search
None
See application file for complete search history.

(56) References Cited

U.S. PATENT DOCUMENTS

2011/0044983 A1  2/2011  Lambris et al.
2012/0004393 A1  1/2012  Lambris et al.

FOREIGN PATENT DOCUMENTS

WO    2012/040259 A2    3/2012

OTHER PUBLICATIONS

Tamamis et al. Chem Biol and Drug Design, vol. 73, No. 5, pp. 703-718, Feb. 2012.*
Nickitas-Etiene, Athina, International Preliminary Report on Patentability and Written Opinion, PCT/US2013/076543, The International Bureau of WIPO, Jul. 2, 2015.
Gorham Jr. et al., "Novel compstatin family peptides inhibit complement activation by drusen-like deposits in human retinal pigmented epithelial cell cultures," Exp. Eye Res., vol. 116, pp. 96-108, Aug. 15, 2013.
Qu et al., "New analogs of the clinical complement inhibitor compstatin with subnanomolar affinity and enhanced pharmacokinetic properties," Immunogiol., vol. 218, No. 4, pp. 496-505, Jun. 17, 2012.
Tamamis et al., "Molecular dynamics in drug design: new generations of compstatin analogs," Chem. Biol. and Drug Design, vol. 73, No. 5, pp. 703-718, Feb. 9, 2012.
Kim, Seung Beom, International Search Report and Written Opinion, PCT/US2013/076543, Korean Intellectual Property Office, Apr. 1, 2014.
Gorham Jr. et al., "Novel Compstatin Family Peptides Prevent Complement-associated Deposit Formation in Human Retinal Pigmented Epithelial Cell Cultures", Experimental Eye Research 116:96-108, Aug. 15, 2013.
Gorham Jr. et al., "New Compstatin Peptides Containing N-Terminal Extensions and Non-Natural Amino Acids Exhibit Potent Complement Inhibition and Improved Solubility Characteristics" J. Med. Chem. 58(2):814-826, epub. Dec. 10, 2014.

* cited by examiner

*Primary Examiner* — Amber D Steele
*Assistant Examiner* — Schuyler Milton
(74) *Attorney, Agent, or Firm* — Joseph R. Baker, Jr.; Gavrilovich, Dodd & Lindsey LLP

(57) ABSTRACT

The disclosure describes compstatin analogs and methods of using such analogs for the treatment of complement-related disease and disorder.

15 Claims, 42 Drawing Sheets

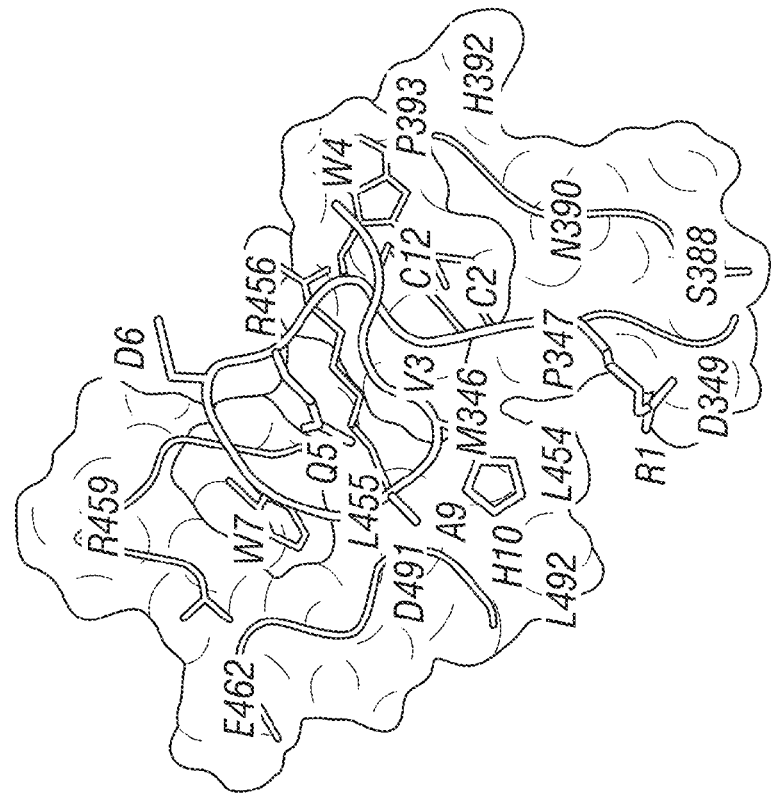
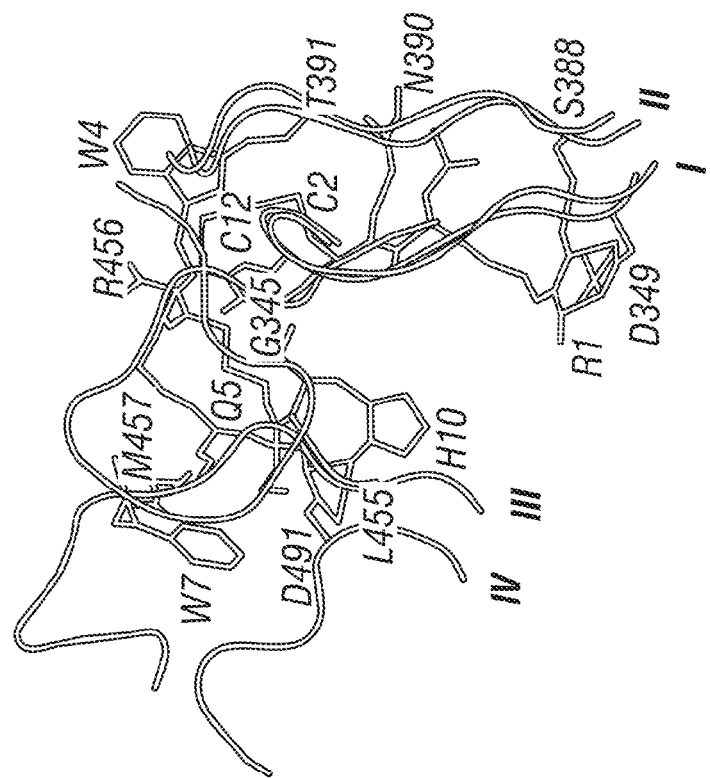
FIG. 1B
FIG. 1A

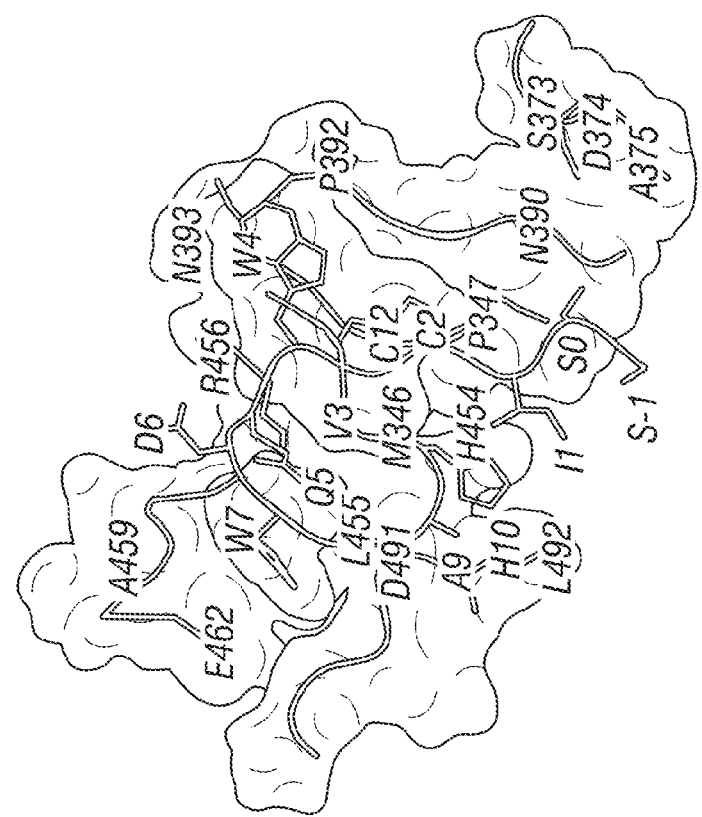
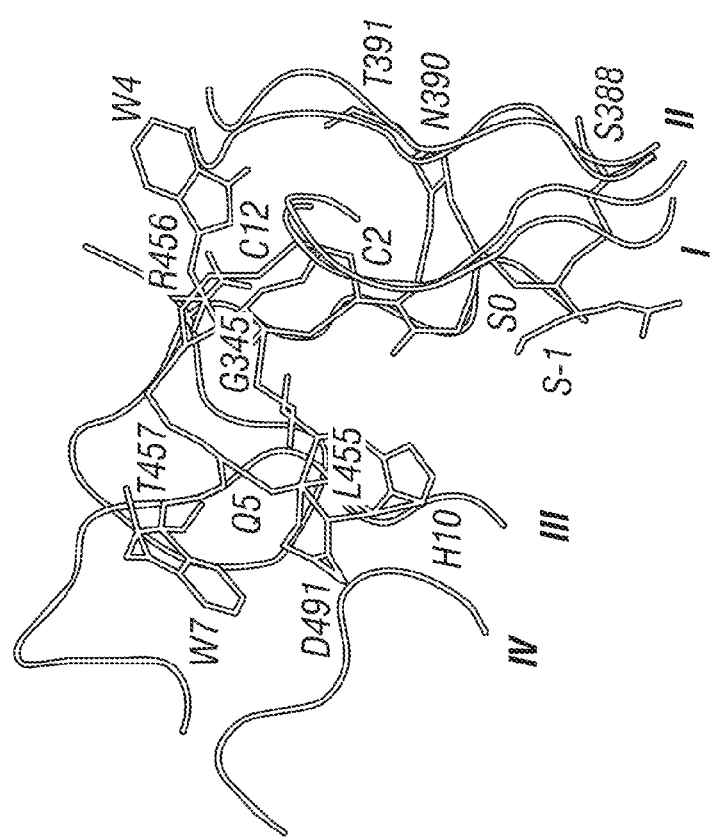
FIG. 1F
FIG. 1E

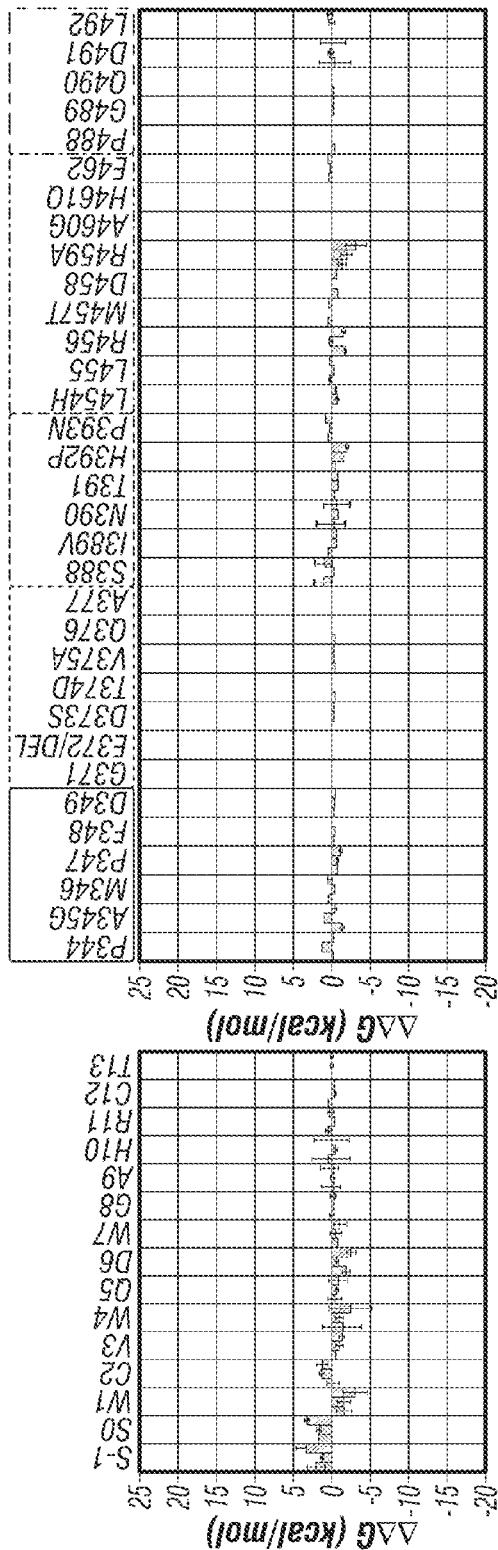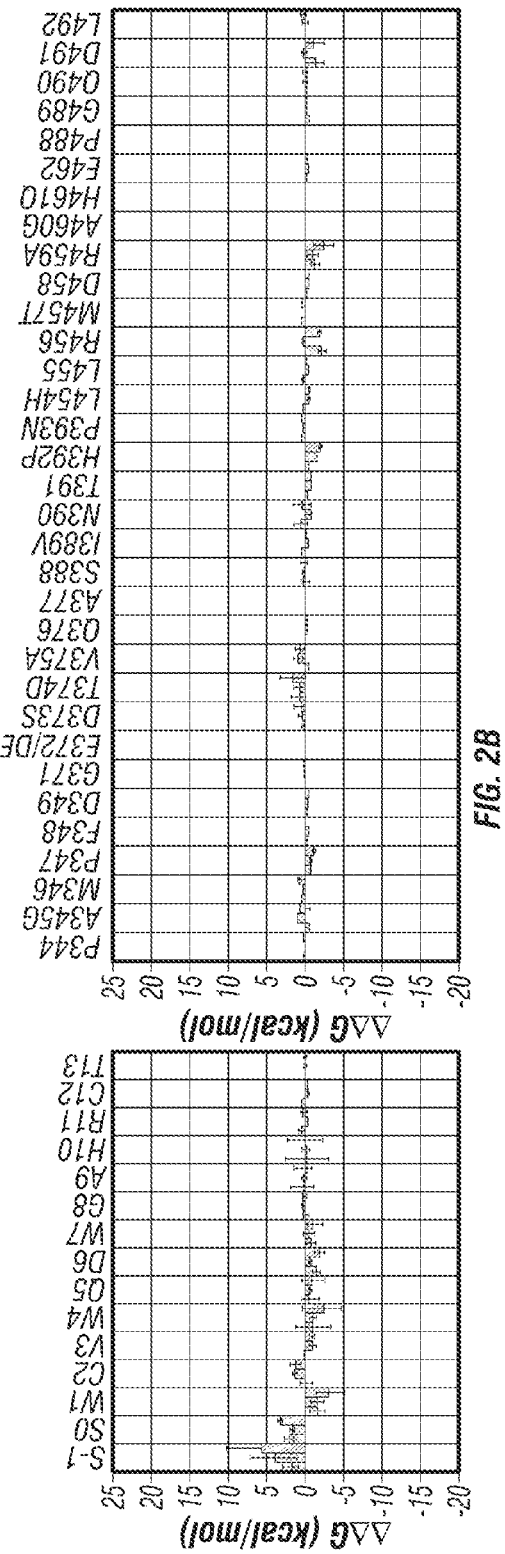
FIG. 2A
FIG. 2B

```
                          330       340       350       360       370       380
Homo sapiens              SPYQIHFTKTPKYFK PGMPFD LMVFVTNPDGSPAYRVPVAVQ GEDTVQ SLTQGDGVAHLS
Rattus norvegicus         SPYQIHFTKTPKFFN PAMPFD LMVFVTNPDGSPARRVFVVTQ -SDAQA LTQDDGVAHLS
Mus musculus              SPYQIHFTKTPKFFN PAMPFD LMVFVTNPDGSPASKVLVVTQ -SNAKA LTQDDGVAHLS
                          ***************  *****  **************   *   :.   :.*** **** *:*

390       400       410       420       430       440
Homo sapiens              INTF PSQKPLSITVSTKKQELSEAEQATRTMQALPYSTVGRSNRYLRLSVLFTELRPGET
Rattus norvegicus         VNTF NNEQPLTITVSTKKEGIPDARQATRTMQAQPYSTMHRSNRYLRLSVSFVELKPGDN
Mus musculus              INTF NSEQPLTITVSTKEDTLPESRQATRTMEAHPYSTMHRSNRYLRLSVSPMELKPGDN
                          :**  .:..* :**  *.* :*   :  ***.**::   *** .** ****** *  **  **:.

450       460       470       480       490       500
Homo sapiens              LNVHF LLKMDRAH EAKIFYYTYLIMNEGPLLKAGRQVFE PGQDL VVLPLSITTDFIPSFP
Rattus norvegicus         LNVHF HLKTDAGQ EAKIFYYTYLVMNEGKLLKAGRQVFE PGQDL VVLSLFITPEFIPSFP
Mus musculus              LNVHF HLKTDPGH EAKIFYYTYLVMNEGKLLKAGRQVFE PGQDL VVLSLFITPEFIPSFP
                          :****  **   *    :********:****:**********     ****** :**:*:*****

510       520       530
Homo sapiens              LVAYYTLIGASGQRE VVADSWWDVK
Rattus norvegicus         LVAYYTLIGANGQRE VVADSWWDVK
Mus musculus              LVAYYTLIGASGQRE VVADSWWDVK
                          **********:****  *********
```

FIGURE 4

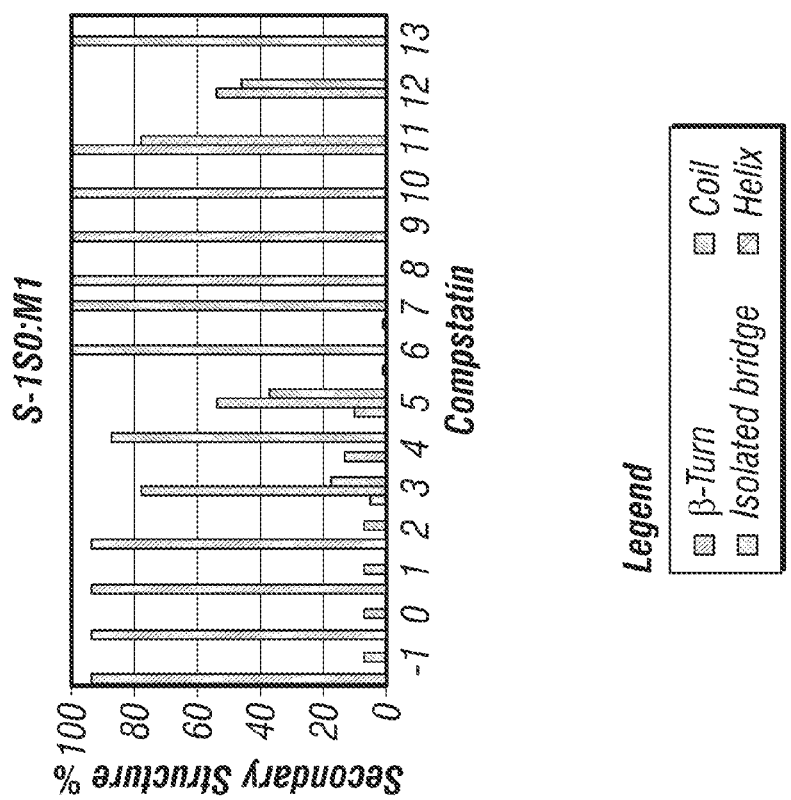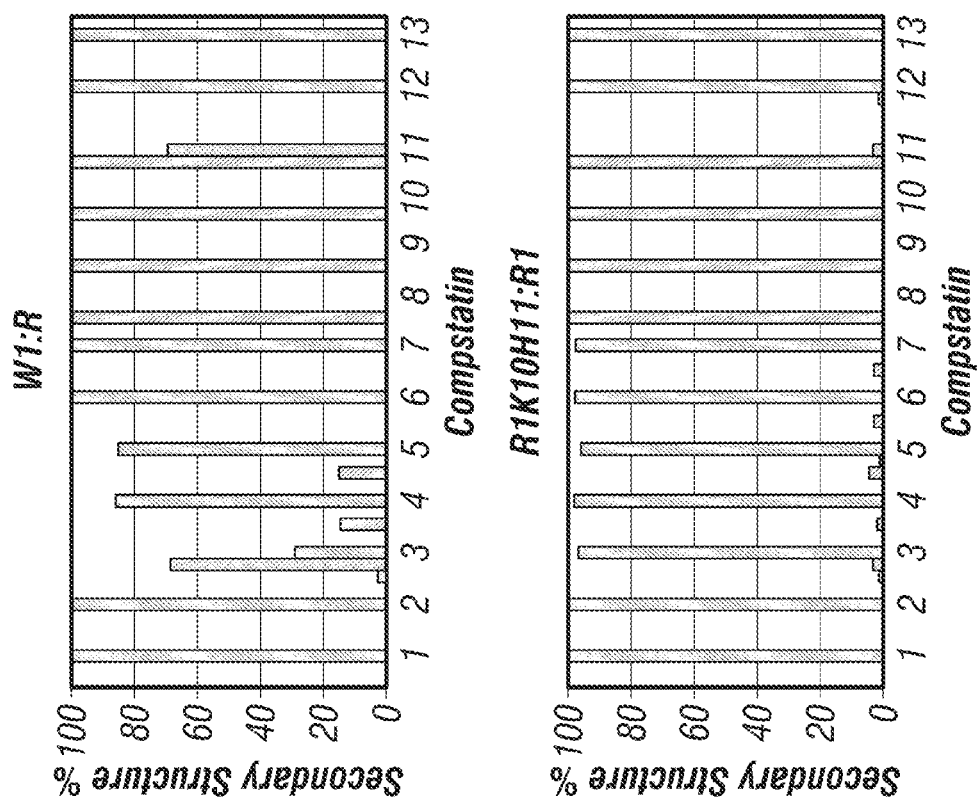
FIG. 5 (Cont'd)

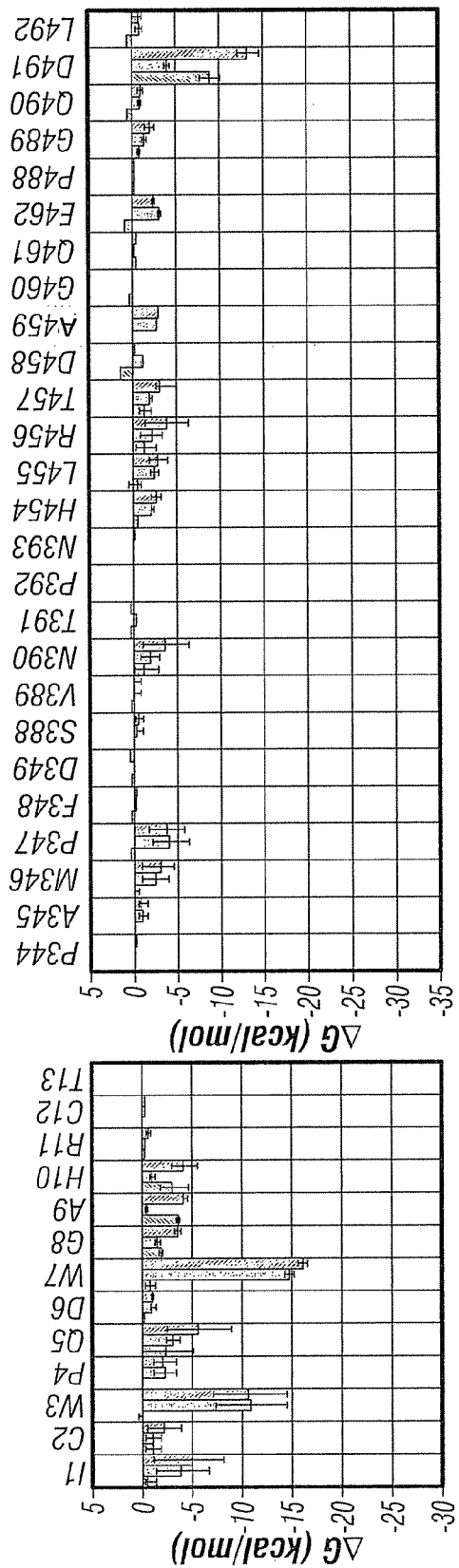
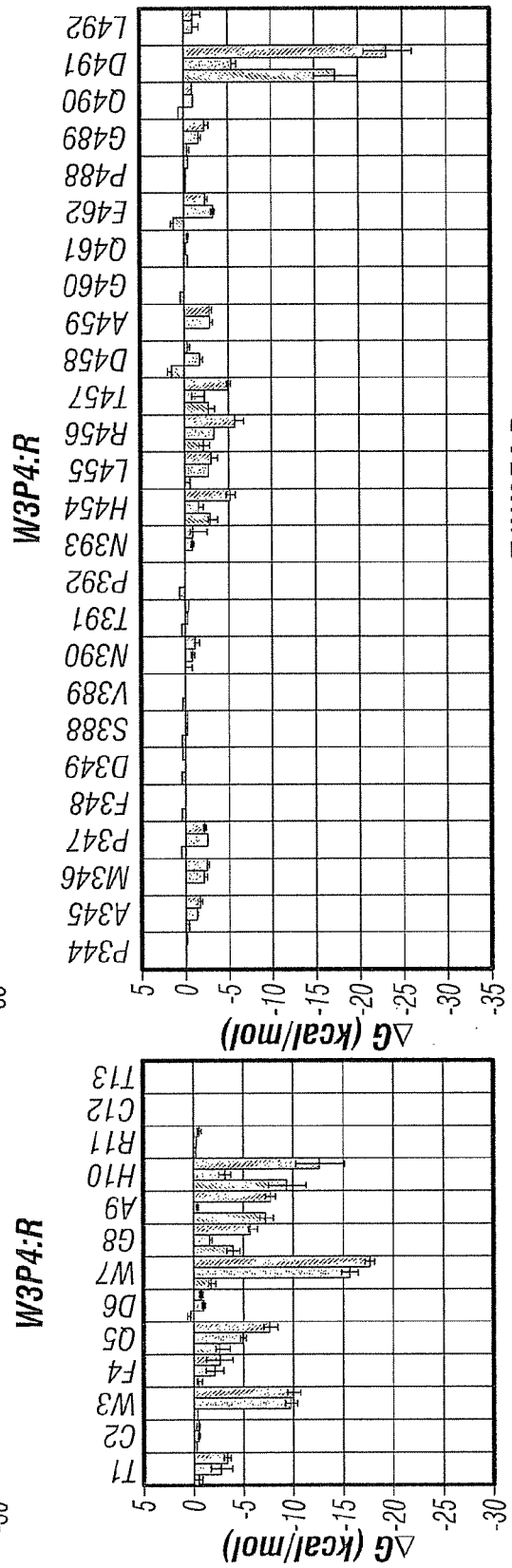
FIG. 6 (Cont'd)

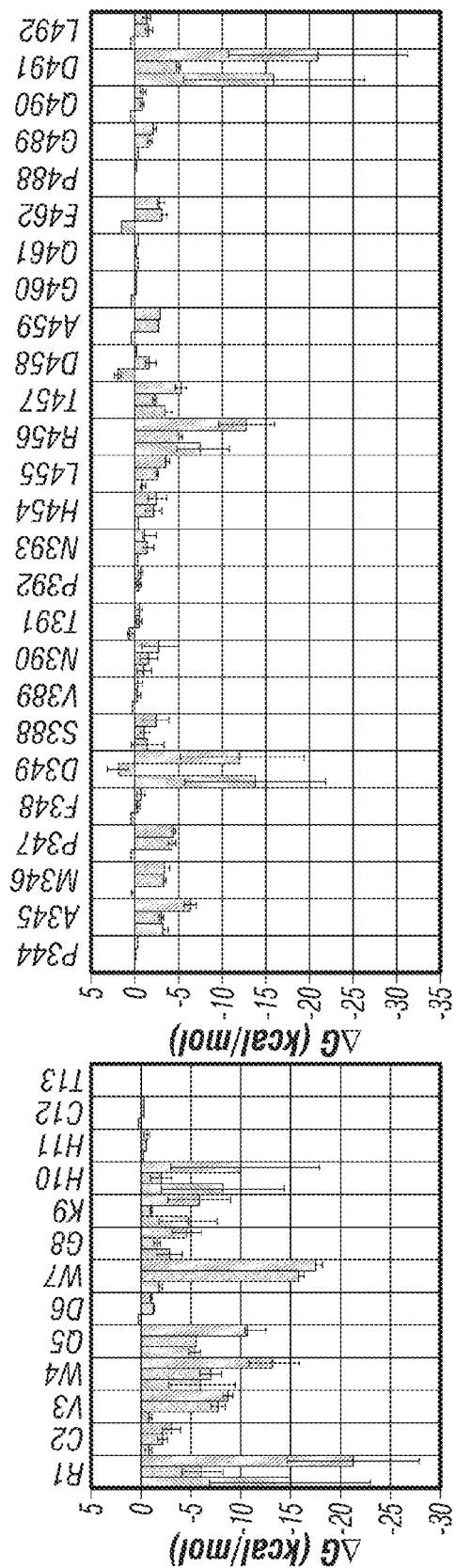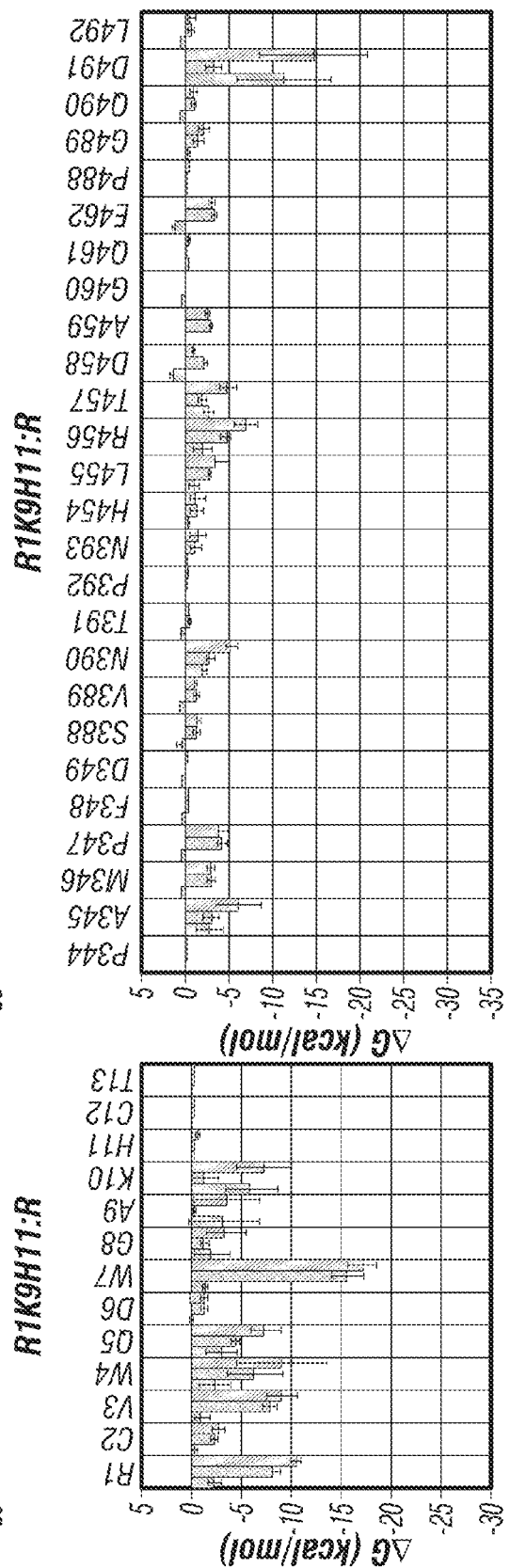
FIG. 6 (Cont'd)

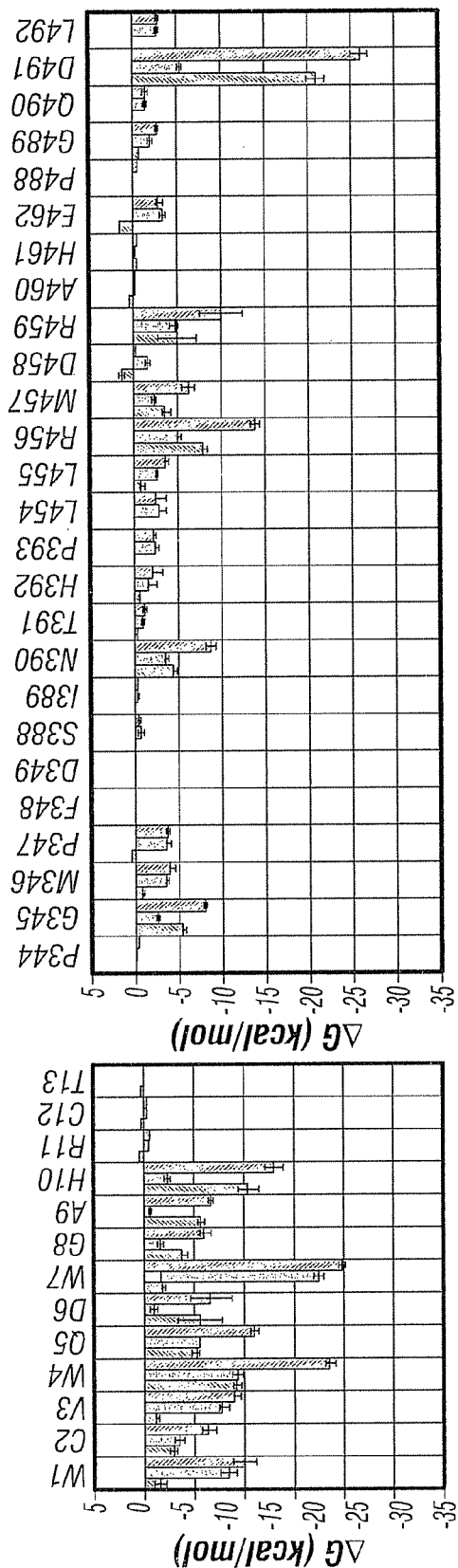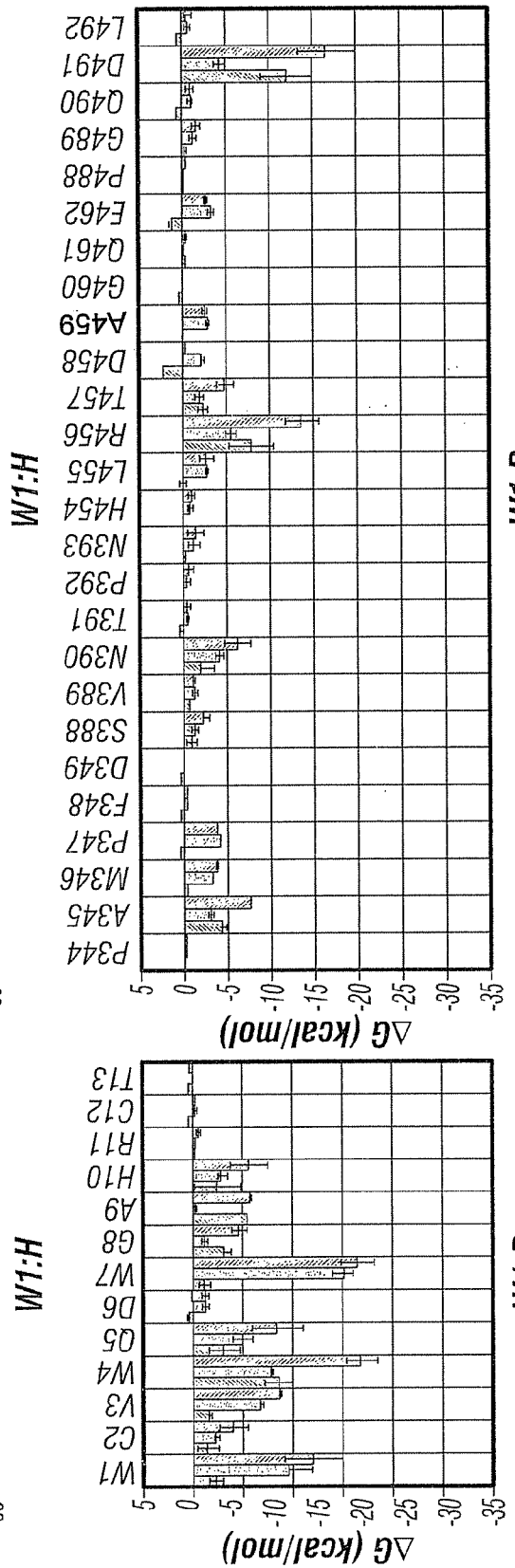
FIG. 6 (Cont'd)

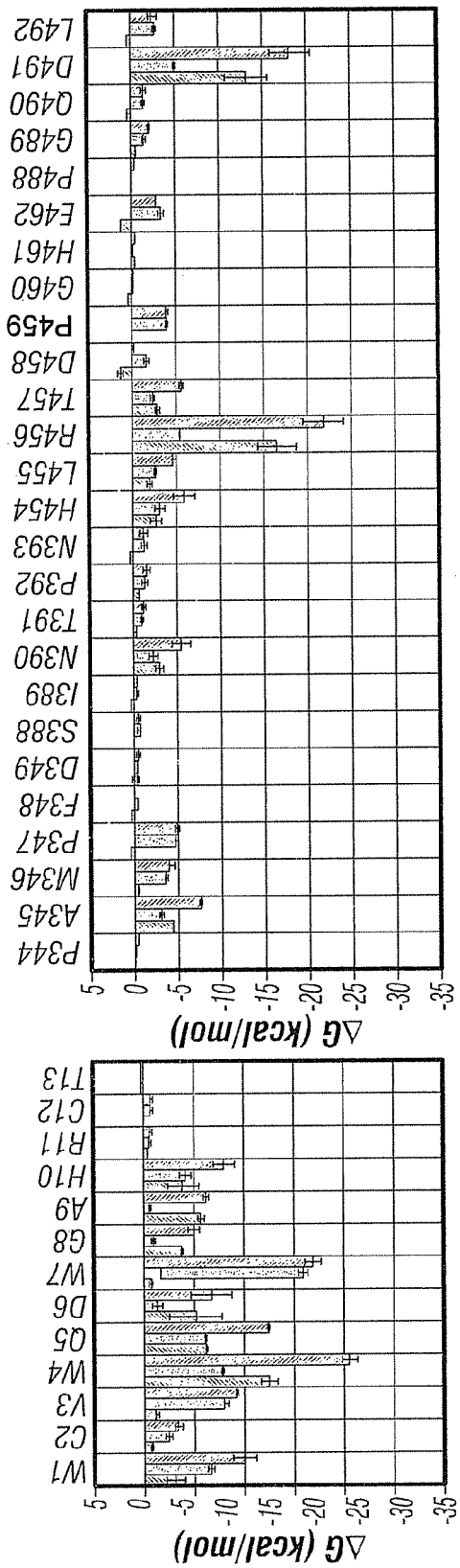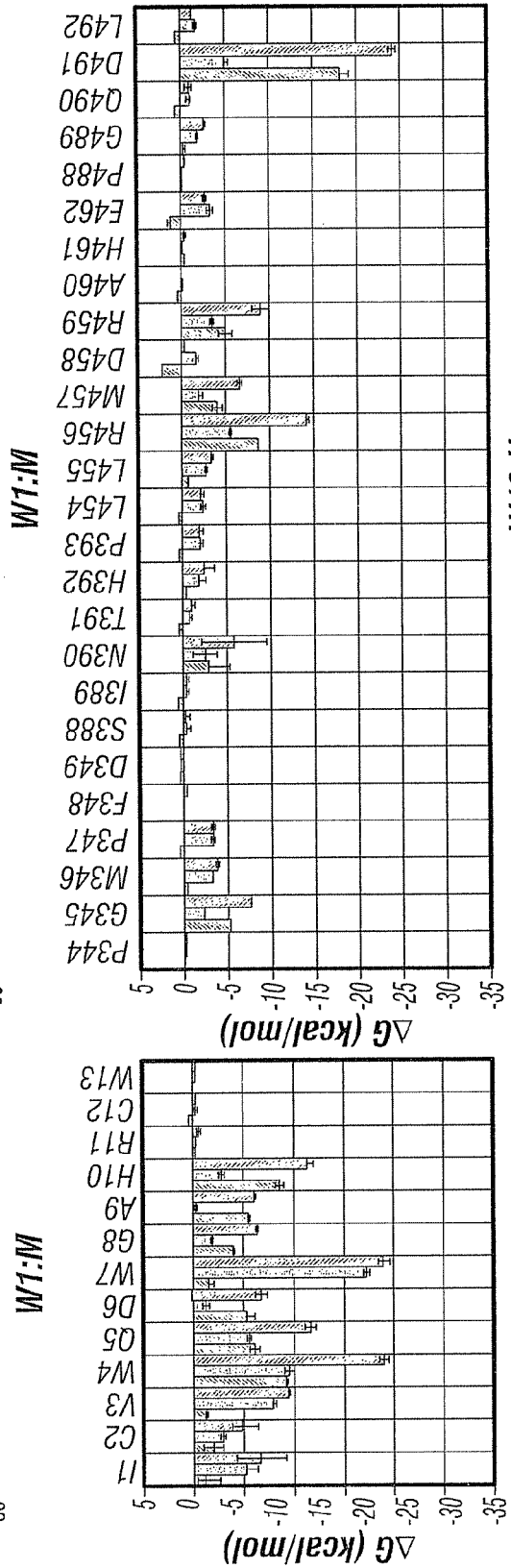
FIG. 6 (Cont'd)

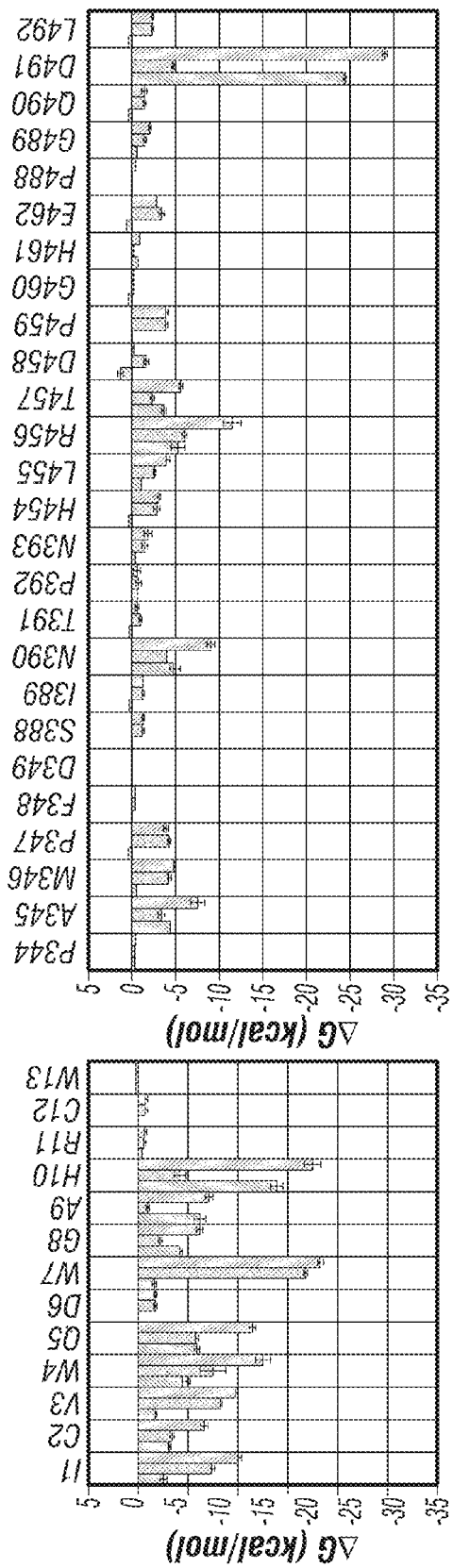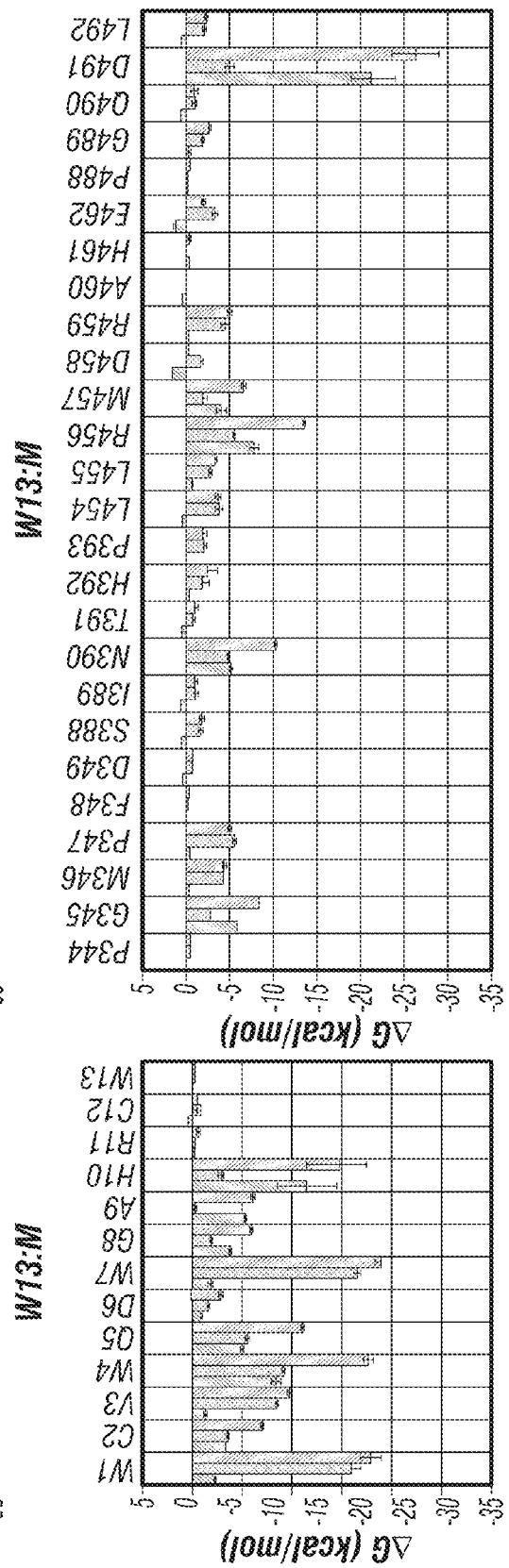
FIG. 6 (Cont'd)

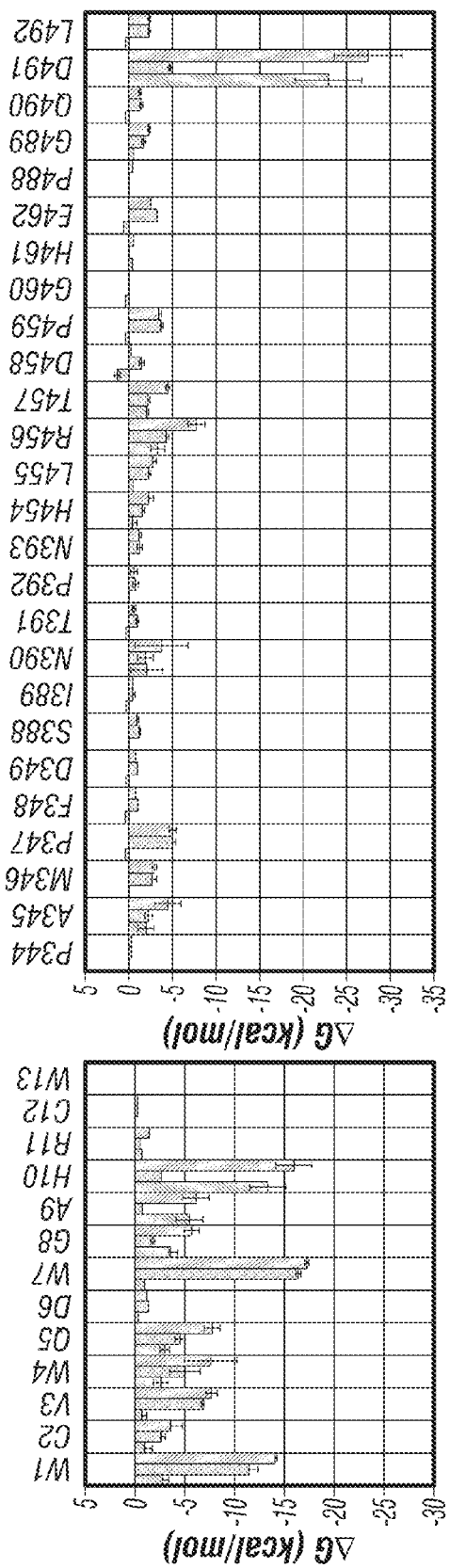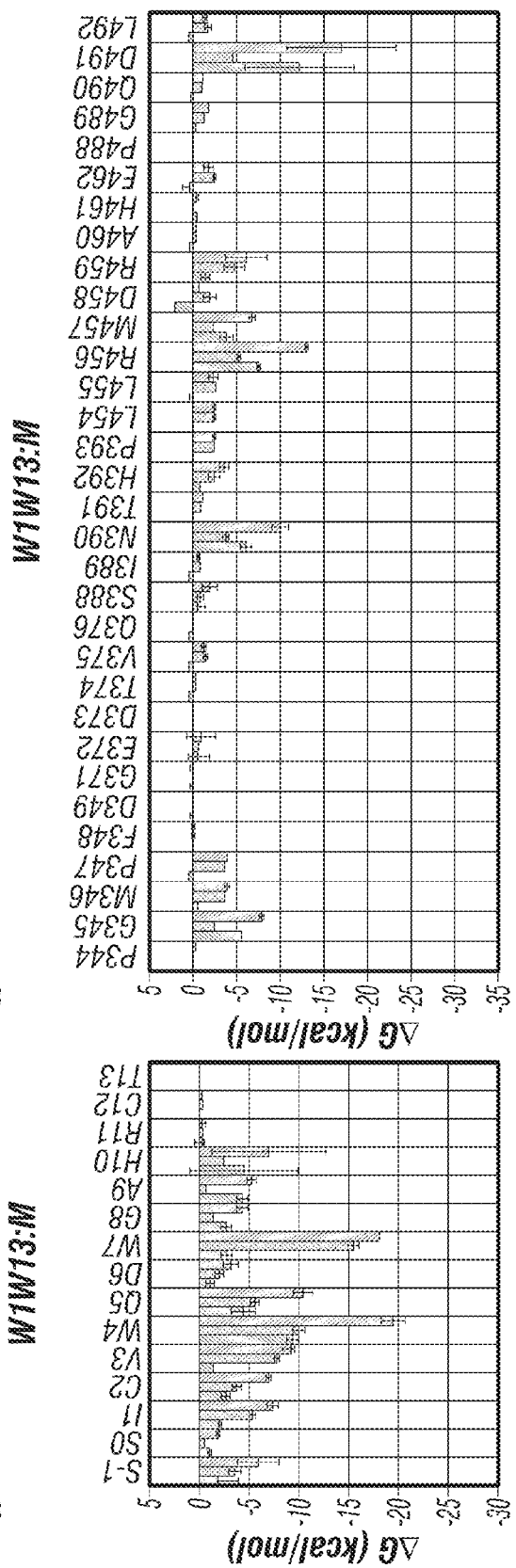
FIG. 6 (Cont'd)

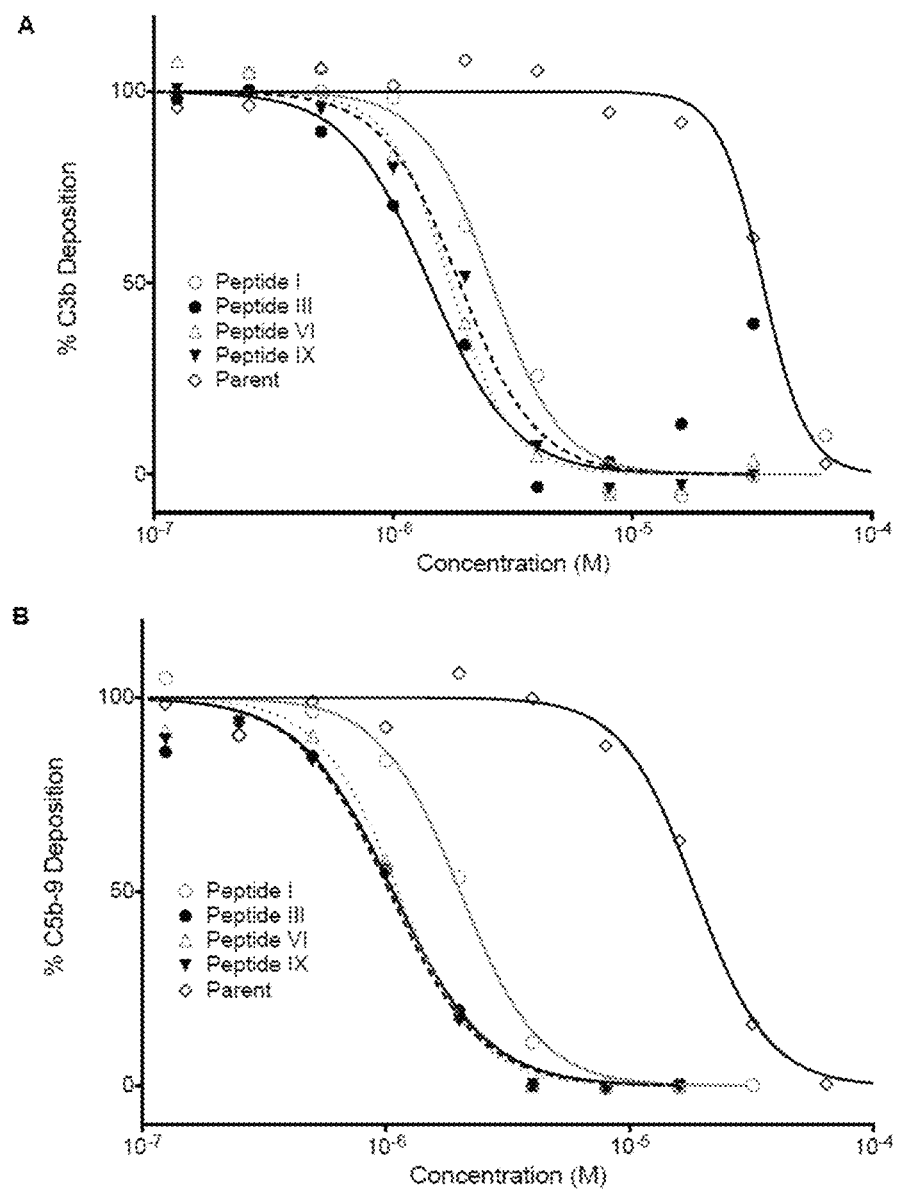
FIGURE 12A-B

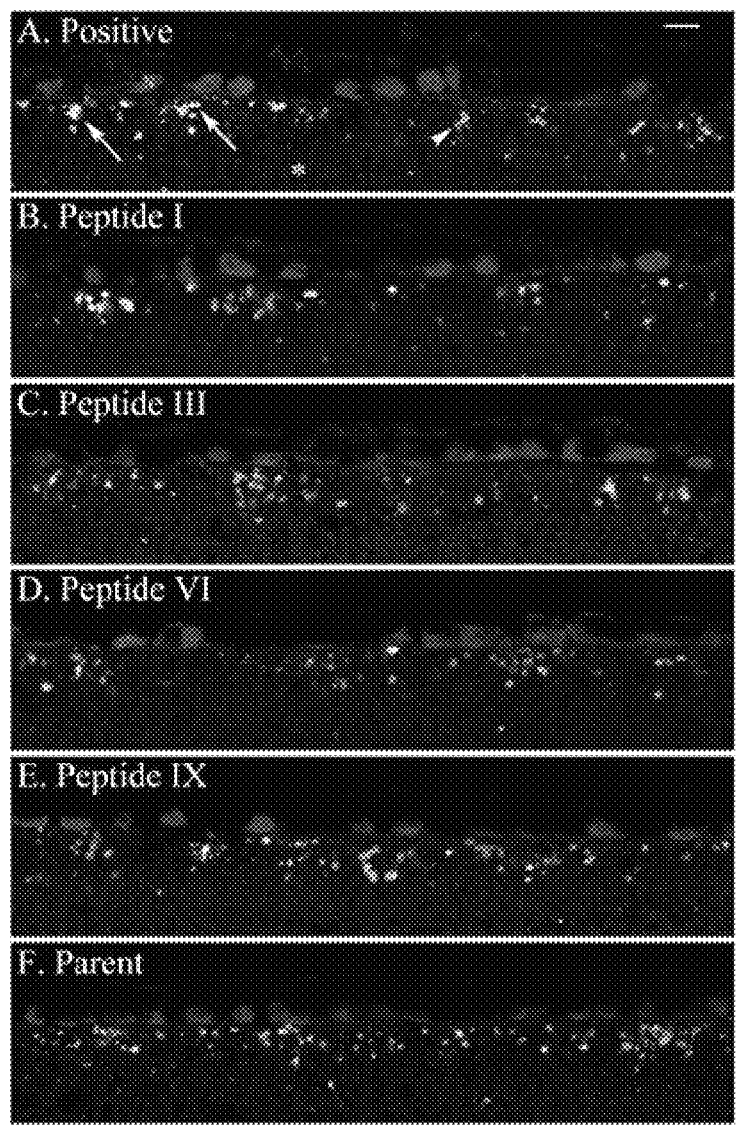
FIGURE 13A-F

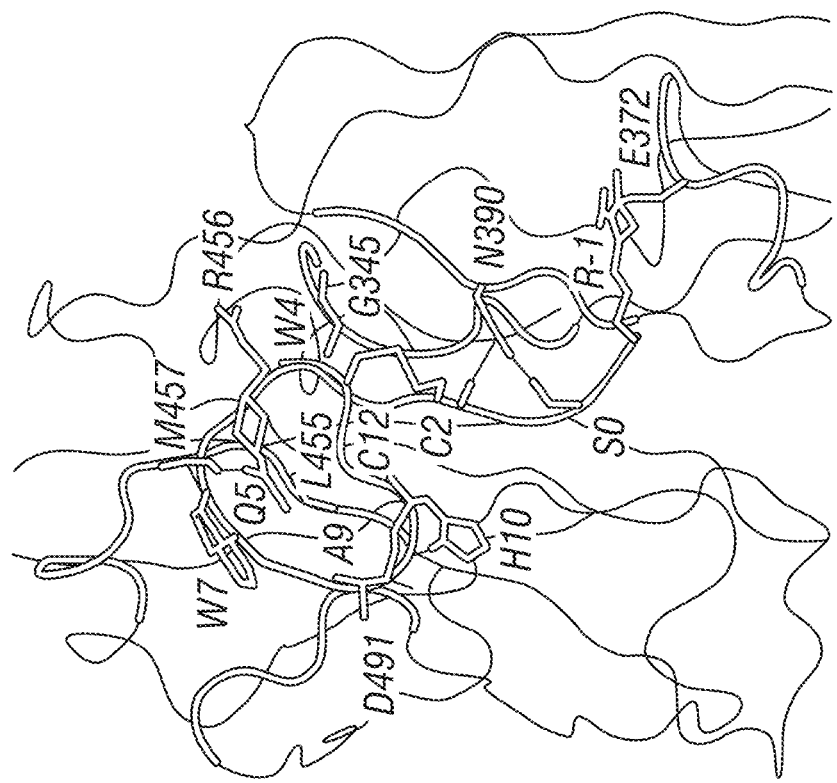
FIG. 16D
FIG. 16C

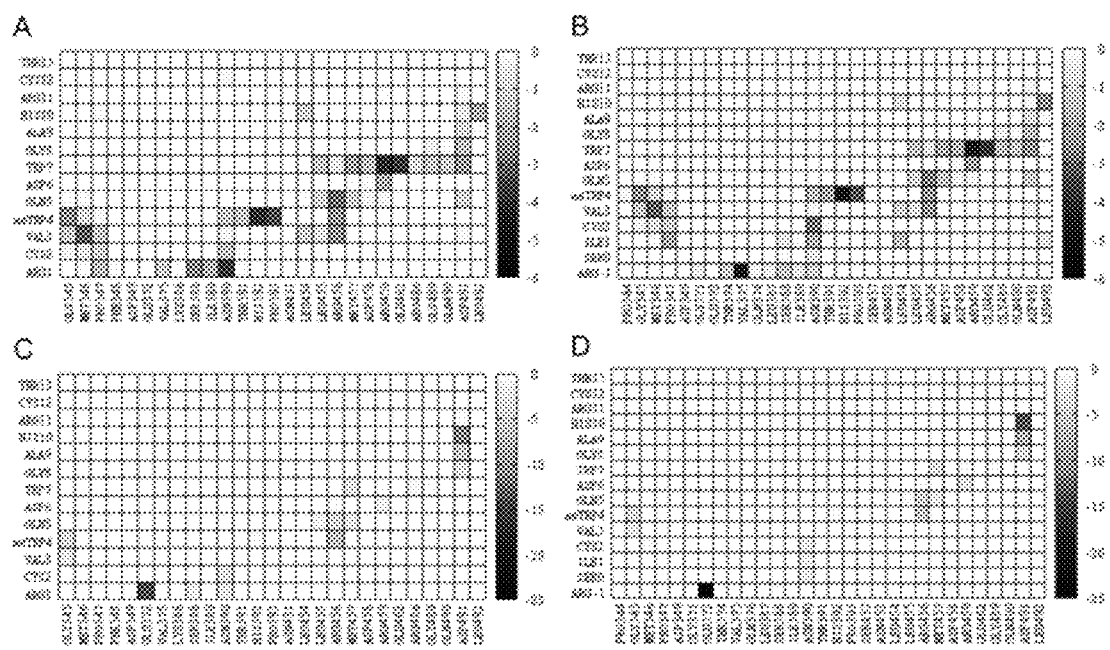
FIGURE 17A-D

COMPSTATIN ANALOGS

CROSS REFERENCE TO RELATED APPLICATIONS

This application is a U.S. National Stage Application filed under 35 U.S.C. §371 and claims priority to International Application No. PCT/US2013/76543, filed Dec. 19, 2013, which claims priority under 35 U.S.C. §119 from Provisional Application Ser. No. 61/739,438, filed Dec. 19, 2012, the disclosures of which are incorporated herein by reference.

STATEMENT REGARDING FEDERAL SPONSORED RESEARCH

This invention was made with government support under Grant No. R01-GM052032 awarded by the National Institutes of Health (NIH). The government has certain rights in the invention.

TECHNICAL FIELD

The disclosure provide analogs of compstatin useful for modulating the complement pathway in mammals.

BACKGROUND

Inappropriate or excessive complement activation may cause or aggravate several pathological conditions, such as age-related macular degeneration, asthma, adult respiratory distress syndrome, hemolytic anemia, rheumatoid arthritis, rejection of xeno-transplantation, stroke and heart attack. Regulating complement activation is important to control inflammation, disease and infection.

SUMMARY

The disclosure provide compstatin analogs useful for modulating complement activation. The disclosure provides compstatin analogs comprising the sequence $X_1X_2X_3CVX_4QDWGX_5HRCT$, wherein $X_1$ and $X_2$ may or may not be present, if $X_1$ and/or $X_2$ are present $X_1$ and/or $X_2$ can be any amino acid. In one embodiment, $X_1$ and $X_2$ can each independently be selected from polar amino acids (e.g., A, G, K, R, H, D, E, C Y, N, Q, S, T, W, A, G). In one embodiment, $X_1$ is selected from S, W, R, E or N and $X_2$ is selected from S, W, R or N; wherein $X_3$ is selected from W, meW, R, I or L; wherein $X_4$ is W, meW, Nmw, V, Y or a non-natural amino acid analog of alanine (Nmw is N-methyltryptophan); wherein $X_5$ is A or a non-natural amino acid analog of alanine; wherein the analog is acetylated at the N-terminus and amidated at the C-terminus; and wherein the compstatin analog is capable of binding mouse, rat or human C3. In one embodiment, $X_1$ and $X_2$ comprise a diserine extension. In another embodiment, the analogs is capable of binding rat or mouse C3. In another embodiment, $X_3$ is R, and $X_4$ is W. In yet a further embodiment, the analog is capable of binding rat or mouse C3. In yet another embodiment, the analog is used to treat a complement mediated disease in an individual at need of treatment. In yet another embodiment, the analog comprises a sequence selected from the group consisting of (a) AC-RCVWQDWGAHRCT-NH$_2$ (SEQ ID NO:5), (b) Ac-meWCVWQDWGAHRCT-NH$_2$ (SEQ ID NO:6), (c) Ac-RCVmeWQDWGAHRCT-NH$_2$ (SEQ ID NO:7), (d) Ac-SSICVWQDWGAHRCT-NH$_2$ (SEQ ID NO:8), (e) Ac-WWRCVWQDWGAHRCT-NH$_2$ (SEQ ID NO:9), (f) Ac-RSICVmeWQDWGAHRCT-NH$_2$ (SEQ ID NO:10), (g) Ac-RSRCVmeWQDWGAHRCT-NH$_2$ (SEQ ID NO:11), (h) Ac-SSRCVmeWQDWGAHRCT-NH$_2$ (SEQ ID NO:12), (i) Ac-ICVmeWQDWG(Nal)HRCT-NH$_2$ (SEQ ID NO:14); (j) Ac-ICVWQDWG(Nal)HRCT-NH$_2$ (SEQ ID NO:15); (k) Ac-ICVWQDWG(Rea)HRCT-NH$_2$ (SEQ ID NO:16); (l) Ac-ICVWQDWG(Aal)HRCT-NH$_2$ (SEQ ID NO:17); (m) Ac-ICVWQDWG(Sea)HRCT-NH$_2$ (SEQ ID NO:18); (n) Ac-ERICVWQDWGAHRCT-NH$_2$ (SEQ ID NO:19); (o) Ac-NNLCVWQDWGAHRCT-NH$_2$ (SEQ ID NO:20); (p) Ac-NRLCVWQDWGAHRCT-NH$_2$ (SEQ ID NO:21); (q) Ac-RSICVWQDWGAHRCT-NH$_2$ (SEQ ID NO:22); (r) Ac-ERICVWQDWG(Nal)HRCT-NH$_2$ (SEQ ID NO:23); (s) Ac-NNLCVWQDWG(Nal)HRCT-NH$_2$ (SEQ ID NO:24); (t) Ac-NRLCVWQDWG(Nal)HRCT-NH$_2$ (SEQ ID NO:25); (u) Ac-RSICVWQDWG(Nal)HRCT-NH$_2$ (SEQ ID NO:26); (v) Ac-ERICV(Nal)QDWG(Nal)HRCT-NH$_2$ (SEQ ID NO:27); (w) Ac-NNLCV(Nal)QDWG(Nal)HRCT-NH$_2$ (SEQ ID NO:28); (x) Ac-NRLCV(Nal)QDWG(Nal)HRCT-NH$_2$ (SEQ ID NO:29); and (y) Ac-RSICV(Nal)QDWG(Nal)HRCT-NH$_2$ (SEQ ID NO:30). In yet a further embodiment of any of the foregoing, the peptide is cyclized through a disulfide bond between the cysteine residues.

The disclosure also provides a method of using a compstatin analog of the disclosure for treating age-related macular degeneration or other complement system-mediated diseases, comprising contacting an individual in need of treatment with the compstatin analog to inhibit the activation of human or primate C3. In one embodiment, the analog is formulated in a composition comprising a pharmaceutically acceptable carrier. In another embodiment, the disease is selected from a group consisting of asthma, adult respiratory distress syndrome, hemolytic anemia, rheumatoid arthritis, rejection of xenotransplantation, stroke and heart attack. In another embodiment, the compstatin analog inhibits the classical complement pathway. In yet another embodiment, the compstatin analog inhibits the alternative complement pathway. In still another embodiment, the compstatin analog inhibits both the classical and alternate pathways. In one embodiment, the composition is administered intravenously. In yet another embodiment, the composition is administered intravitreally The details of one or more embodiments of the disclosure are set forth in the accompanying drawings and the description below. Other features, objects, and advantages will be apparent from the description and drawings, and from the claims.

DESCRIPTION OF DRAWINGS

FIG. 1A-F shows simulation structures of the compstatin binding site for the complexes R1:H (A, B), W1:H (C, D) and S-1S0:R (E, F) at the end of runs R1:H1, W1:H1 and S-1S0R1, respectively. Important hydrogen bonds and non-polar contacts are shown, respectively, in the left and right panel. The labels I-IV (in A) indicate four protein sectors with atoms at least within 7 Å from the ligand (344-349, 388-393, 454-462 and 488-492). Compstatin is shown in tubes and sticks. The dark tubes show the initial conformations of sectors I and II. The dark lines in plots A, C, E denote important hydrogen bonds. In plots B, D and F, protein residues are indicated by a larger surface, and ligand residues Cys2, Val3, Trp4, Trp7 and Cys12 are indicated by a smaller surface.

FIG. 2A-B shows residue intermolecular interaction energy differences between the complex W4A9:hC3 and selected complexes described herein. Compstatin and C3 results are in the left and right panel. Data are averaged over all respective runs. The uncertainties (error bars) are computed as described in methods. (A) W4A9:hC3-S-1S0:R difference; (B) W4A9:hC3-S-1S0:M difference. Positive/negative values indicate, respectively, gained/lost interactions in the present complexes, relative to the W4A9:hC3 complex. C3 regions interacting with compstatin analogs are enclosed in boxes in (A), grey-scaled as follows: sector 344-349; sector 371-376; sector 388-393; sector 454-462; and sector 488-492. An additional residue, A377, is shown in the orange box to account for possible compensatory effects due to the E372 deletion with respect to human C3 (not present).

FIG. 4 shows an alignment of human (SEQ ID NO:2), rat (SEQ ID NO:3) and mouse (SEQ ID NO:4) C3 sequences, prepared with CLUSTALW v. 2.0.12. An asterisk (*) indicates invariant, a colon (:) strongly similar and a period (.) weekly similar amino acids; a dash (-) indicates sequence gaps introduced by the alignment. Regions interacting with the ligand are enclosed in rectangular boxes.

FIG. 12A-C shows ELISA and hemolytic assay data used to extract the $IC_{50}$ values of Table 1. (A) C3b ELISA data, representing the inhibition of cleavage of C3 to C3a and C3b by compstatin peptides, quantified as inhibition of the formation of C3b. (B) C5b-9 ELISA data, representing inhibition of the formation of the C5b-9 terminal complex of complement activation. (C) Hemolytic assay data, representing inhibition of rabbit erythrocyte hemolysis by the C5b-9 terminal complex activation. The data points and error bars correspond to means and S.E.M. from three independent experiments.

FIG. 13A-F shows confocal microscopy immunofluorescence images of C5b-9 deposition. Examples of confocal immunofluorescence images of sub-RPE deposit-associated C5b-9 immunolabeling. ApoE immunolabeling of deposits, with areas of co-localization represented. The effects of the inhibitory peptides are illustrated by the reduced amounts of C5b-9-specific labeling in B-F. Consistent with the C5b-9 ELISA data, Peptides III, VI, and IX reduce C5b-9-specific labeling most significantly compared to the positive control (A). N=nucleus in A; arrows in A indicate C5b-9 immunolabeling; arrowhead in A indicates ApoE deposits; background autofluorescence of the cell culture support is indicated by asterisk in A; scale bar in A=10 μm.

FIG. 16A-F shows intermolecular contacts of Peptides III, VI and IX with C3 from molecular dynamics simulations. Simulation structures of the C3 binding site with Peptides III (A, B), VI (C, D), and control Peptide IX (E, F) at the end of the molecular dynamics simulations. Important hydrogen bonds and nonpolar binding pockets are shown, respectively, in the left and right panels. Five interacting C3 sectors (344-349; 371-376; 388-393; 454-462; and 488-492) with heavy atoms up to 7.5 Å from the Peptide VI ligand are shown in tube (A, C, E) and surface (B, D, F) representation. The lines in (A, C, E) denote important hydrogen bonds. All hydrogen atoms, except for those participating in hydrogen bonds (in A, C, E), are omitted for clarity. In panels (A, C, E) important main/side chain hydrogen bonding protein-ligand residue pairs are shown. In panels (B, D, F) important ligand side chain groups, lying on or binding into the protein surface are shown.

FIG. 17A-D shows energetic analysis of intermolecular contacts of Peptides III and VI with C3 from molecular dynamics simulations. Two dimensional density maps depicting the favorable (negative) average MM GBSA interaction free-energies for intermolecular ligand (y axis)—C3 (x axis) interacting residue pairs, within the simulation of Peptides III (A, C) and VI (B, D) in complex with C3. The upper panels (A, B) correspond to polar interactions, and the bottom panels (B, D) correspond to nonpolar interactions. All energies are in kcal/mol. The color code for the interaction free energy is shown in the palette on the right-hand side of each panel.

DETAILED DESCRIPTION

Figure 1D:
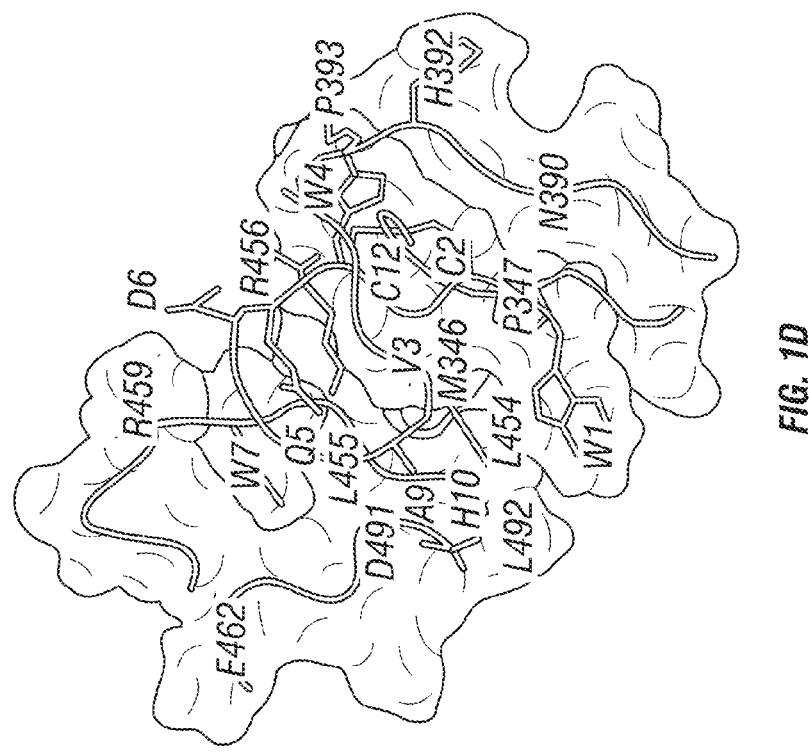

As used herein and in the appended claims, the singular forms "a," "and," and "the" include plural referents unless the context clearly dictates otherwise. Thus, for example, reference to "an analog" includes a plurality of such analogs and reference to "the composition" includes reference to one or more compositions and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. However, with respect to any similar or identical terms found in both the incorporated publications or references and those expressly put forth or defined in this application, then those terms definitions or meanings expressly put forth in this application shall control in all respects. The publications discussed above and throughout the text are provided solely for their disclosure prior to the filing date of the present application. Nothing herein is to be construed as an admission that the inventors are not entitled to antedate such disclosure by virtue of prior disclosure.

Complement activation proceeds via three biochemical pathways (classical, alternative and lectin), which converge to a common point, the cleavage of the protein C3 to fragments C3a and C3b. The larger fragment, C3b, tags pathogen surfaces for recognition by phagocytic cells (opsonization), and the smaller fragment, C3a, aids in immune cell recruitment (chemotaxis) and inflammation. The C3b fragment also participates in complexes, called convertases, which are responsible for cleavage of C3 to C3a and C3b, as well as cleavage of complement protein C5 to C5a and C5b. C5 is the starting protein of the common activation pathway, which ends with the formation of the membrane attack complex (MAC), a multicomponent protein assembly involved in lysis of pathogen membranes. Protein C3 is essential in all pathways and represents a target for complement inhibition. For example, regulation of C3 cleavage can control the effects of C3a and C3b, and the progression of complement activation to C5, and, eventually, to MAC. Altogether, regulation of C3 would affect the opsonization, chemotactic, inflammatory, and lytic capabilities of the complement system.

The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils. C3 and C5 convertase activity is controlled by a number of endogenous members of the Regulators of Complement Activation (RCA) family, also called Complement Control Protein (CCP) family, which includes complement receptor type 1 (CR1; C3b:C4b receptor), complement receptor type 2 (CR2), membrane cofactor protein (MCP; CD46), decay-accelerating factor (DAF), factor H (fH), and C4b-binding protein (C4 bp).

The alternative pathway is initiated by microbial surfaces and various complex polysaccharides. In this pathway, C3b, resulting from cleavage of C3, which occurs spontaneously at a low level, binds to targets, e.g., on cell surfaces and forms a complex with factor B, which is later cleaved by factor D, resulting in a C3 convertase. Cleavage of C3 and binding of another molecule of C3b to the C3 convertase gives rise to a C5 convertase. C3 and C5 convertases of this pathway are regulated by CR1, DAF, MCP, and fH. The mode of action of these proteins involves either decay accelerating activity (i.e., ability to dissociate convertases), ability to serve as cofactors in the degradation of C3b or C4b by factor I, or both.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The third complement pathway, the lectin complement pathway is initiated by binding of mannose-binding lectin (MBL) and MBL-associated serine protease (MASP) to carbohydrates. In the human lectin pathway, MASP-I and MASP-2 are involved in the proteolysis of C4, C2 and C3, leading to a C3 convertase described above.

Complement activity is regulated by various mammalian proteins referred to as complement control proteins (CCPs). These proteins differ with respect to ligand specificity and mechanism(s) of complement inhibition (Lisczewski, M K and Atkinson, J P, in The Human Complement System in Health and Disease, eds. Volanakis, J E and Frank, M M, Dekker, New York, pp. 149-66, 1998). They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains (Reid, KBM and Day, AJ, Immunol Today, 10:177-80, 1989). These domains, consisting of approximately 50-70 amino acids, typically about 60 amino acids, are characterized by a conserved motif that includes four disulfide-bonded cysteines (two disulfide bonds), proline, tryptophan, and many hydrophobic residues.

A "complement component" or "complement protein" is a molecule that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, H, and I, and properdin.

The peptide compstatin binds to human and primate C3 and prevents its cleavage to C3a and C3b, a key step in complement activation. Compstatin also binds to the C3b fragment as well as the inactive C3c fragment, both of which contain the C3 β-chain. Compstatin has the sequence ICV-VQDWGHHRCT (SEQ ID NO:1) and is maintained in a cyclic conformation via the disulfide bridge between the cysteines at position 2 and 12. Compstatin has been examined as a promising candidate for the treatment of unregulated complement activation. Importantly, it is active against C3 from primate mammals, but inactive against C3 of non-primate mammals. This species specificity precludes the development of related disease models in non-primate animals. Thus, the development of active compstatin analogs against non-primate targets, such as rat C3 (rC3) or mouse C3 (mC3), is an important, unaccomplished to-date goal.

Using rational design methods a number of analogs of compstatin were developed and are described herein. These analogs provide cross-species inhibitory capabilities and thus open the door for development of animal models of diseases. These analogs were developed by employing a de novo design methods to identify novel, compstatin-based inhibitors of human C3. Using activity measurements, selected analogs with aromatic (Trp) substitutions at one or both terminal ends had activity similar to the activity of the N-terminal acetylated mutant V4W/H9A (W4A9). Furthermore, using atomistic molecular dynamics (MD) simulations of W4A9 complexes with hC3 or rC3, a mechanistic interpretation for the species-specificity of compstatin was developed at the molecular level and a "transgenic" mC3 analog was designed with human-like binding site characteristics.

The disclosure provides the development of compstatin analogs by employing a combination of de novo design/ atomistic MD simulations, to identify compstatin-based analogs with promising affinity for non-primate C3. Furthermore, the complexes of the most promising inhibitors with hC3 were studied and compared with W4A9, the best to-date natural-amino acid inhibitor of the human protein.

As used herein, the term "compstatin analog" includes any complement inhibiting analog of compstatin as described herein. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. The assay may, for example, measure alternative pathway-mediated erythrocyte lysis or be an ELISA assay (see Example 2, below). The disclosure includes embodiments in which any one or more of the compstatin analogs or compositions described herein is used in any the methods of treatment of a disease or disorder associate with aberrant complement activation.

The activity of a compstatin analog may be expressed in terms of its $IC_{50}$ (the concentration of the compound that inhibits complement activation by 50%), with a lower $IC_{50}$ indicating a higher activity as recognized in the art. The activity of a compstatin analog for use in the disclosure is at least as great as that of compstatin or substantially similar. The $IC_{50}$ of compstatin has been measured as 12 µM using an alternative pathway-mediated erythrocyte lysis assay. In one embodiment, the $IC_{50}$ of the compstatin analog is no more than the $IC_{50}$ of compstatin.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof.

In certain embodiments of the disclosure the sequence of the compstatin analog comprises or consists essentially of a sequence that is obtained by making 1, 2, 3, or 4 substitutions or insertion in the sequence of compstatin, i.e., 1, 2, 3, or 4 amino acids is replaced by a different standard amino acid or by a non-standard amino acid. In certain embodiments of the disclosure the amino acid at position 4 is altered. In certain embodiments of the disclosure the amino acid at position 9 is altered. In certain embodiments of the disclosure the amino acids at positions 4 and 9 are altered. In other embodiments, the sequence of any of the compstatin analogs whose sequence is obtained by replacing one or more amino acids of compstatin sequence further includes up to 1, 2, or 3 additional amino acids at the N-terminus.

Compstatin and certain compstatin analogs having somewhat greater activity than compstatin contain only naturally occurring amino acids (i.e., glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-natural amino acids. Useful non-natural amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and $\alpha,\alpha$-disubstituted amino acids. In certain embodiments of the disclosure, a compstatin analog is designed by replacing one or more L-amino acids in a compstatin analog described elsewhere herein with the corresponding D-amino acid. Exemplary non-standard amino acids of use include 2-naphthylalanine (2-Nal), 1-naphthylalanine (1-Nal), 2-indanylglycine carboxylic acid (2IgI), dihydrotrpytophan (Dht), 4-benzoyl-L-phenylalanine (Bpa), 2-D-aminobutyric acid (2-Abu), 3-$\alpha$-aminobutyric acid (3-Abu), 4-$\alpha$-aminobutyric acid (4-Abu), cyclohexylalanine (Cha), homocyclohexylalanine (hCha), 4-fluoro-L-tryptophan (4fW), 5-fiuoro-L-tryptophan (5fW), 6-fluoro-L-tryptophan (6fW), 4-hydroxy-L-tryptophan (4OH-W), 5-hydroxy-L-tryptophan (5OH-W), 6-hydroxy-L-tryptophan (6OH-W), 1-methyl-L-tryptophan (lMeW), 4-methyl-L-tryptophan (4MeW), 5-methyl-L-tryptophan (5MeW), 7-aza-L-tryptophan (7aW), D-methyl-L-tryptophan (DMeW), $\beta$-methyl-L-tryptophan ($\beta$MeW), N-methyl-L-tryptophan (NMeW), Nma (N-methylalanine) and Nmw (N-methyltryptophan), ornithine (orn), citrulline, norleucine, $\gamma$-glutamic acid, etc.

In certain embodiments of the disclosure the compstatin analog comprises one or more Trp analogs (e.g., at positions −1, 0, 4 and/or 7 relative to the sequence of compstatin). Exemplary Trp analogs are mentioned above (e.g., methylated and halogenated Trp and other Trp and indole analogs). Other Trp analogs include variants that are substituted (e.g., by a methyl group). Amino acids comprising two or more aromatic rings, including substituted, unsubstituted, or alternatively substituted variants thereof, are of interest as Trp analogs.

In certain embodiments of the disclosure, the compstatin analog comprises one or more Ala analogs (e.g., at position 9 relative to the sequence of compstatin), e.g., Ala analogs that are identical to Ala except that they include one or more CH2 groups in the side chain. In certain embodiments the Ala analog is an unbranched single methyl amino acid such as 2-Abu. In certain embodiments of the disclosure the compstatin analog comprises one or more Trp analogs (e.g., at position 4 and/or 7 relative to the sequence of compstatin) and an Ala analog (e.g., at position 9 relative to the sequence of compstatin).

The disclosure provide a number of compstatin peptide/polypeptide analogs having a sequence comprising or consisting of: $X_1X_2X_3CVX_4QDWGX_5HRCT$ (SEQ ID NO:55) wherein $X_1$ and $X_2$ may or may not be present, if $X_1$ and/or $X_2$ are present $X_1$ and $X_2$ are independently selected from (a) any amino acid, (b) a polar amino acid (e.g., K, R, H, D, E, C, Y, N, Q, S, T, W, A, G) or (c) S, W, meW, R, E or N; wherein $X_3$ is selected from W, meW, R, I or L; and wherein $X_4$ is W or meW and wherein a disulfide bond is formed between the cysteines to cyclize the molecule. A compstatin analog of the disclosure is capable of binding mouse, rat and/or human C3. "meW" refers to a methylated tryptophan such as 2-Amino-3-(1-methyl-1H-indol-3-yl)propanoic acid. In one embodiment, $X_1$ and $X_2$ comprise a diserine extension. In a further embodiment, the diserine compstatin analog can comprise a sequence Ac-SSRCVWQDWGAH-RCT-NH$_2$ or Ac-SSICVWQDWGAHRCT-NH$_2$ (the tryptophan can be methylated at position 6 of the two foregoing sequences). In another embodiment, $X_3$ is R, and $X_4$ is W or meW. In another embodiment, $X_5$ is selected from Nal (1-naphthylalanine or 2-naphthylalanine), Rea, and Sea. In a further embodiment, the compstatin analog comprise the sequence Ac-RCVWQDWGAHRCT-NH$_2$ or Ac-RCVW(Me)QDWGAHRCT-NH$_2$. Other compstatin analogs of the disclosure that meet the consensus sequence of SEQ ID NO:55 are set forth in Table 7.

The analogs of the disclosure included substitutions which inserted additional interaction capabilities at the ligand terminal ends and, sometimes, positions 9-11; the x-ray structure of the W4A9:hC3 complex, and MD simulations of the human and rC3 complexes suggested that the corresponding W4A9 residues did not make optimum intermolecular interactions, leaving room for improvement; this was especially true in the simulations of the rat complex, due to localized, reproducible structural changes of protein sectors near the ligand.

The insertion of an Arg side-chain at position 1 was estimated to improve the ligand affinity for both rC3 (Table 6) and hC3 (Table 1, below), prompting the study of the second-generation analogs. This was mainly due to the formation of a stable salt bridge Arg1-Asp349, together with the reproduction of most other intermolecular interactions seen in the W4A9:hC3 complex. Note that the polar free-energy component for the R1:H complex is negative (Table 3), whereas it is positive for all other complexes (Table 3 and 6); this implies that the salt bridge compensates for the free-energy increase, due to the transfer of the Arg1 charge from water into the complex. Apart from its contribution to affinity, the N-terminal charge improves the solubility of the ligand, an important consideration in drug development.

Other experiments examined the insertion of tryptophan amino acids in compstatin which might create avenues for mechanistic binding studies to C3, which would exploit the diverse physicochemical properties of tryptophan, i.e. its hydrophobicity (benzene ring), hydrogen-bond donor capability (indole amide) and its capability for n-stacking or n-cation interactions. The experiments showed that the Trp1 ligand was soluble and had a near-W4A9 inhibitory activity for hC3. In the MD simulations of the W1:hC3 complex, the Trp1 side chain formed nonpolar interactions with His10 and Leu492 and W1 had a near-W4A9 affinity (Table 3). Overall, the simulations suggest that the Trp1 substitution improves affinity for both human and non-primate C3, but to a smaller extent than Arg1. The Trp13 substitution reduced the experimental solubility of compstatin analogs, restricting its potential use in compstatin-based drugs. Despite this result, the combination of a Trp13 substitution with solubility-increasing mutations, by introducing polar amino acids, might yield promising inhibitors. To obtain insights on the potential interactions of Trp13 with C3, this mutation was included in two of the simulated analogs. One analog (W13) had somewhat smaller affinity for hC3, relative to W4A9; the second analog (W1W13) had significantly increased affinity (Table 6). In both complexes, most new intermolecular interactions (relative to W4A9) were formed by Trp1. Trp13 was solvent-exposed, or made intramolecular n-cation interactions with Arg11.

The introduction of the diserine extension at the N-terminal end (fourth-generation) was prompted by the displacement of sector 388-393 away from the ligand in the non-primate simulations, which eliminated or weakened interactions with Asn390 and caused the overall destabilization of the non-primate C3-W4A9 complex. In the simulated non-primate and human complexes, the interaction of the Cys2 main chain with Asn390 was retained and a novel interaction was formed, involving the main-chain of Ser0. The non-primate sector 388-393 was displaced away from the ligand to a smaller extent, relative to other non-primate complexes (Table 4), and the computed affinity for r/mC3 was improved by ~10 kcal/mol. In addition, the polar diserine extension adds much needed solubility at the N-terminus.

As discussed in more detail elsewhere herein, the performance of MM-GB/SA, that is employed here to estimate the complex stabilities, is fragile, as it is based on numerous assumptions. In particular, the "one-trajectory" approximation eliminates contributions from intramolecular energies, which contribute thousands of kcal/mol to the energies of the complex and free protein [Eq. (2), below] and may introduce large uncertainties in the relative affinities; on the other hand, the protein and/or ligand structural relaxation, which are ignored in this approximation, may contribute a few kcal/mol to relative affinities. In the case of W4A9, the "one-trajectory" approximation yields a +9 kcal/mol relative affinity, disfavoring rC3 over hC3. This estimate has the correct sign, since W4A9 is experimentally inactive against rC3; in fact, it is probably a lower bound to the relative affinity, since a "three-trajectory" approximation increases the value to ~+19 kcal/mol. Thus, relative affinities of this magnitude (~+10 kcal/mol) or larger may be indicative of ligands specific for human (vs non-primate) C3.

The first-generation ligands have rC3 affinities in the range −37 to −41 kcal/mol (Table 6); these are weaker than the affinity of W4A9 for rC3 and hC3, respectively, by 5 to 9 kcal/mol and 15 to 19 kcal/mol. At the same time, the rC3 complexes of these ligands experience localized structural changes (Table 4), which disrupt or eliminate intermolecular interactions seen in the human complex (Table 5A).

The second- and third-generation ligands have rC3 affinities in the range −46 to −51 kcal/mol and hC3 affinities in the range −56 to −59 kcal/mol. Both estimates are similar, or slightly better than the corresponding affinities of W4A9 (−46 and −55 kcal/mol). Thus, the computed affinities of these ligands for hC3 are stronger by at least 5 kcal/mol; the associated free-energy uncertainties (in the "one-trajectory" approximation) are smaller (between 0.2-3.0 kcal/mol). Overall, these results suggest that ligands of these two groups bind human and rC3 with a near-W4A9.

Ligand S-1S0 (fourth generation) has near-W4A9 affinity for hC3 (~−57 kcal/mol) and in the range −55 to −57 kcal/mol for non-primate C3. The two-residue extension contains four more main chain torsional angles, compared to β-residue analogs. Assuming an upper-bound of ~0.6 kcal/mol loss in conformational entropy ($-T\Delta S$) per rotatable bond upon binding, the S-1S0 affinities could be overestimated with respect to the corresponding W4A9 affinities, possibly by ~2.5 kcal/mol. On the other hand, the computed relative (human—rat) affinity of S-1S0 is near ~0 kcal/mol. Conformational-entropy corrections should affect to a similar extent the S-1S0 affinity for human and rC3, leaving the relative affinity estimate unmodified. In comparison, the relative W4A9 affinity is +9 kcal/mol. The dramatic improvement of S-1S0 affinity for rC3 is due to improved interactions, and suggests that S-1S0, or other compounds carrying an N-terminal extension, are worth exploring further as promising inhibitors of non-primate C3.

For some of the peptides studied here, W1, W13, R1, and S-1S0, there is experimental evidence for inhibitory activity against hC3. W1 showed that it had near-W4A9 inhibitory activity and good solubility, whereas W13 suffered from solubility problems in aqueous environment. The peptide R1 was found to be active in a study that aimed to delineate the role of acetylation in producing a 3-fold increase in inhibitory activity compared to non-acetylated compstatin. The structural rationale was that the positively charged backbone amino group was disrupting the hydrophobic cluster at the termini (spanning residues 11-C2-V3-V4/C12/T13 of native compstatin), which was deemed necessary for binding and activity before the availability of the structure of the C3c-W4A9 complex, and that upon removal of the positive charge by acetylation the hydrophobic cluster was fortified and contributed to the 3-fold increase in activity. To prove this hypothesis, a positive charge was re-introduced in the vicinity at the side chain level by replacing Ile1 by Arg1 in native compstatin (or V4H9 peptide), which resulted to 2-fold decrease in inhibitory activity, essentially reverting the activity to nearly that of non-acetylated compstatin. The peptide with the diserine extension is expected to be active, as the diserine was present at the N-terminus of the original 32-amino acid peptide that was identified in the phage-display and a subsequent study. Preliminary data using ELISA-based complement system inhibition assays with human and rat serum for two of the analogs designed in this study, the R1 and S-1S0 peptides, indicate that in human serum the R1 and S-1S0 analogs have comparable inhibitory activities, which are higher than those of native compstatin and slightly lower than those of the W4A9 analog, thus validating the computational design.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies. Potentially reactive moieties such as amino and carboxyl groups, reactive functional groups, etc., may be protected and subsequently deprotected using various protecting groups and methodologies known in the art. See, e.g., "Protective Groups in Organic Synthesis", 3rd ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation.

A "Peptide" or "Polypeptide", as used herein, refers to a polymer of amino acids, optionally including one or more amino acid analogs. A peptide is a relatively short polypeptide, typically between about 2 and 60 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a peptide/polypeptide may be modified, for example, by the addition of a chemical entity such as a carbohydrate group, a phosphate group, a farnesyl group, an isofarnesyl group, a fatty acid group, a linker for conjugation, functionalization, or other modification. The peptides/polypeptide of the disclosure may be acetylated, e.g., at the N-terminus and/or amidated, e.g., at the C-terminus.

The natural or other chemical modifications such as those described above can occur anywhere in a polypeptide, including the peptide backbone, the amino acid side-chains and the amino or carboxyl termini. A given polypeptide may contain many types of modifications. Peptides/polypeptides may be branched, for example, as a result of ubiquitination, and they may be cyclic, with or without branching. Peptides/polypeptides may be conjugated with, encapsulated by, or embedded within a polymer or polymeric matrix, dendrimer, nanoparticle, microparticle, liposome, or the like.

Peptides/polypeptides may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or methods involving chemical ligation of synthesized peptides (see, e.g., Kent, S., JPeptScL, 9(9): 574-93, 2003), or any combination of the foregoing. These methods are well known, and one of skill in the art will be able to select and implement an appropriate method for synthesizing the peptides and polypeptides described herein.

The term "peptide sequence" or "polypeptide sequence" or "amino acid sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. A polypeptide sequence presented herein is presented in an N-terminal to C-terminal direction unless otherwise indicated.

"Purified", as used herein, means that an entity or substance is separated from one or more other entities or substances with which it was previously found before being purified. An entity or substance may be partially purified, substantially purified, or pure. A substance or entity such as a nucleic acid or polypeptide is considered pure when it is removed from substantially all other compounds or entities other than a solvent and any ions contained in the solvent, i.e., it constitutes at least about 90%, more typically at least about 91%, 92%, 93%, 94%, 95%, 96%, 97%, 98%, 99%, or greater than 99% of the dry weight of the composition. A partially or substantially purified compound or entity such as a nucleic acid or polypeptide may be removed from at least 50%, at least 60%, at least 70%, or at least 80% by weight of the material with which it is naturally found, e.g., cellular material such as cellular proteins and/or nucleic acids. In certain embodiments the of a purified nucleic acid or polypeptide constitutes at least 10%, 20%, 30%, 40%, 50%, 60%, 70%, 80%, 90%, 95%, 99% or even more, by dry weight, of the total nucleic acid or polypeptide, respectively, in a composition. Methods for assessing purity are known in the art and include chromatographic methods, immunological methods, electrophoretic methods, etc. Any of the polynucleotides or polypeptides described herein may be purified.

The term "synthetic" or "non-natural" refers to a compound (e.g., a compstatin analog of the disclosure) (i) is synthesized using a machine, or (ii) that is not derived from a cell or organism that normally produces the compound.

A "subject", as used herein, refers to an individual to whom an agent is to be delivered, e.g., for experimental, diagnostic, and/or therapeutic purposes. Typically subjects are mammals, particularly domesticated mammals (e.g., dogs, cats, etc.), non-human primates, or humans.

The compstatin analogs of the disclosure may be formulated for delivery to a subject, may be conjugated to other compstatin analogs or targeting molecules (e.g., linked to form, for example, a fusion construct), or may be concurrently administered with one or more additional therapeutic agent. The term "linked", when used with respect to two or more moieties, means that the moieties are physically associated or connected with one another to form a molecular structure that is sufficiently stable so that the moieties remain associated under the conditions in which the linkage is formed and, typically, under the conditions in which the new molecular structure is used, e.g., physiological conditions. In certain embodiments of the disclosure the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

In one embodiment, an appropriate binding moiety to which compstatin or a complement inhibiting analog thereof is linked can be any molecule that specifically binds to a target molecule (e.g., polypeptide or a portion thereof). Such a binding moiety is referred to as a "ligand". For example, in various embodiments of the disclosure a ligand can be a polypeptide, peptide, nucleic acid (e.g., DNA or RNA), carbohydrate, lipid or phospholipid, or small molecule (e.g., an organic compound, whether naturally-occurring or artificially created that has relatively low molecular weight and is not a protein, polypeptide, nucleic acid, or lipid, typically with a molecular weight of less than about 1500 g/mol and typically having multiple carbon-carbon bonds). Ligands may be naturally occurring or synthesized. Examples of ligands include, but are not limited to, hormones, growth factors, or neurotransmitters that bind to particular receptors.

"Concurrent administration" as used herein with respect to two or more agents, e.g., therapeutic agents, is administration performed using doses and time intervals such that the administered agents are present together within the body, or at a site of action in the body such as within the eye over a time interval in not less than de minimis quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks), etc. Accordingly, the agents may, but need not be, administered together as part of a single composition. In addition, the agents may, but need not be, administered simultaneously (e.g., within less than 5 minutes, or within less than 1 minute) or within a short time of one another (e.g., less than 1 hour, less than 30 minutes, less than 10 minutes, approximately 5 minutes apart). According to various embodiments of the disclosure agents administered within such time intervals may be considered to be administered at substantially the same time. In certain embodiments of the disclosure concurrently administered agents are present at effective concentrations within the body (e.g., in the blood and/or at a site of action such as the retina) over the time interval. When administered concurrently, the effective concentration of each of the agents needed to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. The de minimis concentration of an agent may be, for example, less than approximately 5% of the concentration that would be required to elicit a particular biological response, e.g., a desired biological response.

An "effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, an effective amount may be an amount sufficient to achieve one or more of the following: (i) inhibit or prevent drusen formation; (ii) cause a reduction in drusen number and/or size (drusen regression); (iii) cause a reduction in or prevent lipofoscin deposits; (iv) inhibit or prevent visual loss or slow the rate of visual loss; (v) inhibit choroidal neovascularization or slow the rate of choroidal neovascularization; (vi) cause a reduction in size and/or number of lesions characterized by choroidal neovascularization; (vii) inhibit choroidal neovascularization or slow the rate of retinal neovascularization; (viii) cause a reduction in size and/or number of lesions characterized by retinal neovascularization; (ix) improve visual acuity and/or contrast sensitivity; (x) inhibit or prevent photoreceptor or RPE cell atrophy or apoptosis, or reduce the rate of photoreceptor or RPE cell atrophy or apoptosis; (xi) inhibit or prevent progression of non-exudative macular degeneration to exudative macular degeneration; (xii) reduce one or more indicia of inflammation, e.g., the presence of inflammation-associated cells such as white blood cells (e.g., neutrophils, macrophages) in the eye, the presence of endogenous inflammatory mediators known in the art, one or more symptoms such as eye pain, redness, light sensitivity, blurred vision and floaters, etc.

"Macular degeneration related condition" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including KPE cells, photoreceptors, and/or capillary endothelial cells. ARMD is the major macular degeneration related condition, but a number of others are known including, but not limited to, Best macular dystrophy, Sorsby fundus dystrophy, Mallatia Leventinese and Doyne honeycomb retinal dystrophy "Local administration" or "local delivery", in reference to delivery of a composition or agent of the disclosure, refers to delivery that does not rely upon transport of the composition or agent to its intended target tissue or site via the vascular system. The composition or agent may be delivered directly to its intended target tissue or site, or in the vicinity thereof, e.g., in close proximity to the intended target tissue or site. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site. It will be understood that once having been locally delivered a fraction of a therapeutic agent (typically only a minor fraction of the administered dose) may enter the vascular system and be transported to another location, including back to its intended target tissue or site.

Suitable preparations, e.g., substantially pure preparations of the compstatin analog or mimetic, or any of the compounds described above, may be combined with pharmaceutically acceptable carriers, diluents, solvents, etc., to produce an appropriate pharmaceutical composition. The disclosure further provides a pharmaceutically acceptable composition comprising (i) a compstatin analog linked to a moiety that binds to a component present on or at the surface of a cell or noncellular molecular entity; and (ii) a pharmaceutically acceptable carrier or vehicle. The moiety may be an antibody or ligand. The component may be a marker such as a cell type specific marker for RPE or endothelial cells, a drusen constituent, and the like.

In certain embodiments of the disclosure the pharmaceutical composition detectably inhibits development or progression of geographic atrophy and/or drusen formation in an eye, following administration to a subject. In other words, administration of the compound measurably reduces development or progression of geographic atrophy and/or drusen formation relative to the expected level in the absence of the composition. In certain embodiments the composition inhibits increase in the retinal thickness (e.g., as measured by OCT) associated with the disease (e.g., the wet type of ARMD). In certain embodiments of the disclosure the pharmaceutical composition detectably inhibits vision loss in an eye, following administration to a subject. In other words, administration of the compound measurably reduces vision loss relative to the expected level in the absence of the composition. In certain embodiments of the disclosure the pharmaceutical composition detectably inhibits inflammation in an eye, following administration to a subject. In other words, administration of the compound measurably reduces inflammation relative to the expected level in the absence of the composition. It is to be understood that the pharmaceutical compositions of the disclosure, when administered to a subject, are preferably administered for a time and in an amount sufficient to treat or prevent the disease or condition for whose treatment or prevention they are administered. A useful pharmaceutical composition may provide one or more than one of the aforementioned beneficial effects.

The disclosure also provides pharmaceutically acceptable compositions comprising a pharmaceutically acceptable derivative (e.g., a prodrug) of compstatin or a complement inhibiting analog thereof, by which is meant any nontoxic salt, ester, salt of an ester or other derivative of a compound of the disclosure that, upon administration to a recipient, is capable of providing, either directly or indirectly, inhibition of the complement cascade.

An effective amount of the pharmaceutical composition is administered to a subject by any suitable route of administration including, but not limited to, intravenous, intramuscular, by inhalation, by catheter, intraocularly, orally, rectally, intradermally, by application to the skin, by eyedrops, etc. When a composition of the disclosure is used to treat an ophthalmic condition it will be appreciated that administration to the eye to or in the vicinity of the eye will typically be used. A compstatin analog may be administered in a solid implant, or in a microparticle or nanoparticle formulation, whereby it is protected from clearance and/or degradation in the bloodstream.

Compositions of the disclosure can be formulated for delivery by any available route including, but not limited to, parenteral, oral, by inhalation to the lungs, nasal, bronchial, ophthalmic, transdermal (topical), transmucosal, rectal, and vaginal routes. The term "parenteral" as used herein includes subcutaneous, intravenous, intramuscular, intra-articular, intra-synovial, intrasternal, intrathecal, intrahepatic, intralesional and intracranial injection or infusion techniques A pharmaceutically acceptable carrier or vehicle refers to a nontoxic carrier or vehicle that does not destroy the pharmacological activity of the compound with which it is formulated. Pharmaceutically acceptable carriers or vehicles that may be used in the compositions of this disclosure include, but are not limited to, water, physiological saline, and the like.

Compositions of the disclosure may include other components as appropriate for the formulation desired, e.g., buffer substances such as phosphates, glycine, sorbic acid, potassium sorbate, partial glyceride mixtures of saturated vegetable fatty acids, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

A pharmaceutically acceptable salt of the compstatin analogs of the disclosure include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the disclosure and their pharmaceutically acceptable acid addition salts.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, dimethyl sulfoxide (DMSO), fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELT™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In general, the composition should be sterile, if possible, and should be fluid so that easy syringability exists.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the compositions are typically delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The disclosure also contemplates delivery of compositions using a nasal spray.

For topical applications, the pharmaceutically acceptable compositions may be formulated in a suitable ointment containing the active component suspended or dissolved in one or more carriers. Carriers for topical administration of the compstatin analogs include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For local delivery to the eye, the pharmaceutically acceptable compositions may be formulated in isotonic, pH adjusted sterile saline or water, either with or without a preservative such as benzylalkonium chloride. Alternatively, for ophthalmic uses, the pharmaceutically acceptable compositions may be formulated in an ointment such as petrolatum or as eyedrops. Methods of local administration to the eye include, e.g., choroidal injection, transscleral injection or placing a scleral patch, selective arterial catheterization, eyedrops or eye ointments, intraocular administration including transretinal, subconjunctival bulbar, intravitreous injection, suprachoroidal injection, subtenon injection, scleral pocket and scleral cutdown injection, by osmotic pump, etc. The agent can also be alternatively administered intravascularly, such as intravenously (IV) or intraarterially. In choroidal injection and scleral patching, the clinician uses a local approach to the eye after initiation of appropriate anesthesia, including painkillers and ophthalmoplegics. A needle containing the therapeutic compound is directed into the subject's choroid or sclera and inserted under sterile conditions. When the needle is properly positioned the compound is injected into either or both of the choroid or sclera. When using either of these methods, the clinician can choose a sustained release or longer acting formulation. Thus, the procedure can be repeated only every several months or several years, depending on the subject's tolerance of the treatment and response.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In addition to the agents described above, the active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. Certain of the materials can also be obtained commercially from Alza Corporation and Nova Pharmaceuticals, Inc. Liposomal suspensions can also be used as pharmaceutically acceptable carriers. These can be prepared according to methods known to those skilled in the art. Liposomes, including targeted liposomes (e.g., antibody targeted liposomes) and pegylated liposomes are known. One of ordinary skill in the art will appreciate that the materials and methods selected for preparation of a controlled release formulation, implant, etc., should be such as to retain activity of the compound. For example, it may be desirable to avoid excessive heating of polypeptides, which could lead to denaturation and loss of activity.

The following examples are intended to illustrate but not limit the disclosure. While they are typical of those that might be used, other procedures known to those skilled in the art may alternatively be used.

EXAMPLES

Example 1

Peptide Development

De Novo Design:
The de novo design focused on the identification of inhibitors against rC3. In its general implementation setup, this protocol has a sequence selection stage and a sequence validation stage. The selection stage employs integer linear optimization to identify amino acid sequences, which correspond to global energy minima of a given (rigid or flexible) template fold. Several structures were used from a simulation of the rC3:W4A9 complex as a structural template. The validation stage computes the approximate binding affinities of these sequences to the target protein, without restricting the conformational space or the binding mode of the complex. For the purposes of the analysis the identification of compstatin analogs with a binding mode similar to the one in the hC3c:W4A9 complex was used. Sequences identified by the second de novo stage underwent detailed atomistic MD simulations in explicit water, which assess the structural behavior and stability of complexes involving the sequences from the selection stage.

Definition of Structural Templates.

The sequence-selection template consisted of a truncated rC3 protein model with residues 329-534 (the compstatin binding site in the hC3:W4A9 complex). This template was based on the simulation system of the rC3:W4A9 complex. To model flexibility, the template was placed into eight distinct conformations, taken at 1-ns intervals from a 7-ns molecular dynamics (MD) simulation of the rC3:W4A9 complex. All conformations were aligned along the structure of the hC3c:W4A9 complex (PDB code: 2QKI); after this alignment, the coordinates of the compstatin variant were extracted from the hC3c:W4A9 complex and combined with each of the rC3 conformations, to create eight distinct rC3:compstatin complexes.

Mutation Sets.

The next step in the selection stage species a list of possible amino acid types for each position in the designed sequence. This mutation set can be general (e.g., all twenty natural amino acids at every position), or restricted by knowledge-based considerations or other criteria, such as the solvent-accessible-surface-area (SASA). Two mutation sets were used in the present design. The first set allowed mutations at positions 1, 3 and 4 of compstatin. The amino acid types at each position were based upon the observed SASA of the corresponding W4A9 residue in the rC3c complex simulations. If a residue of the bound W4A9 was more than 50% exposed to solvent, only hydrophilic amino acids were allowed. If a position was less than 20% exposed, only hydrophobic amino acids were allowed; otherwise, all amino acids were allowed. Based on this criterion, position 1 was allowed to select from a set of hydrophilic amino acids (G, A, P, R, K, D, E, N, Q, H, S, T) and the native amino acid Ile, position 3 was allowed to select from a set of hydrophobic amino acids (A, C, G, V, I, L, M, F, Y, W, T), and position 4 was allowed to select from all amino acids. The small amino acids A, T and G were allowed in all positions. This led to a total of 2860 possible sequences. The second mutation set was based upon results from the first. Of the three positions allowed to mutate in the first set, position 3 showed the least variability, with W being the dominant amino acid (26% probability); other mutations in this position included F (21.4%), M (14.9%), Y (13.5%), I (7.2%), T (5.3%), C (4.1%), V (3.7%), L (3%), A (0.9%). Thus, the second mutation set fixed W at position 3 and allowed the other two positions (1 and 4) to mutate as before. This led to a total of 260 sequences.

Forcefield.

The energy calculations of the selection stage employed the 6-bin Centroid-Centroid force field.

Determination of Low-Energy Sequences.

Because the design template was flexible, the distance bin sequence selection model was used to find low-energy sequences. The model:

$$\min_{y_i^j, y_k^l} \sum_{i=1}^{n-1} \sum_{j=1}^{m_i} \sum_{k=i+1}^{n} \sum_{l=1}^{m_k} \sum_{d:disbin(x_i,x_k,d)=1} E_{ik}^{jl}(x_i, x_k) w_{ik}^{jl} b_{ikd} \quad (1)$$

subject to
$$\sum_{j=1}^{m_i} y_i^j = 1 \forall i$$
$$\sum_{j=1}^{m_i} w_{ik}^{jl} = y_k^l \forall i, k > i, l$$
$$\sum_{l=1}^{m_k} w_{ik}^{jl} = y_i^j \forall i, k > i, j$$
$$\sum_{d:disbin(x_i,x_k,d)=1} b_{ikd} = 1 \forall i, k > i$$

The model minimizes the pair-wise energy $E_{ik}^{jl}$ between amino acid j in position i and amino acid l in position k. The binary variable $w_{ik}^{jl}$ is an interaction variable, and equals the product of the binary variables $y_i^j$ and $y_k^l$. $w_{ik}^{jl}$ equals one only if both $y_i^j$ and $y_k^l$ equal one, indicating that amino acid j is in position i and amino acid l is in position k. The final binary variable $b_{ikd}$ equals one if the distance between position i and position k falls into distance bin d and zero otherwise. In this way, the model is allowed to select one distance bin from among the multiple distance bins that residues i and k may span in the eight MD templates.

Validation Stage.

Selected sequences from the previous stage were subjected to approximate binding affinity calculations. This allowed us to re-rank the sequences from stage one according to approximate binding affinities and identify candidate binders.

The approximate binding affinity of a protein P and peptide L is defined as $$K^* = \frac{q_{PL}}{q_P q_L} \quad (2)$$

where $q_{PL}$, $q_P$, $q_L$ are, respectively, the partition functions of the protein-peptide complex PL, the free protein and the free peptide. These partition functions are defined in Eq. (3), where the sets B, F, and L contain rotameric conformation ensembles of the complex, free protein, and free peptide, respectively:

$$q_{PL} = \sum_{b \in B} e^{-E_b/(RT)}, \; q_P = \sum_{f \in F} e^{-E_f/(RT)}, \; q_L = \sum_{l \in L} e^{-E_l/(RT)} \quad (3)$$

The temperature T entering in the Boltzmann factors of Eq. (3) was set to 298 K. In order to calculate the approximate binding affinity for a mutant sequence, the three-dimensional (3D) structure of each sequence was predicted by the Rosetta ab initio method. A total of 2,000 3D peptide structures were generated. Cluster analysis of their main chain φ and Ψ W torsional angles with OREO determined 11 representative structures of the whole ensemble. Each of these structures was docked to the target protein (the last snapshot of the 7-ns rC3:W4A9 run) using Rosetta Dock. For each docking run, 2,000 docked conformers were generated. The ten lowest-energy conformers were selected as seeds for the complex-ensemble generation using Rosetta Design. Likewise, the ten lowest-energy structures from each of the peptide clusters were selected as seeds for the peptide ensemble generation. For the free protein ensemble, only the crystal structure of the last MD snapshot was selected as the seed. Rosetta Design used these seeds to generate rotamerically-based conformation ensembles (22, 000 for the peptide, 22,000 for the complex, and 2000 for the protein). The energies of each of the members of the ensemble were used to calculate the corresponding partition functions [Eq. (3)] and the approximate binding affinity [Eq. (2)].

Choice of Complexes.

Twenty-two compstatin-based analogs were simulated in complex with human (*Homo sapiens*), rat (*Rattus norvegicus*) and mouse (*Mus musculus*) C3. The analogs were classified into four groups ("generations"). The first generation contained selected promising analogs from the above described de novo design, whereas the other three explored modifications (substitutions or extensions), introduced predominantly at the N-terminal end. The most promising complexes were subjected to more than one run, based on their ability to retain the crystallographic structure and interactions of the hC3c:W4A9 complex, and the magnitude of their association free energies, as quantified by a MM-GB/SA analysis. A comprehensive list of all simulations is included in Table 1.

their most common ionization state at physiological pH. The total charge of the simulation systems was set to zero, by addition of appropriate numbers of chloride anions.

Force Field Specifications.

The peptide atomic charges, van der Waals and stereochemical parameters were taken from the CHARMM22 all-atom force field, including a CMAP backbone $\phi/\psi$ energy correction and indole parameters. All simulations were conducted with the molecular mechanics program CHARMM, versions c35a2, c35b5.

Initial Coordinates.

With the exception of the diserine N-terminal extension in one analog, and protein loop 369-378, the initial positions of all other backbone heavy atoms were taken from the crystallographic structure of the hC3:W4A9 complex (PDB code 2QKI). This avoided introducing any a priori structural differences from the human complex. Loop 369-378 con-

TABLE 1

Summary of simulations conducted in the present work.

| Generation[a] | Run[b] | Analog sequence | Protein species | Run duration (ns) |
|---|---|---|---|---|
| 1 | H1W3Y4:R | Ac-HCWYQDWGAHRCT-NH$_2$ | Rat | 7 |
|   | Q1W3Y4:R1 | Ac-QCWYQDWGAHRCT-NH$_2$ | Rat | 7 |
|   | W3P4:R | Ac-ICWPQDWGAHRCT-NH$_2$ | Rat | 7 |
|   | T1W3F4:R | Ac-TCWFQDWGAHRCT-NH$_2$ | Rat | 7 |
|   | S1W3:R | Ac-SCWWQDWGAHRCT-NH$_2$ | Rat | 7 |
|   | T1W3:R | Ac-TCWWQDWGAHRCT-NH$_2$ | Rat | 7 |
| 2 | R1W3:R1 | Ac-RCWWQDWGAHRCT-NH$_2$ | Rat | 7 |
|   | R1W3:R2 | Ac-RCWWQDWGAHRCT-NH$_2$ | Rat | 7 |
|   | R1:H1 | Ac-RCVWQDWGAHRCT-NH$_2$ | Human | 10 |
|   | R1H2 | Ac-RCVWQDWGAHRCT-NH$_2$ | Human | 7 |
|   | R1:R | Ac-RCVWQDWGAHRCT-NH$_2$ | Rat | 10 |
|   | R1H11:R1 | Ac-RCVWQDWGAHHCT-NH$_2$ | Rat | 7 |
|   | R1K9H11:R1 | Ac-RCVWQDWGKHHCT-NH$_2$ | Rat | 7 |
|   | R1K10H11:R1 | Ac-RCVWQDWGKKHCT-NH$_2$ | Rat | 7 |
| 3 | W1:H1 | Ac-WCVWQDWGAHRCT-NH$_2$ | Human | 10 |
|   | W1:H2 | Ac-WCVWQDWGAHRCT-NH$_2$ | Human | 7 |
|   | W1:R | Ac-WCVWQDWGAHRCT-NH$_2$ | Rat | 10 |
|   | W1:M | Ac-WCVWQDWGAHRCT-NH$_2$ | Mouse | 7 |
|   | W13:H | Ac-ICVWQDWGAHRCW-NH$_2$ | Human | 7 |
|   | W13:M | Ac-ICVWQDWGAHRCW-NH$_2$ | Mouse | 10 |
|   | W1W13:H | Ac-WCVWQDWGAHRCW-NH$_2$ | Human | 7 |
|   | W1W13:M | Ac-WCVWQDWGAHRCW-NH$_2$ | Mouse | 7 |
| 4 | S-1S0:H1 | Ac-SSICVWQDWGAHRTC-NH$_2$ | Human | 10 |
|   | S-1S0:H2 | Ac-SSICVWQDWGAHRTC-NH$_2$ | Human | 10 |
|   | S-1S0:R1 | Ac-SSICVWQDWGAHRTC-NH$_2$ | Rat | 10 |
|   | S-1S0:R2 | Ac-SSICVWQDWGAHRTC-NH$_2$ | Rat | 10 |
|   | S-1S0:M1 | Ac-SSICVWQDWGAHRTC-NH$_2$ | Mouse | 10 |
|   | S-1S0:M2 | Ac-SSICVWQDWGAHRTC-NH$_2$ | Mouse | 10 |
|   | Native compstatin | Ac-ICVVQDWGHHCT-NH$_2$ |  |  |
|   | W4A9 analog: | Ac-ICVWQDWGAHRCT-NH$_2$ |  |  |

[a]The classification into generations is explained in the Methodology section.
[b]Nomenclature: Each substitution, with respect to the parent compound W4A9, is denoted by its one-letter amino acid code and its position; the letter (H/R/M) after the colon ":" denotes the C3 species (human/rat/mouse). A number following this last letter denotes the run number, in case of multiple runs. The diserine extension at the N-terminal end of analogs in generation 4 is denoted as "S-1S0".

Simulation Systems.

All compstatin derivatives were maintained in a cyclic conformation via a Cys2-Cys12 disulfide patch of the CHARMM topology file. Human, rat and mC3 were modeled by the same truncated C3c system. The various complexes were immersed in a box of water molecules in the shape of a 89-Å truncated octahedron; overlapping water molecules were omitted. Titratable residues were assigned tains a deletion at position 372 of the rat and mouse protein (FIG. 4). In non-primate complexes, the initial conformation of this loop was constructed with the program Modeller; its root-mean-square difference (RMSD) from the corresponding conformation in hC3c was 1.39 Å. Heavy atoms of all invariant side chains outside of the 369-378 loop were initially placed at the corresponding coordinates of the human complex; mutated side chains were modeled with the SCWRL4 program. Initial hydrogen positions were determined by the HBUILD algorithm of the CHARMM program.

Simulation Protocols.

To avoid structural deformations at the protein boundary due to the truncation, the main chain heavy atoms of an external protein shell, with atoms at least 20 Å away from any atom of compstatin, were harmonically restrained to their initial crystallographic positions. Segments 373-377 of the reconstructed loop (373-376 in rat and mouse) were also harmonically restrained in all simulations, with the exception of the complexes of generation 4, in which the ligand N-terminal extension (particularly Ser-1) can interact with the loop. The structures were initially optimized by 150 energy minimization steps with the steepest-descent and adopted-basis Newton-Raphson (ABNR) algorithms. This was followed by an equilibration run, consisting of: (i) 30 ps of dynamics, with all protein and ligand heavy atoms harmonically restrained by a force constant of 10 kcal/mol·Å$^2$; (ii) five 50-ps segments, in which the harmonic force constants were gradually lowered to 1.5 kcal/mol·Å$^2$ in the external shell, and to 0 kcal/mol/Å$^2$ elsewhere. The systems were then simulated further, retaining the harmonic-restraint setup from the end of equilibration. The length of this "production run" (7-10 ns) was chosen to ensure that the affinities of the most promising complexes (Table 1) converged to stable values.

TABLE 2

Sequence selection and approximate binding affinity results for inhibitors of rC3 from the second mutation set.

| Name | Rank E | Rank K* | Sequence 1            13 | SEQ ID NO |
|---|---|---|---|---|
| H1W3Y4 | 39 | 1  | HCWYQDWGAHRCT | 56 |
| Q1W3Y4 | 25 | 2  | QCWYQDWGAHRCT | 57 |
| W3P4   | 64 | 3  | ICWPQDWGAHRCT | 58 |
| T1W3F4 | 53 | 4  | TCWFQDWGAHRCT | 59 |
| SQ081  | 81 | 5  | PCWMQDWGAHRCT | 60 |
| S1W3   | 4  | 6  | SCWWQDWGAHRCT | 61 |
| T1W3   | 7  | 7  | TCWWQDWGAHRCT | 62 |
| R1W3   | 3  | 8  | RCWWQDWGAHRCT | 63 |
| SQ001  | 1  | 9  | PCWWQDWGAHRCT | 64 |
| SQ005  | 5  | 10 | HCWWQDWGAHRCT | 65 |
| SQ006  | 6  | 11 | NCWWQDWGAHRCT | 66 |
| SQ002  | 2  | 12 | QCWWQDWGAHRCT | 67 |
| SQ042  | 42 | 13 | HCWFQDWGAHRCT | 68 |
| W4A9   | —  | 14 | ICVWQDWGAHRCT | 69 |
| SQ014  | 14 | 15 | PCWYQDWGAHRCT | 70 |
| SQ019  | 19 | 16 | ICWWQDWGAHRCT | 71 |
| SQ080  | 80 | 17 | PCWHQDWGAHRCT | 72 |
| SQ008  | 8  | 18 | PCWPQDWGAHRCT | 73 |

Rankings are given for sequence selection (lowest energy-rank = 1, E) and approximate binding affinity (highest affinity-rank = 1, K*).
Mutations (with respect to W4A9) are indicated in bold face.

Initial Conformation of the Diserine N-Terminal End Extension.

One of the simulated analogs (S-1S0, corresponding to the fourth generation) contained a two-serine N-terminal extension, combined with the W4A9 sequence. The initial conformation of the extension was optimized as follows. At first, the analog was extended by two alanine residues. To construct initial conformations of the dialanine, its four main chain torsional angles were varied in the range −180° to 180, using a grid of 30°. The initial conformations of atoms outside the extension were prepared as described above, for human and rat complexes; for the mouse complex, they were positioned to the coordinates of a low-affinity structure from the W4A9:rC3 simulations. For each of the resulting dialanine conformations, the entire complex was minimized by 100 steepest-descent minimization steps; during this minimization, atoms outside the dialanine extension were harmonically restrained by 100 kcal/mol/A$^2$. The lowest-energy conformation was finally selected as the optimum structure of the extension. The alanine side chains were replaced by serines, and their optimum orientations were determined by the program SCWRL4.

Analysis of Side-Chain Contacts.

Probability-density maps of intermolecular side-chain contacts were computed with the WORDOM package. Two side-chains were considered in contact if the distance of their geometric centers was smaller than 6.5 Å.

Computation of Association Free Energies.

The association free energies (second column in Table 3) were computed by the relation $$\Delta G = G_{PL} - G_P - G_L \quad (4)$$

where PL, P and L denote, respectively, the complex, protein, and ligand. The individual free energies were computed in the Molecular Mechanics-Generalized Born/Surface Area (MM-GB/SA) approximation. In this approximation, representative coordinates of each state X (X=PL, P, or L) are extracted from the corresponding simulation trajectories. The corresponding free energies are computed from the relation.

$$G_X = E_X^{bonded} + \underbrace{E_X^{Coul} + E_X^{GB}}_{=G_X^{polar}} + \underbrace{E_X^{vW} + \sigma S_X}_{=G_X^{non\,polar}} \quad (5)$$

The first term on the right-hand side of Eq. (5) describes the dependence of the internal energy on the molecular geometry (bond lengths, bond angles, torsional angles); the second term describes Coulombic interaction energies between the atomic charges of the molecule; the third term represents the electrostatic contribution to the solvation free energy, and is modeled by the GBSW generalized-Born approximation. The next term describes van der Waals interactions; the final term describes non-polar contributions to the solvation free energy, assumed proportional to the solvent-accessible surface area, $S_x$, of the molecule. The proportionality coefficient σ was set to 0.005 kcal/mol/Å$^2$, as in the GBSW parameterization. Note that for the complexes studied here, the contribution from this last term to the obtained affinities was approximately constant among complexes; thus, the value used for σ affects the individual but not the relative association free energies.

TABLE 3

Association free energies of selected complexes (in kcal/mol). A complete list of association free energies for the remaining complexes of Table 1 is given in Table 6.

| Run | Binding Free Energy | | | | | | | |
|---|---|---|---|---|---|---|---|---|
| | Total | Std Dev | Polar Component[a] | Std Dev | Non-polar Component[a] | Std Dev | Polar Interaction[b] | Std Dev |
| R1:H1 | −58.3 | 0.6 | 0.4 | 0.6 | −58.8 | 1.2 | −65.2 | 0.7 |
| R1:H2 | −60.2 | 2.3 | −1.1 | 1.9 | −59.1 | 0.4 | −71.0 | 0.1 |
| Average | −59.3 | 1.9 | −0.3 | 1.6 | −58.9 | 0.9 | −68.1 | 2.9 |
| W1:H1 | −56.8 | 1.1 | 3.4 | 0.1 | −60.2 | 1.2 | −51.0 | 1.5 |
| W1:H2 | −54.6 | 0.1 | 6.0 | 0.6 | −60.6 | 0.8 | −46.8 | 0.9 |
| Average | −55.7 | 1.4 | 4.7 | 1.4 | −60.4 | 1.0 | −48.9 | 2.4 |
| S-1S0:H1 | −58.8 | 0.0 | 1.1 | 0.3 | −59.9 | 0.2 | −47.8 | 4.1 |
| S-1S0:H2 | −55.7 | 0.1 | 6.4 | 0.3 | −62.2 | 0.4 | −32.0 | 0.5 |
| Average | −57.3 | 1.6 | 3.8 | 2.7 | −61.0 | 1.2 | −39.9 | 8.4 |
| S-1S0:R1 | −55.7 | 0.8 | 3.4 | 0.5 | −59.0 | 0.3 | −47.1 | 0.5 |
| S-1S0:R2 | −53.9 | 1.7 | 3.4 | 0.6 | −57.3 | 1.1 | −45.4 | 1.4 |
| Average | −54.8 | 1.6 | 3.4 | 0.5 | −58.2 | 1.2 | −46.2 | 1.4 |
| S-1S0:M1 | −54.4 | 0.0 | 4.8 | 0.2 | −59.2 | 0.2 | −45.3 | 0.9 |
| S-1S0:M2 | −59.0 | 0.0 | 4.8 | 0.2 | −63.8 | 0.2 | −46.5 | 0.8 |
| Average | −56.7 | 2.3 | 4.8 | 0.2 | −61.5 | 2.3 | −45.9 | 1.1 |

Values are averaged over 700 snapshots (last 7-ns of each run).
[a]Computed with Eq. (1), assuming identical protein and ligand conformations in the complex and dissociated states (see Methods).
[b]Defined in Eq. (2).
[b]The polar-interaction components [Eq. (3)] measure the strength of intermolecular polar (Coulomb and GB) interactions in the complexes.

In the application of Eq. (4) the "one-trajectory" approximation is made, which assumes that the protein and ligand have identical structures in the complex and free (dissociated) states. This assumption ignores structural relaxation, which might contribute a few kcal/mol to relative affinities. On the other hand, it also eliminates contributions from intramolecular (bonded, intramolecular van der Waals and intramolecular Coulomb energies, which contribute thousands of kcal/mol to the energies of the complex and free protein [Eq. (5)], and may introduce large uncertainties in the relative affinities; in the "one-trajectory approximation" these contributions cancel out in the association free energies [Eq. (4)].

The MM-GB/SA approximation and the related Molecular Mechanics/Poisson Boltzmann Surface Area (MM-PBSA) approximation have been extensively used in affinity estimates. Their performance is fragile, as they are based on numerous assumptions: they combine a molecular mechanics energy function with an implicit treatment of solvation effects, and include solute conformational entropy effects in an approximate manner. For W4A9 a +9 kcal/mol relative affinity disfavoring rC3 over hC3 was obtained. This estimate has the correct sign, since W4A9 is experimentally inactive against rC3; in fact, it is probably a lower bound to the relative affinity, since a "three-trajectory" approximation increases the value to ~+19 kcal/mol. Thus, relative affinities of this magnitude (~+10 kcal/mol) are indicative of ligands specific for human (vs non-primate) C3.

The interaction energies between two groups of atoms (R and R') (were computed by the relation.

$$\Delta G_{RR'}^{inte} \sum_{i \in R} \sum_{j \in R'} \underbrace{(E_{ij}^{Coul} + E_{ij}^{GB})}_{\Delta G_{RR'}^{polar}} + \underbrace{\sum_{i \in R} \sum_{j \in R'} E_{ij}^{vW} + \sigma \sum_{i \in R,R'} \Delta S_i}_{\Delta G_{RR'}^{non\ polar}} \quad (6)$$

The first and second group of terms on the right-hand side of Eq. (6) describe, respectively, polar and nonpolar interactions between R and R'; in the calculations, R corresponded to a ligand residue and R' to the entire protein model; alternatively, R was a protein residue and R' was the entire ligand. To compute the GB term in Eq. (6), all protein and ligand atoms were included and the charges of atoms outside the two groups R and R' to zero. The last term contains the difference in solvent accessible surface areas of groups R and R' in the complex and unbound states.

The generalized-Born energies and the atomic accessible-surface areas ($\Delta S_i$) entering in Eq. (6) depend on the location of R and R' in the complex. The polar component contains a Coulombic term and a GB contribution, modeling the interaction between group R and the solvent polarization potential induced by R'. Similarly, the nonpolar component contains a van der Waals interaction between R, R' and a surface term, expressing cavity contributions and nonpolar interactions with the surrounding solvent. The sum of the two components reflects the total direct interaction between R and R' in the solvated complex.

Free-energy values were averaged over the last 7 ns of each trajectory; to estimate the free-energy uncertainties, these 7 ns were partitioned into two blocks of 3.5 ns, and computed the standard deviation of averages over the 3.5-ns segments.

De Novo Design Results.

The sequence-selection stage employed two mutation sets at positions 1, 3 and 4. The first mutation set generated 1,000 sequences; 26% of all the sequences and 48% of the top 500 sequences had a W substitution at position 3. This prompted the use of a second set, in which position 3 was fixed to W. All 260 sequences of the second set were generated, and the top quarter with respect to energy was analyzed. Position 4 had a dominance of F or W (19% each), while position 1 was more variable, favoring H, N, F, Q, R, S, or T (10% each). Seventeen sequences were selected from the second mutation set for the validation step. These included: (i) the best 8 sequences with respect to their energy (E-) rank, the seven top sequences contained a W substitution at position 4, and a variety of substitutions at position 1; and (ii) 9 more sequences, combining a non-W substitution at position 4 together with residues at position 1 encountered in the best 8 sequences (Table 2). The approximate binding affinities of all sequences were computed as described above, together with the W4A9 compound (V4W/H9A). The results are summarized in Table 2. For each sequence, the E-rank and an approximate binding affinity (K*-) rank are given. Sequences with small values of E-ranks had low-energies in stage 1; sequences with small values of K*-ranks were predicted to have high-affinities in the second stage.

Several sequences have higher approximate binding affinity than W4A9, the best inhibitor of hC3 comprising entirely of natural amino acids. The top two sequences (in terms of affinity-rank) have an aromatic residue at position 4 and differ only at position 1. The top five sequences also have high energy-ranks. In general, there is no strict correlation between energy- and affinity-rank throughout the set. This is partly due to the fact that the energies are computed from the selection stage, which assumes that the ligand binding mode (location/orientation) is similar to the one in the hC3c: W4A9 complex; on the other hand, affinities are computed in the validation stage by a more general docking procedure, in which the free protein, free ligand and the protein-ligand complex are allowed to explore a larger number of conformations and binding modes. This expanded search uncovers a more diverse set of binding modes, which change the predicted relative stability of the various complexes summarized in Table 2.

Molecular Dynamics Simulations.

The structure and interactions of the complex between W4A9 and hC3 were analyzed by X-ray crystallography and MD simulations.

The Human Complex with W4A9.

Figure 1C:
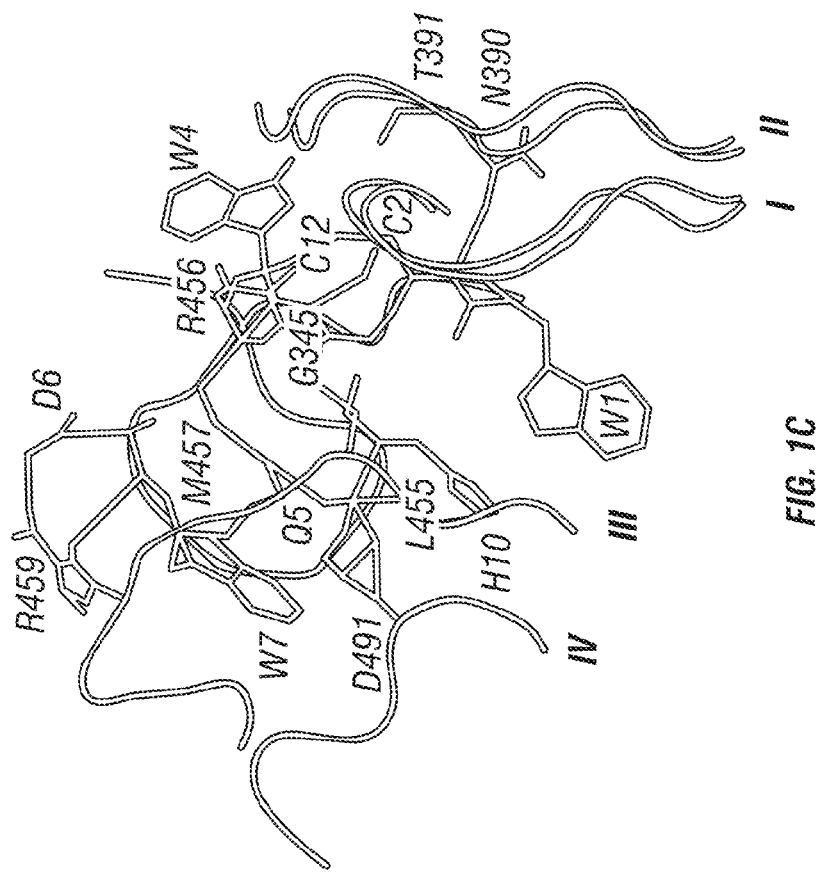
Figure 3A:
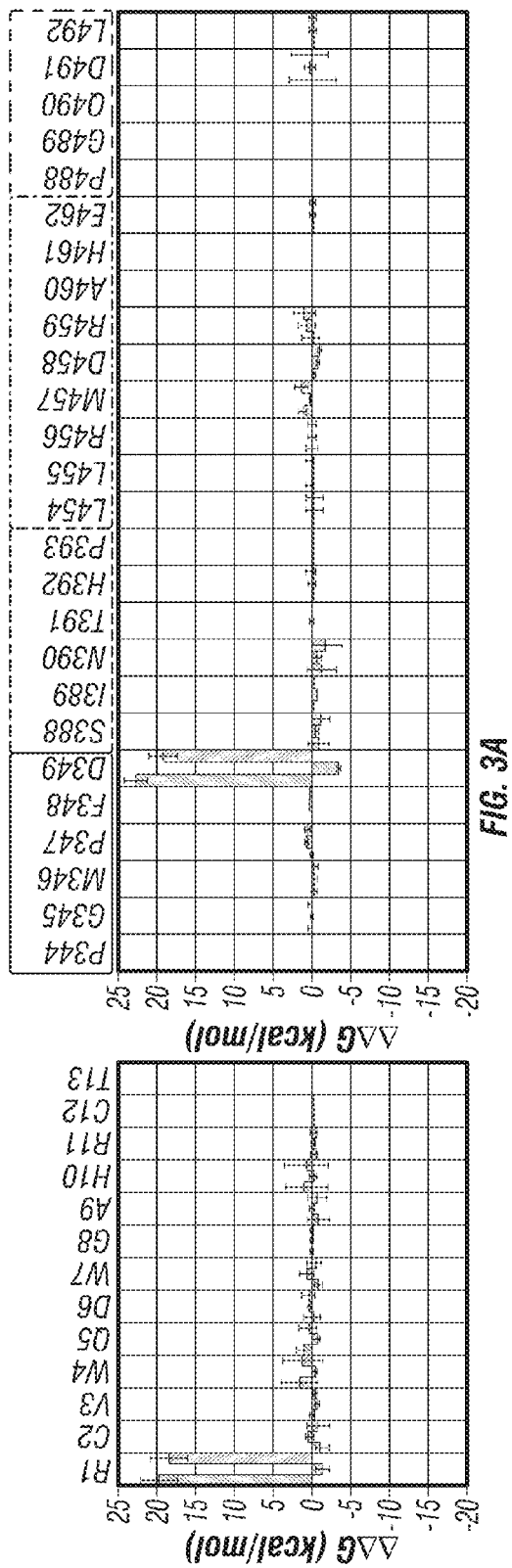
FIG. 3A-C shows residue intermolecular interaction energy differences between the complex W4A9:hC3 and selected compstatin simulations of the disclosure. Compstatin and C3 results are shown in the left and right panel. Data are averaged over all respective runs. The uncertainties (error bars) are computed as described below. (A) W4A9:hC3-R1:H difference; (B) W4A9:hC3-W1:H difference; (C) W4A9:hC3-S-1S0:H difference. Positive/negative values indicate, respectively, gained/lost interactions in the new complexes, relative to the W4A9:hC3 complex. C3 regions interacting with compstatin analogs are enclosed in boxes in (A) and (C), grey-scaled as follows: sector 344-349; sector 371-376; sector 388-393; sector 454-462; and sector 488-492.
Figure 3B:
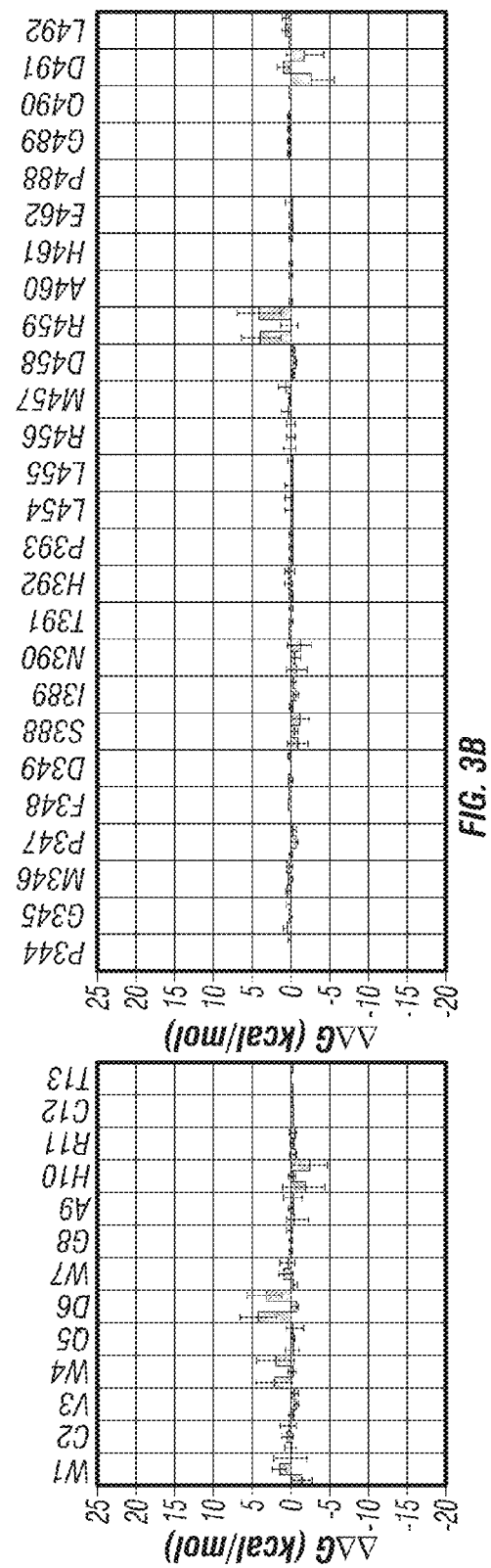
Figure 3C:
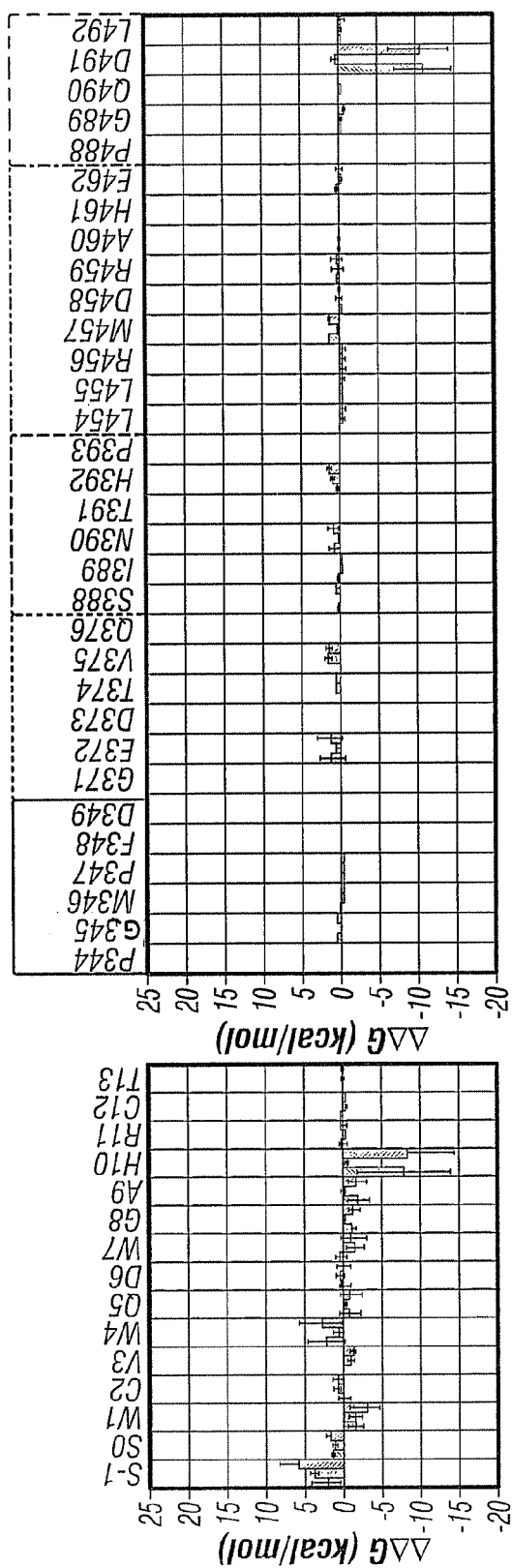

In the crystal structure (PDB code 2QKI) and the MD simulations, the ligand segment 1-10 forms extensive interactions with the four protein sectors 344-349, 388-393, 454-462, and 488-492. These interactions are preserved in the R1 and W1 complexes (runs: R1:H1, W1:H1) and are shown in FIG. 1(A-D). The main chain moieties of N-terminal residues Ile1 and Cys2 make competing hydrogen bonds with the Asn390 side chain. The Val3 side chain is buried in a very stable hydrophobic cluster formed by residues Met346, Pro347 and Leu454. The Trp4 main chain participates in stable hydrogen bonds with Gly345 CO and the side chain of Arg456; the Trp4 side chain packs against the Cys2-Cys12 disulfide-bridge and residue Pro393. The Gln5 side chain makes two intermolecular hydrogen bonds with main chain groups of Leu455 and Met457. The Trp7 side chain intercalates between segments 455-458 and 488-491, making a stable hydrogen bond with Met457 CO and non-polar contacts with Gln5, Met457, Arg459, and Glu462. Finally, the main chain NH groups of Ala9 and His10 form very stable hydrogen bonds with the Asp491 side chain; an additional hydrogen-bond is often observed among the side chain of His10 and Asp491; also, the His10 side chain makes frequent non-polar contacts with Leu454 and Leu492.

Choice of Analogs.

The de novo design identified a number of sequences capable of forming good interactions with the structural template. Promising sequences were selected by atomistic MD simulations. In particular, the ability of the designed analogs to bind non-primate (rat or mouse) C3 were investigated, with a similar "binding mode" (location/orientation) to the one in the W4A9:hC3 complex; such analogs are likely to inhibit C3 by interfering with the formation of the C3:C3-convertase complex in a manner analogous to W4A9, and thus constitute promising rC3 inhibitors. The possibility that successful inhibitors might bind preferentially at different positions on non-primate (and/or human) C3 cannot be excluded; the systematic and accurate comparison of such diverse binding modes by atomistic MD simulations is very difficult, given the size of C3.

Four "generations" of compstatin-based compounds were studied in complex with human or non-primate C3. All simulations are summarized in Table 1.

The first generation included six compounds (H1W3Y4, Q1W3Y4, W3P4, T1W3F4, S1W3, T1W3). These analogs had high-affinity ranks in the de novo sequence selection stage (Table 2); the first four had also large energy ranks. All analogs had significant variability at position 1. Earlier simulations showed that key interactions between compstatin N-terminal residues 1 or 2 and the Asn390 side chain were lost in the rat complex, due to the displacement of sector 388-393 away from the ligand. It was thus deemed probable that the insertion of bulky or hydrogen-bonding side chains at position 1 might restore interactions with Asn390 in the rat complex. This was not fully accomplished in the simulations of this generation, but was pursued further in the analogs of the next three generations, which contained, respectively, charged or aromatic substitutions at position 1, or a diserine extension before residue 1. Sequences with a Pro substitution at position 1 were also suggested by the design.

The second generation contained analogs with an Arg substitution (in place of Ile) at position 1. The parent analog (R1W3) resulted from the de novo design (Table 1). In the MD simulations the Arg1 side-chain formed a salt-bridge with proximal residue Asp349, which improved the computed affinity for rC3. In an attempt to improve affinity even further, additional polar or charged substitutions at positions 9-11 were also explored (analogs R1H11, R1K9H11 and R1K10H11). The analogs were simulated in complex with rat and/or hC3, to assess the impact of these substitutions across species.

The third generation included analogs with Trp substitutions at positions 1 and/or 13, suggested by de novo design of inhibitors against hC3. Subsequent activity measurements showed that analog W1 had near-W4A9 inhibitory activity against hC3, whereas analogs W13 and W1W13 had slightly reduced activities and solubilities, which may be connected. In the experimental structure and the MD simulations of the W4A9:hC3 complex, the (native) Ile1 side chain forms weak nonpolar contacts with the protein and the Thr13 side chain is exposed to solvent. Thus, the Trp1/Trp13 substitutions introduce a capability for new interactions (aromatic, n-cation, n-stacking or hydrogen bonding) at the N- and C-terminal positions. Such interactions may improve hC3 inhibition, and/or introduce inhibitory activity against non-primate C3. To check this possibility, and compare ligand affinities across species, studies were performed of the complexes of such analogs with human, rat and mC3.

The analogs considered so far contain 13 residues. The last generation included one analog, with a diserine extension at the N-terminal end (positions "−1", "0"), and the W4A9 sequence at positions 1-13. These analogs were inspired by our simulations and the present results with human and rat/mouse complexes, which showed that sector 388-393 of non-primate proteins has a persistent tendency to deviate from the position seen in the human crystallographic complex. This structural reorganization disrupts hydrogen-bonding interactions of Asn390 and the main chain of the first two N-terminal residues (Ile1 and Cys2 in W4A9), and weakens the affinity of the rat and mouse—compstatin complexes. Based on this knowledge, it was reasoned that an elongation of the compstatin main chain at the N-terminal end might help retain hydrogen-bonding interactions with the displaced protein sector, and yield compstatin analogs with human-like affinity for non-primate C3. As a first attempt, serine side chains were used in the extension, due to their hydrogen-bonding capacity.

Structural Behavior of the Simulated Complexes.

Root-mean-square differences (RMSD) between the simulation and crystallographic coordinates of protein and ligand main chain atoms N $C_\alpha$, C are listed in Table 4. The first two rows report the RMSD values for the two runs of the human complex W4A9:hC3.

TABLE 4

Root Mean Square Difference (RMSD) between the conformations of the simulated complexes and the crystal structure of the human C3c:W4A9 complex (all values in Å).

| | C3c | | 344-349 Sector[a] | | 388-393 Sector[a] | | 454-462 Sector[a] | | 488-492 Sector[a] | | Compstatin | | | |
|---|---|---|---|---|---|---|---|---|---|---|---|---|---|---|
| | | | | | | | | | | | No alignment | | Alignment | |
| Run | 1 ns[c] | 7 ns[d] | 1 ns[c] | 7 ns[d] | 1 ns[c] | 7 ns[d] | 1 ns[c] | 7 ns[d] | 1 ns[c] | 7 ns[d] | 1 ns[c] | 7 ns[d] | 1 ns[c] | 7 ns[d] |
| H1[e] | 0.90 | 0.90 | 0.93 | 0.95 | 1.04 | 0.90 | 1.15 | 1.09 | 1.09 | 1.23 | 1.73 | 1.57 | 1.01 | 0.85 |
| H2[e] | 0.71 | 0.70 | 0.86 | 0.77 | 0.99 | 0.97 | 0.80 | 0.87 | 0.64 | 0.72 | 1.80 | 1.60 | 1.20 | 0.90 |
| Generation 1 | | | | | | | | | | | | | | |
| H1W3Y4:R | 1.06 | 0.98 | 1.42 | 1.29 | 2.74 | 2.28 | 1.13 | 1.23 | 1.28 | 1.18 | 3.16 | 2.94 | 1.25 | 1.05 |
| Q1W3Y4:R1 | 0.91 | 0.84 | 1.11 | 1.04 | 1.29 | 1.21 | 0.97 | 0.95 | 1.44 | 1.18 | 3.24 | 2.85 | 1.55 | 1.46 |
| Q1W3Y4:R2 | 0.97 | 0.87 | 1.11 | 1.22 | 1.71 | 1.64 | 1.25 | 1.10 | 1.69 | 1.14 | 7.42 | 6.83 | 1.22 | 1.19 |
| W3P4:R | 0.89 | 0.93 | 0.88 | 1.20 | 1.48 | 1.77 | 0.97 | 1.07 | 1.73 | 1.42 | 5.39 | 3.46 | 2.23 | 1.39 |
| T1W3F4:R | 0.98 | 0.97 | 0.86 | 0.96 | 1.58 | 1.72 | 1.00 | 1.05 | 1.38 | 1.27 | 4.98 | 3.76 | 1.39 | 1.39 |
| S1W3:R | 0.94 | 0.89 | 1.18 | 1.23 | 1.92 | 1.75 | 1.12 | 1.01 | 1.90 | 1.39 | 3.95 | 4.07 | 1.43 | 1.32 |
| T1W3:R | 1.07 | 0.95 | 1.77 | 1.55 | 2.22 | 2.05 | 1.16 | 1.03 | 1.41 | 1.03 | 5.84 | 4.94 | 2.44 | 1.89 |
| Generation 2 | | | | | | | | | | | | | | |
| R1W3:R1 | 1.05 | 0.96 | 1.92 | 1.97 | 2.10 | 2.01 | 1.05 | 0.93 | 0.91 | 0.92 | 2.75 | 2.49 | 1.13 | 0.94 |
| R1W3:R2 | 0.91 | 0.93 | 1.93 | 1.98 | 1.63 | 1.78 | 1.02 | 1.13 | 1.20 | 1.18 | 2.86 | 2.82 | 0.95 | 1.03 |
| R1:H1 | 0.80 | 0.81 | 1.07 | 1.21 | 0.97 | 0.98 | 1.19 | 1.17 | 0.79 | 0.84 | 2.28 | 2.07 | 0.99 | 0.82 |
| R1:H2 | 0.73 | 0.75 | 0.60 | 0.81 | 0.89 | 0.93 | 0.92 | 0.96 | 0.69 | 0.76 | 1.86 | 1.79 | 1.20 | 1.05 |
| R1:R | 0.95 | 0.84 | 1.22 | 0.99 | 1.77 | 1.48 | 1.11 | 1.06 | 1.25 | 1.13 | 2.30 | 2.03 | 0.80 | 0.84 |
| R1H11:R1 | 0.95 | 0.88 | 1.61 | 1.48 | 2.25 | 1.96 | 0.82 | 0.84 | 1.04 | 0.79 | 3.81 | 3.16 | 1.40 | 1.38 |
| R1H11:R2 | 0.90 | 0.89 | 1.57 | 1.30 | 2.13 | 2.03 | 0.92 | 0.96 | 0.83 | 0.93 | 3.68 | 2.92 | 1.42 | 1.27 |
| R1K9H11:R1 | 0.89 | 0.88 | 1.35 | 1.41 | 2.05 | 1.94 | 0.90 | 0.86 | 0.86 | 0.83 | 2.52 | 2.48 | 1.24 | 1.10 |
| R1K9H11:R2 | 0.82 | 0.85 | 1.04 | 1.15 | 1.38 | 1.34 | 0.76 | 0.95 | 0.79 | 0.89 | 2.70 | 2.57 | 1.62 | 1.44 |
| R1K10H11:R1 | 0.85 | 0.89 | 1.05 | 1.18 | 1.96 | 1.96 | 0.99 | 1.11 | 0.86 | 0.94 | 2.94 | 3.12 | 1.68 | 1.75 |
| R1K10H11:R2 | 1.12 | 1.03 | 1.39 | 1.37 | 2.32 | 2.02 | 1.23 | 1.19 | 2.79 | 1.78 | 3.75 | 2.93 | 1.40 | 1.20 |
| Generation 3 | | | | | | | | | | | | | | |
| W1:H1 | 0.86 | 0.82 | 0.97 | 0.92 | 1.25 | 1.05 | 1.07 | 1.06 | 1.11 | 0.92 | 2.37 | 2.13 | 1.43 | 1.29 |
| W1:H2 | 0.79 | 0.78 | 1.07 | 1.02 | 1.04 | 1.08 | 1.24 | 1.09 | 0.88 | 0.83 | 2.25 | 1.81 | 0.96 | 0.93 |
| W1:R | 0.92 | 0.87 | 1.09 | 1.15 | 2.04 | 1.82 | 1.04 | 0.94 | 1.96 | 1.39 | 2.55 | 2.56 | 0.90 | 1.00 |
| W1:M | 0.90 | 0.89 | 0.99 | 1.10 | 1.46 | 1.58 | 0.96 | 1.00 | 1.34 | 1.28 | 1.44 | 1.51 | 0.80 | 0.80 |
| W13:H | 0.85 | 0.83 | 1.24 | 1.18 | 1.31 | 1.31 | 1.08 | 0.95 | 0.86 | 0.90 | 2.83 | 2.20 | 1.35 | 1.08 |
| W13:M | 0.96 | 0.91 | 0.93 | 1.13 | 2.01 | 1.90 | 1.07 | 1.14 | 1.18 | 0.92 | 1.85 | 2.17 | 1.27 | 0.94 |
| W1W13:H | 0.78 | 0.75 | 1.02 | 1.01 | 0.97 | 1.10 | 0.78 | 0.92 | 0.68 | 0.71 | 1.51 | 1.59 | 0.81 | 0.83 |
| W1W13:M | 0.99 | 0.93 | 1.66 | 1.12 | 1.73 | 1.76 | 0.98 | 0.99 | 1.26 | 1.12 | 1.63 | 1.87 | 0.72 | 0.96 |
| Generation 4 | | | | | | | | | | | | | | |
| S-1S0:H1[e] | 0.87 | 0.87 | 0.68 | 0.70 | 0.84 | 0.90 | 1.24 | 1.17 | 1.38 | 1.25 | 2.40 | 1.91 | 1.41 | 1.02 |
| S-1S0:H2[e] | 0.97 | 0.92 | 0.82 | 0.85 | 1.05 | 1.14 | 1.03 | 1.00 | 1.24 | 1.04 | 2.60 | 2.76 | 1.46 | 1.43 |
| S-1S0:R1[e] | 0.92 | 0.93 | 1.12 | 1.09 | 1.38 | 1.44 | 1.06 | 1.12 | 1.00 | 1.04 | 2.42 | 2.45 | 1.58 | 1.45 |
| S-1S0:R2[e] | 0.94 | 0.94 | 1.40 | 1.25 | 1.44 | 1.34 | 1.43 | 1.31 | 0.98 | 1.08 | 2.34 | 2.46 | 1.43 | 1.49 |
| S-1S0:M1[e] | 1.03 | 1.03 | 1.11 | 1.08 | 1.72 | 1.53 | 1.38 | 1.30 | 0.79 | 0.85 | 2.75 | 2.54 | 1.55 | 1.48 |
| S-1S0:M2[e] | 0.98 | 1.00 | 1.04 | 1.05 | 1.56 | 1.68 | 1.46 | 1.37 | 0.81 | 0.85 | 2.56 | 2.50 | 1.54 | 1.48 |

The protein and ligand main-chain atoms (N, Cα, C) are used in the RMSD calculation, without any rotation or translation (with the exception of the last column).
[a]Atoms in the four listed sectors are within 7 Å from compstatin in human C3c:W4A9.
[b]RMSD values after alignment with respect to the experimental conformation.
[c-d]Averages over the last 1 or 7 ns, respectively.
[e]Simulations of the human C3c:W4A9 complex.
[f]RMSD values are evaluated for segment 1-13.

The protein main chain (second column) remains near the crystallographic conformation in all complexes, as indicated by the small RMSD values (below or near 1 Å); the original secondary structure is also well retained. Sector 388-393 has the largest deviation in all rC3 and mC3 complexes studied here, due to its tendency to move away from the conformation seen in the human complex and towards the solvent. An example is shown in FIG. 1(E), where the 388-393 conformation at the end of run S-1S0:R1 is juxtaposed to the initial conformation. This behavior was first observed in the simulations of the W4A9:rC3 complex, and is consistently reproducible. The fragment 388-396 contains four substitutions in rC3 and mC3 (Pro392His, Asn393Pro, Arg395Gln and Gln396Lys; an alignment of human, mouse and rat sequences is shown in FIG. 4). Unpublished simulations show that the insertion of human substitutions in all four positions of mC3 reduces the structural deviation of 388-393 at the level of the human complex.

In some rat or mouse complexes, sector 345-349 also experiences larger structural deviations relative to the human complexes. This is partly related to the presence of an Ala residue (instead of Gly) at position 345, which alters somewhat the main chain conformation and affects the formation of a hydrogen-bond between the main chain amide group of ligand residue 4 and the carbonyl group of Gly/Ala345. Deviations in the other two sectors (354-359, 488-493) are similar to the ones in the human complexes.

Figure 5:
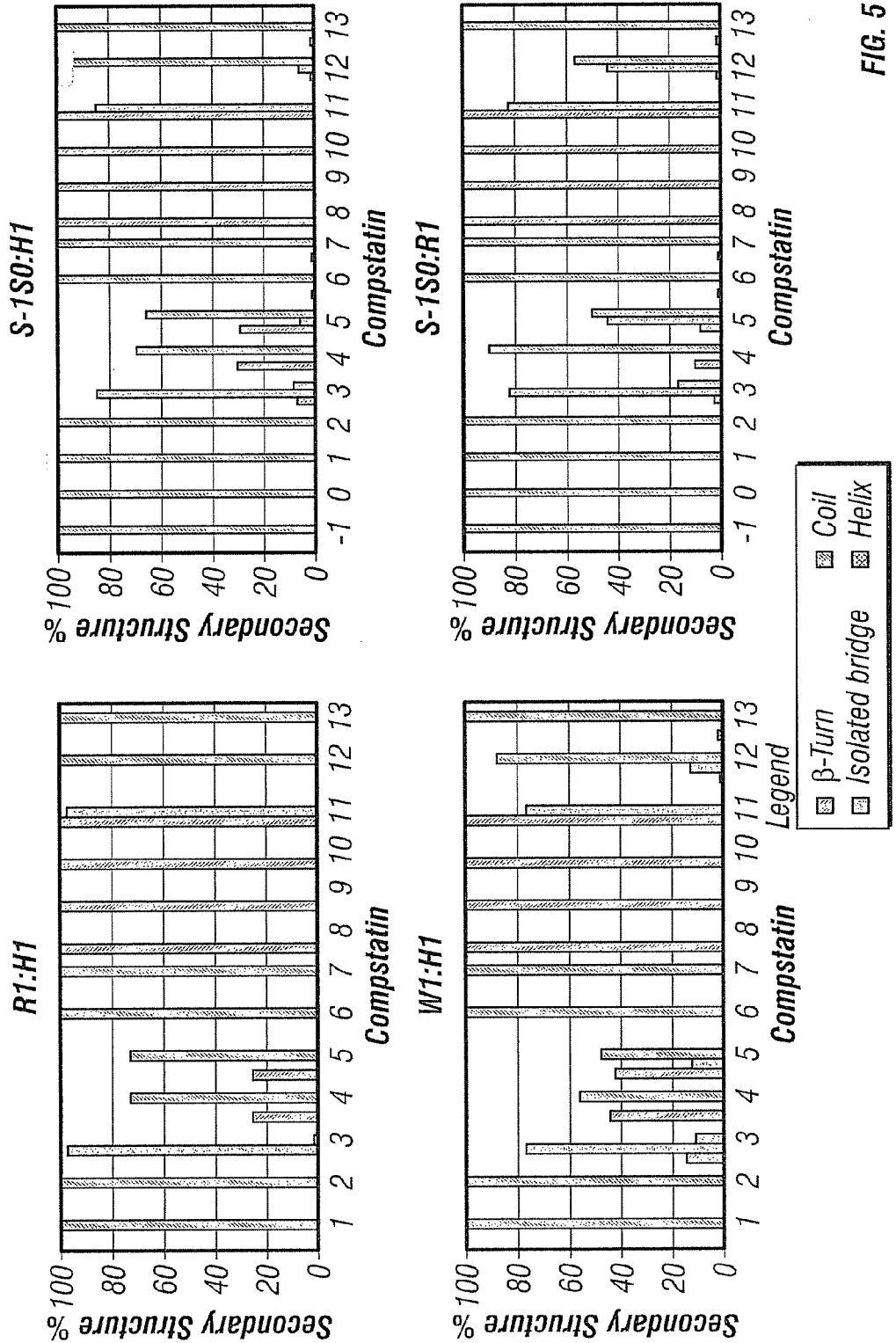
FIG. 5 shows residue secondary structure probability (%) profiles for selected analogs (legend at the bottom right). From top right to bottom left: In R1:H1, the intramolecular (β-bridge 2-12 is conserved; In W1:H1, the bridge is interchanged between residues 3-11 and 5-12; W1:R shows the β-bridge in a non-primate complex; In R1K10H11:R1, the β-bridge is lost; In diserine analogs (S-1S0:H, S-1S0:R and S-1S0:M) the β-bridge can be interchanged between residues 3-11 and 5-12.

The displacement of 388-393 in non-primate complexes facilitates the deviation of the ligand away from the original binding mode (position/orientation). This is reflected in the larger ligand RMSD values (next-to-last column of Table 4), especially in the non-primate complexes of generation 1. The diserine extension also affects the binding mode, presumably due to the formation of interactions with 388-393 and the flexible loop 371-376, which is also near the extension. The larger ligand RMSD values are mainly due to shifts/rotations with respect to the original bound location, rather than due to changes in the ligand shape; upon removing the ligand net rotation/translation, they become comparable to the RMSD values of the human runs (last column of Table 4). Furthermore, the ligand maintains its secondary structure in all complexes, with the exception of an intramolecular S-bridge 3-11, which is not well preserved in the non-primate complexes (FIG. 5).

Protein—Ligand Interactions.

Figure 6:
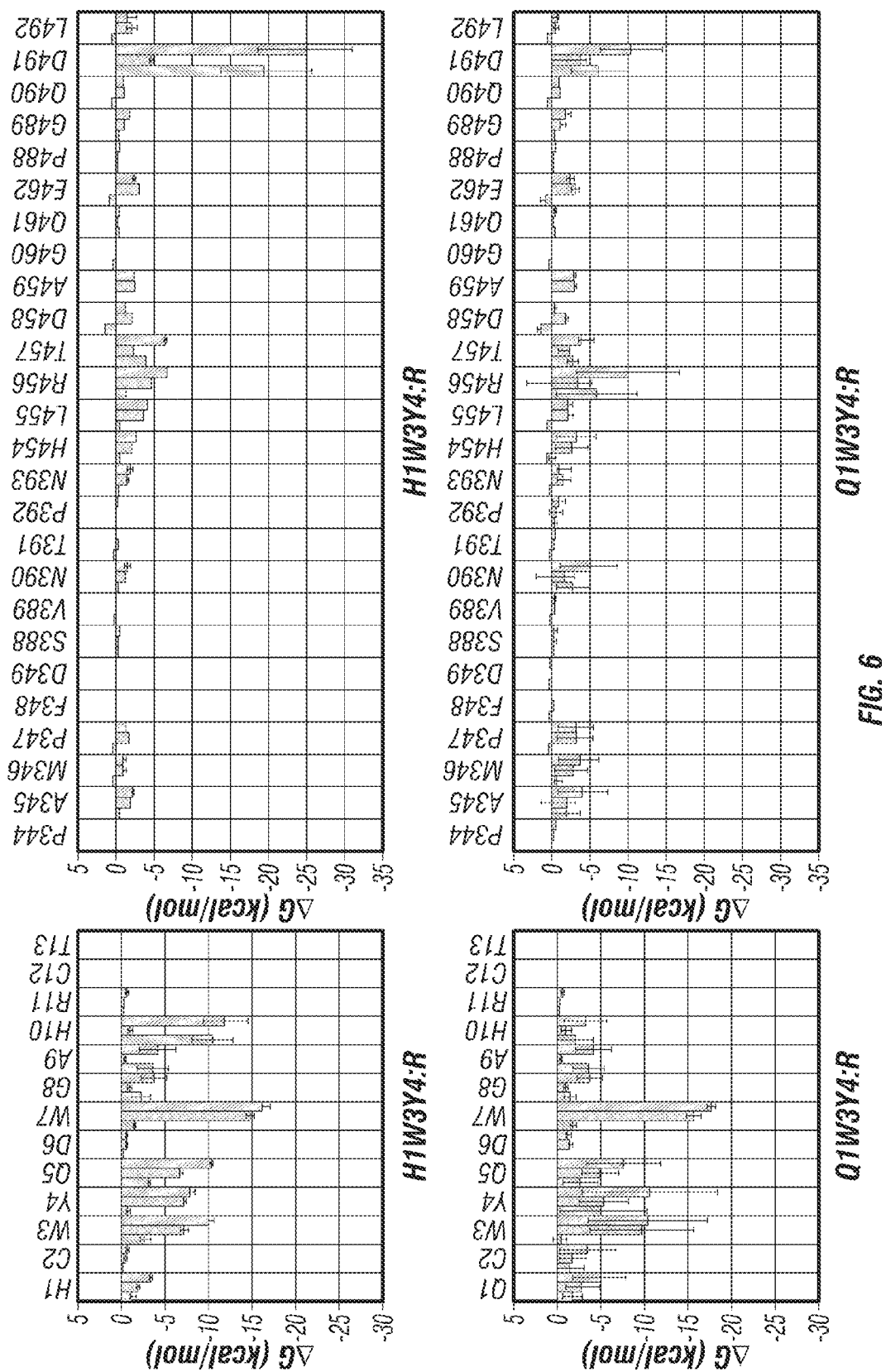
FIG. 6 shows residue intermolecular interaction energies for compstatin analogs (left panel) and C3 (right panel). For each complex, the energies are averaged over all corresponding runs. The uncertainties (error bars) are computed from the standard deviation of the average values.
Figure 6:
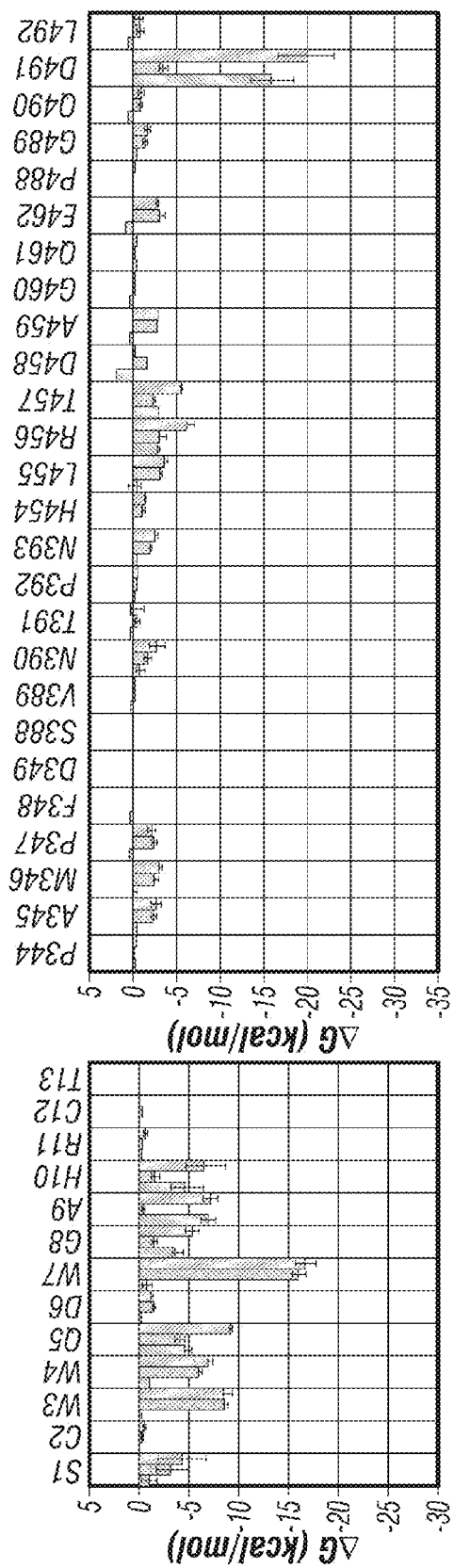
Figure 6:
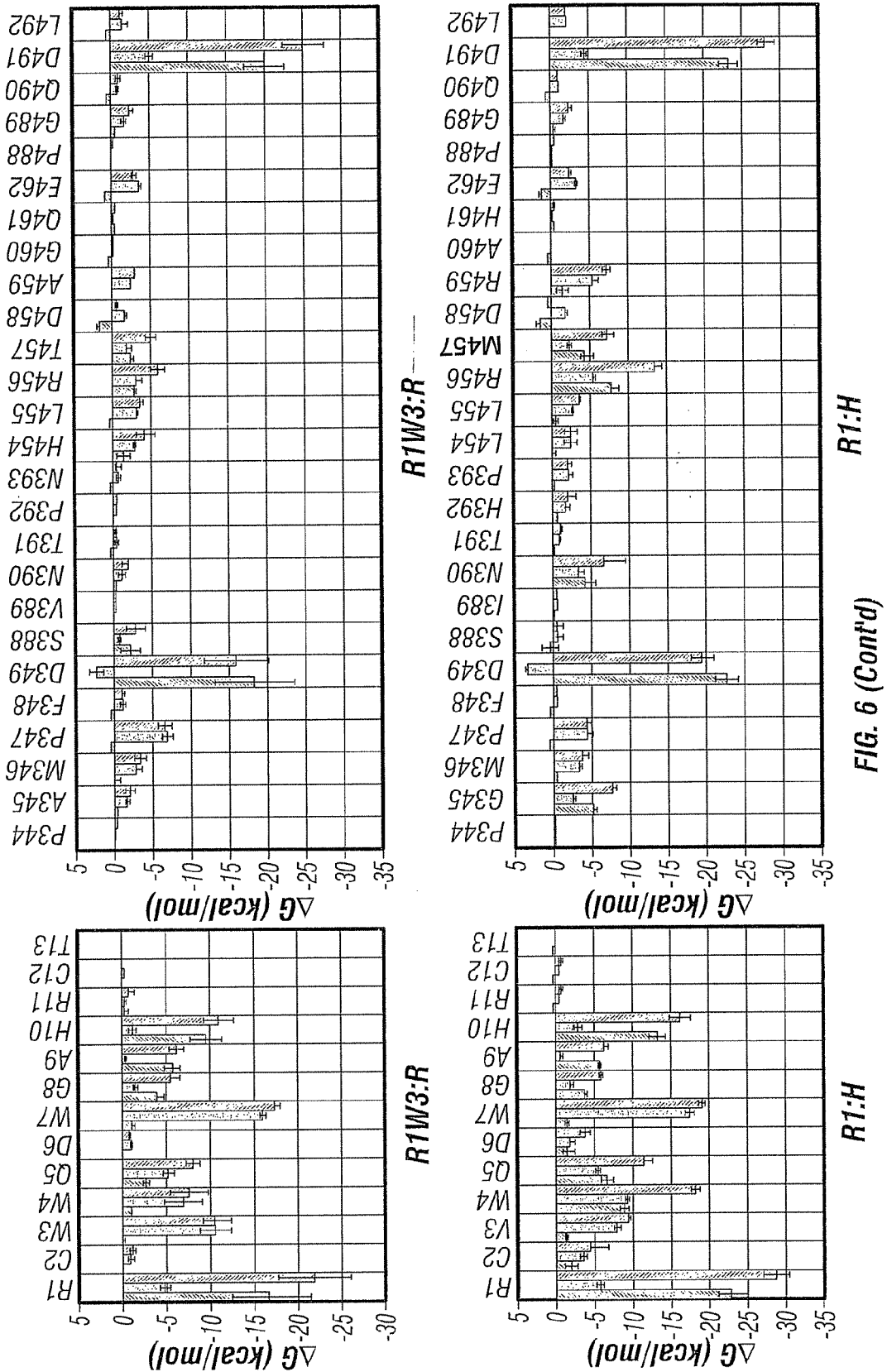
Figure 6:
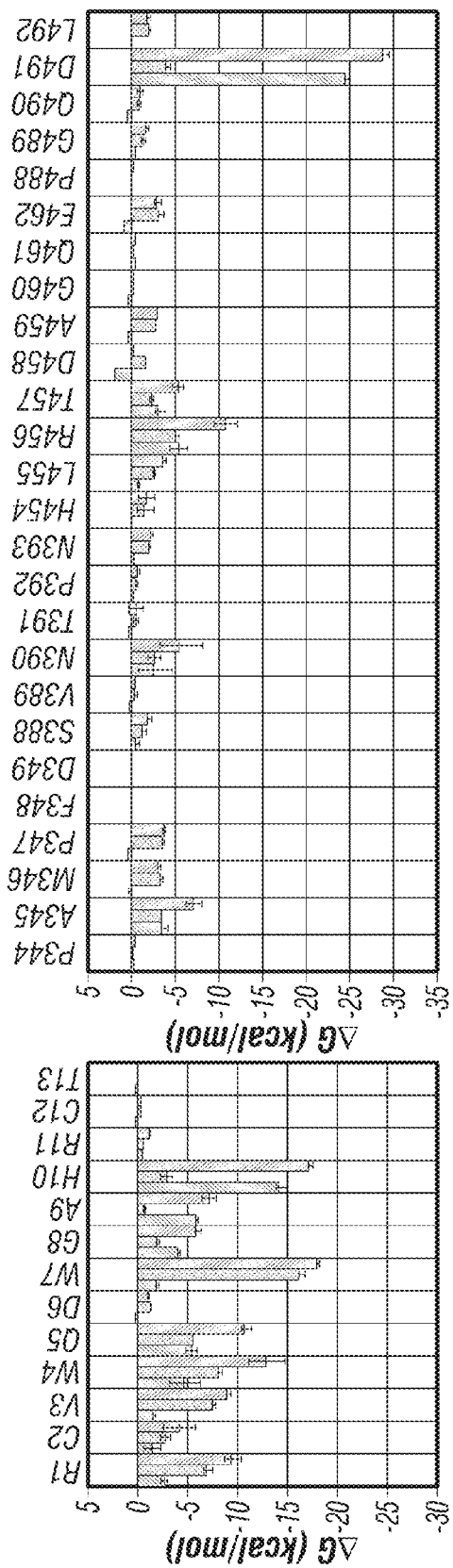
Figure 6:
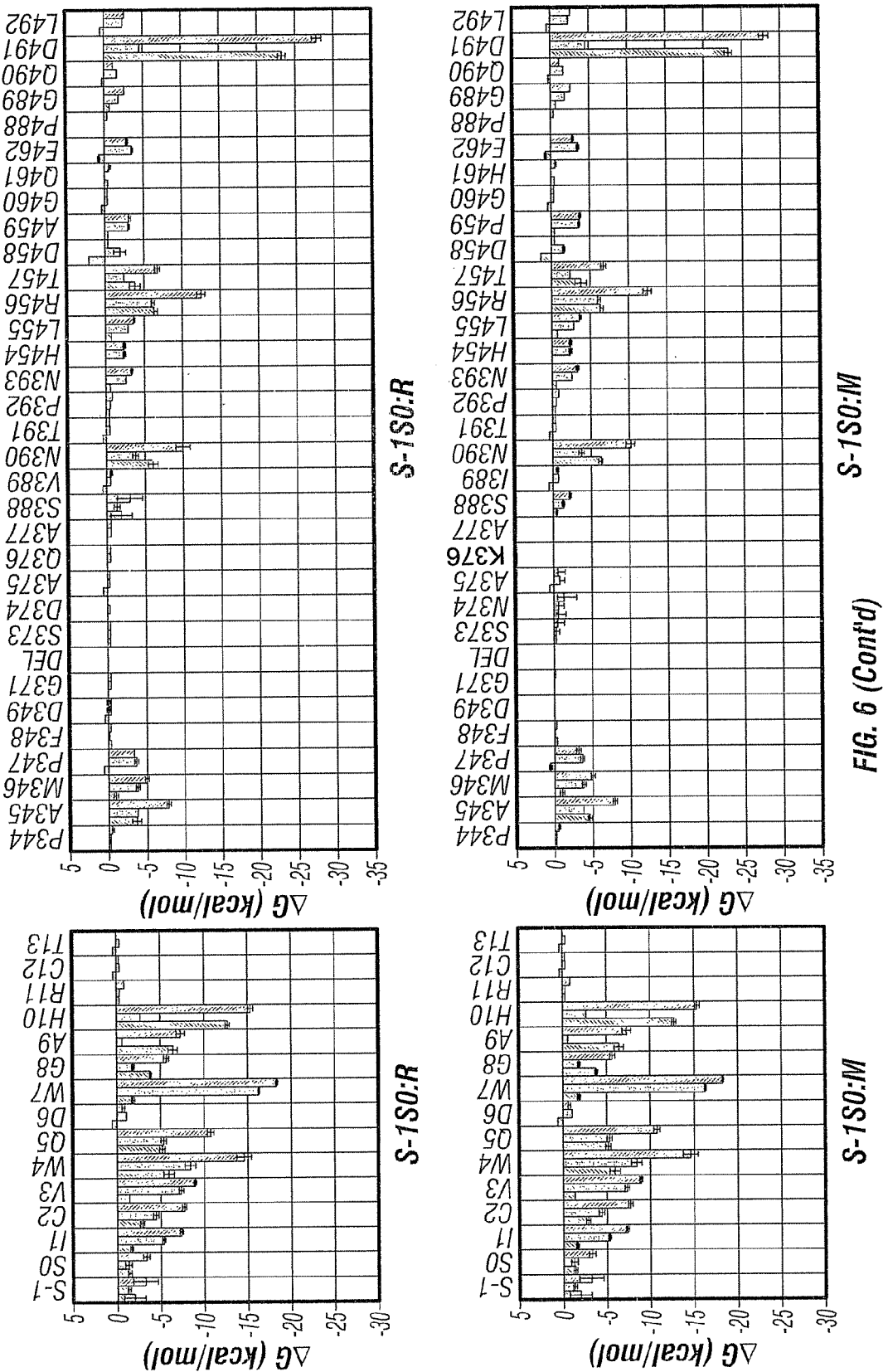
Figure 6:
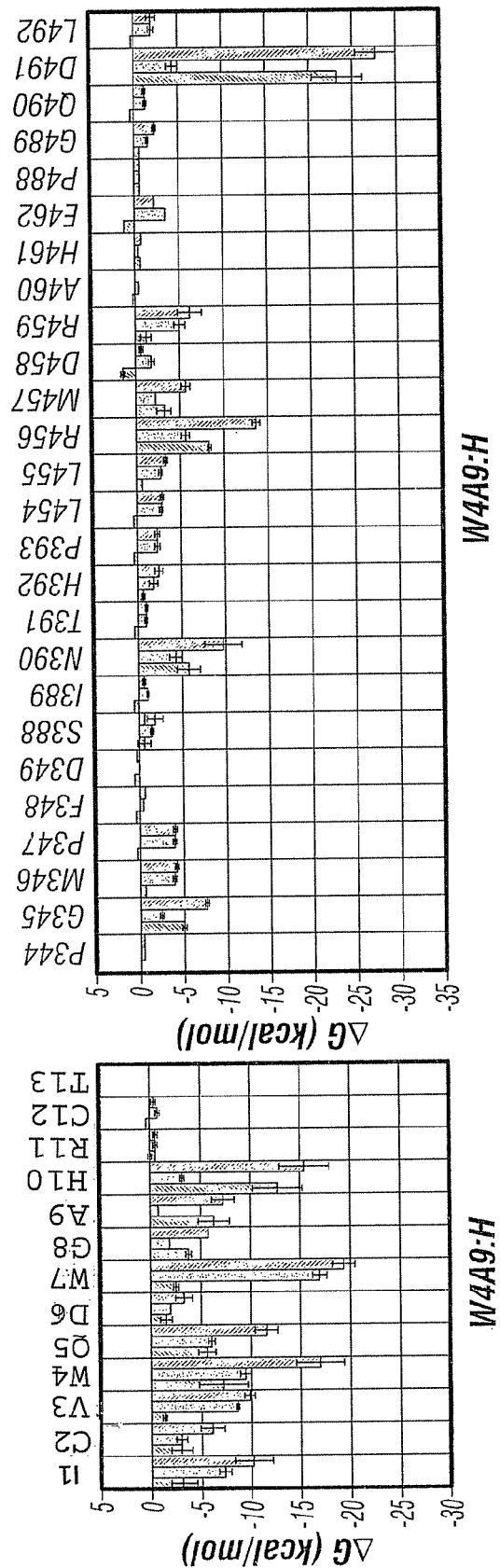
Figure 7:
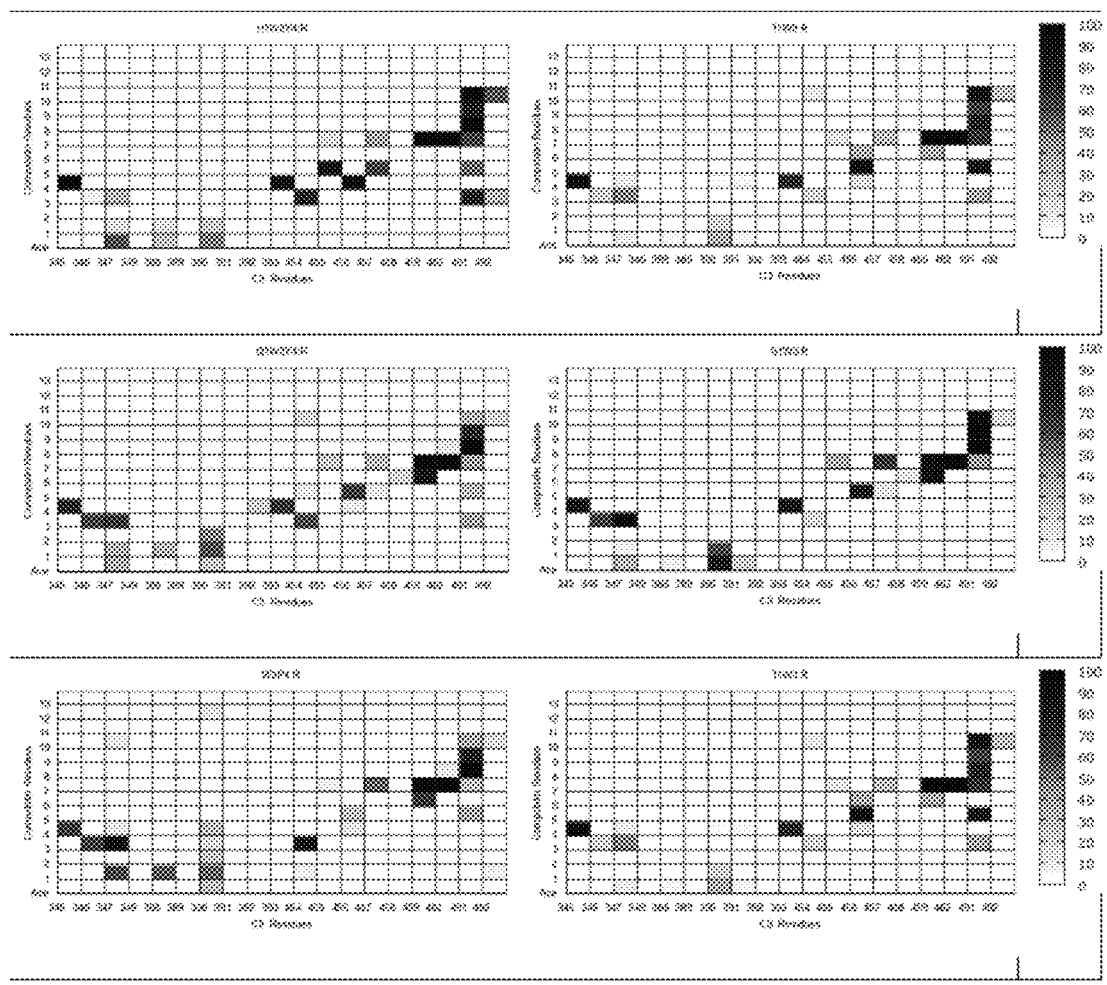
FIG. 7 shows probability density maps (%) of side chain contacts for selected protein-ligand side chain pairs. Two side chains are considered in contact if the distance between their geometric centers is smaller than 6.5 Å. For each complex, the probabilities are averaged over all corresponding runs.
Figure 7:
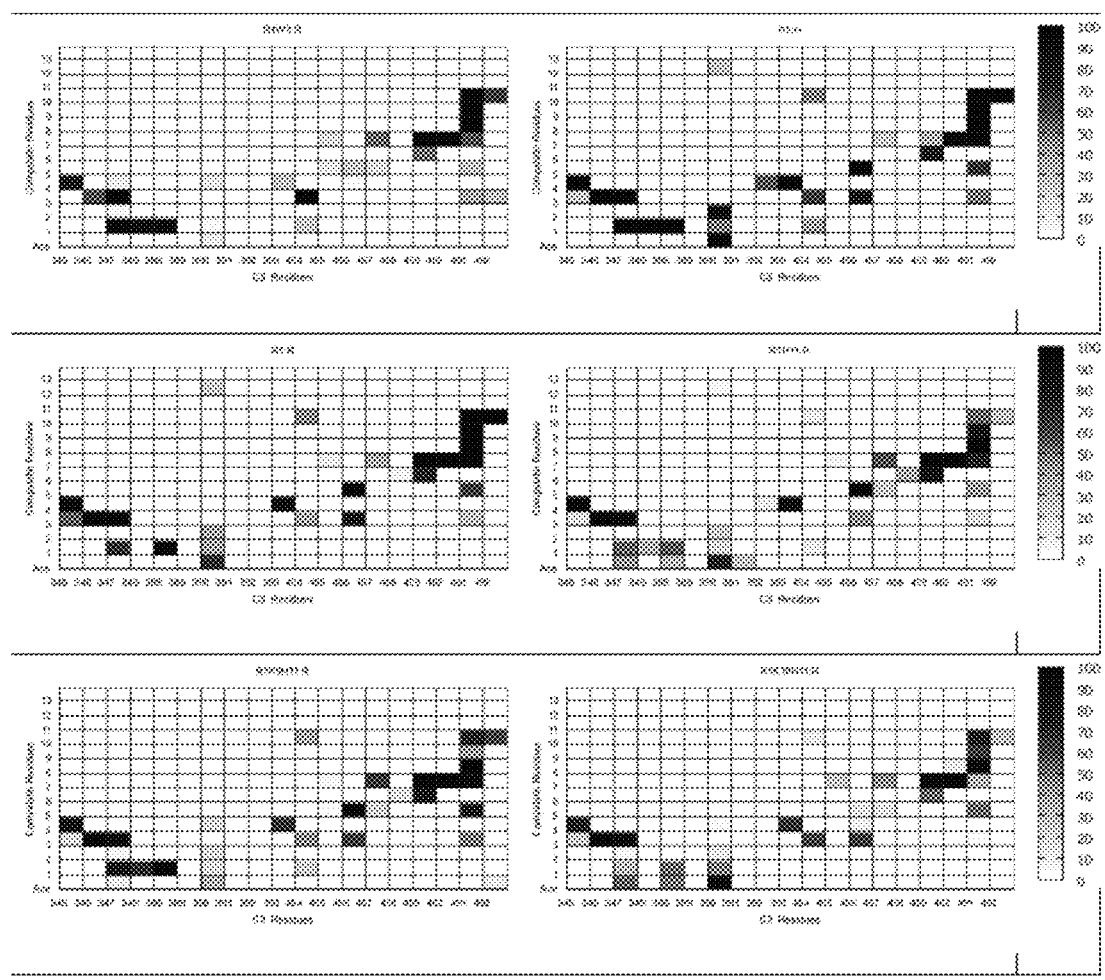
Figure 7:
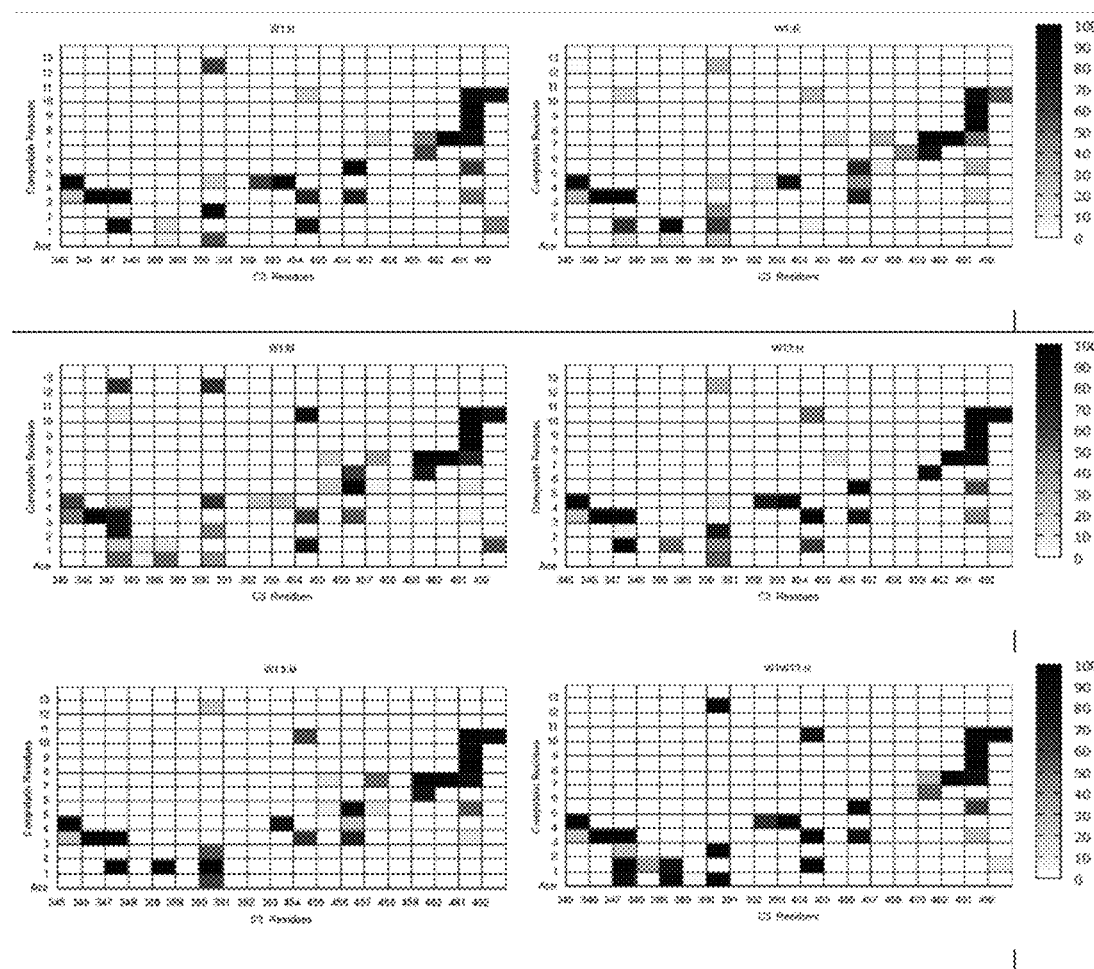
Figure 7:
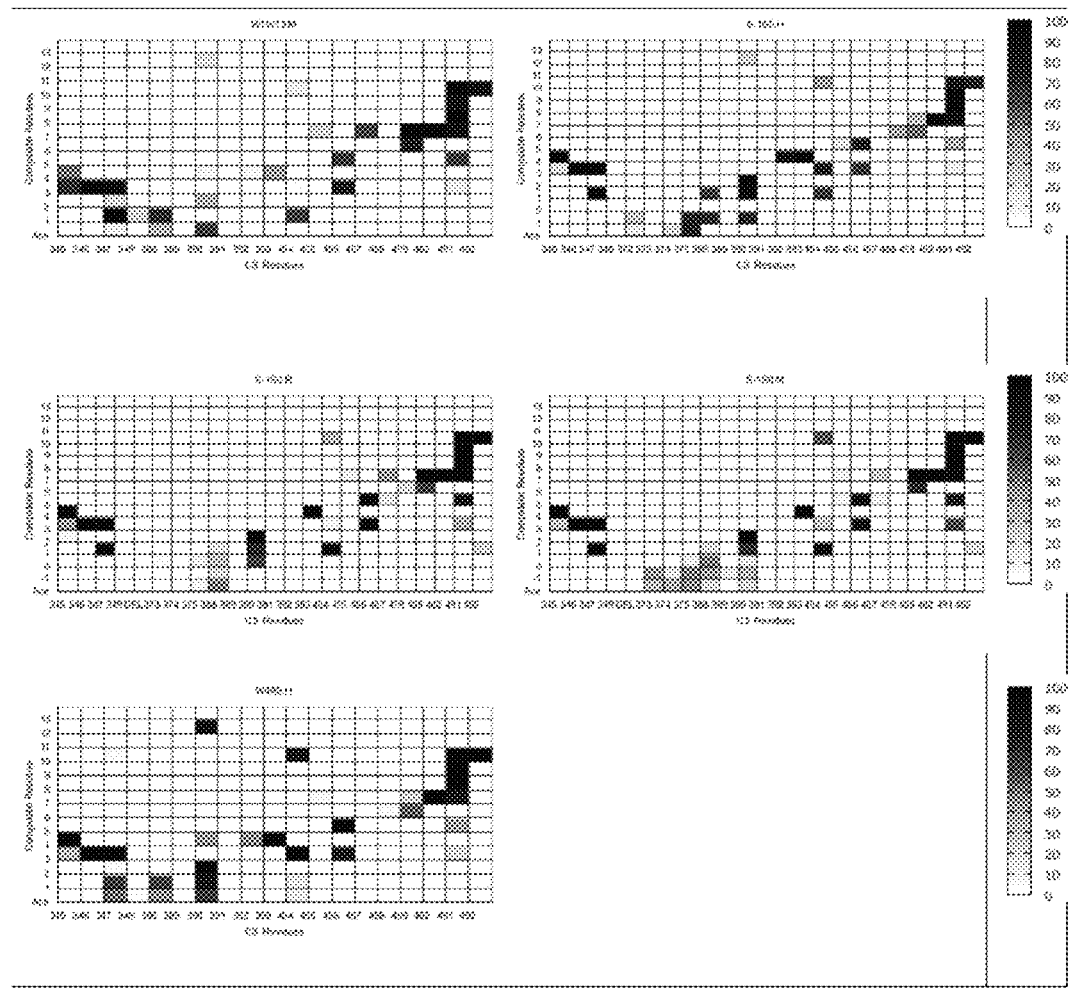
Figure 8B:
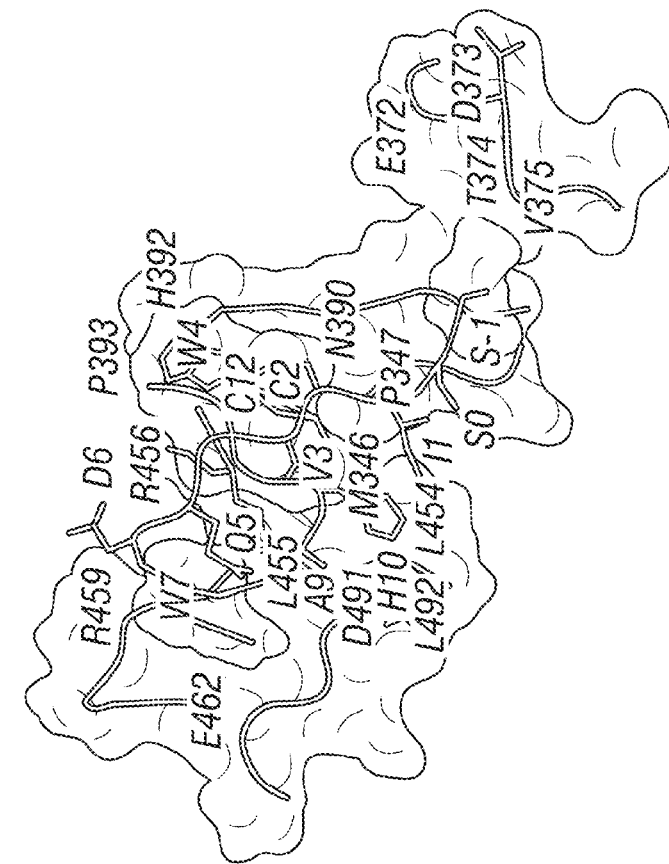
FIG. 8A-D shows simulation structures of the compstatin binding site for the complexes S-1S0:H (A, B) and S-1S0:M (C, D) at the end of runs S-1S0:H1 and S-1S0:M, respectively. Important hydrogen bonds and nonpolar contacts are shown, respectively, in the left and right panel. The labels I-IV (in A) indicate four protein sectors with atoms at least within 7 Å from the ligand (344-349, 388-393, 454-462 and 488-492). Compstatin is shown in red tubes and sticks. The violet tubes show the initial conformations of sectors I and II. The blue lines in plots A, C, E denote important hydrogen bonds. In plots B, D and F, protein residues are indicated by a cyan surface, and ligand residues Cys2, Val3, Trp4, Trp7 and Cys12 are indicated by a red surface.
Figure 8A:
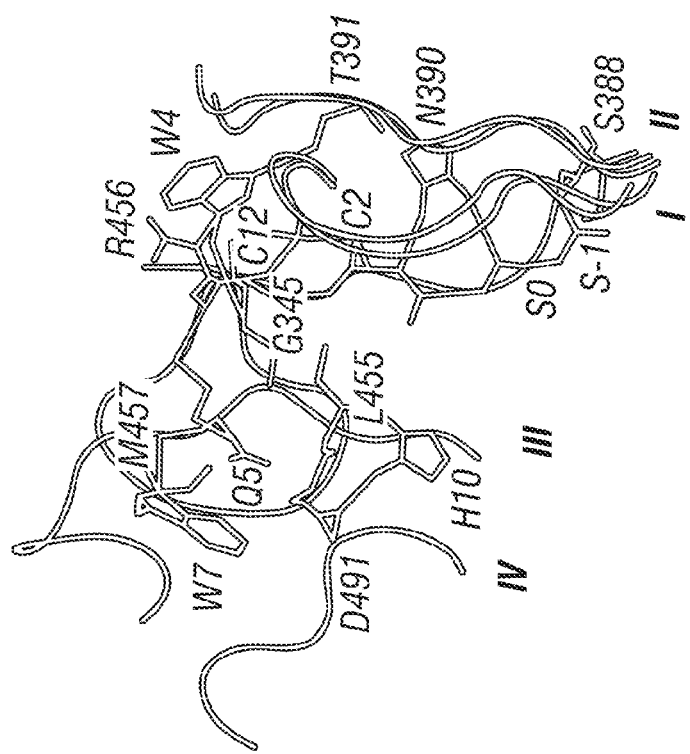
Figure 8D:
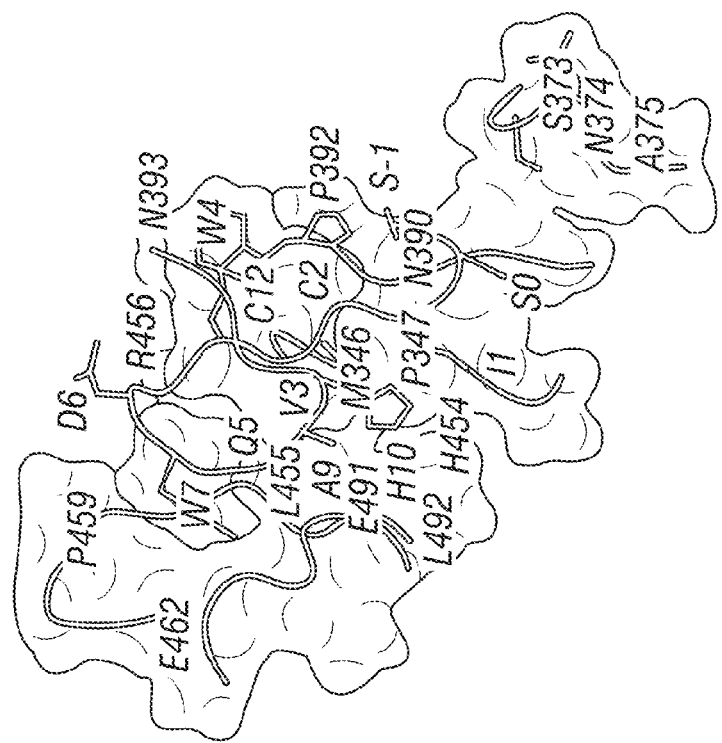
Figure 8C:
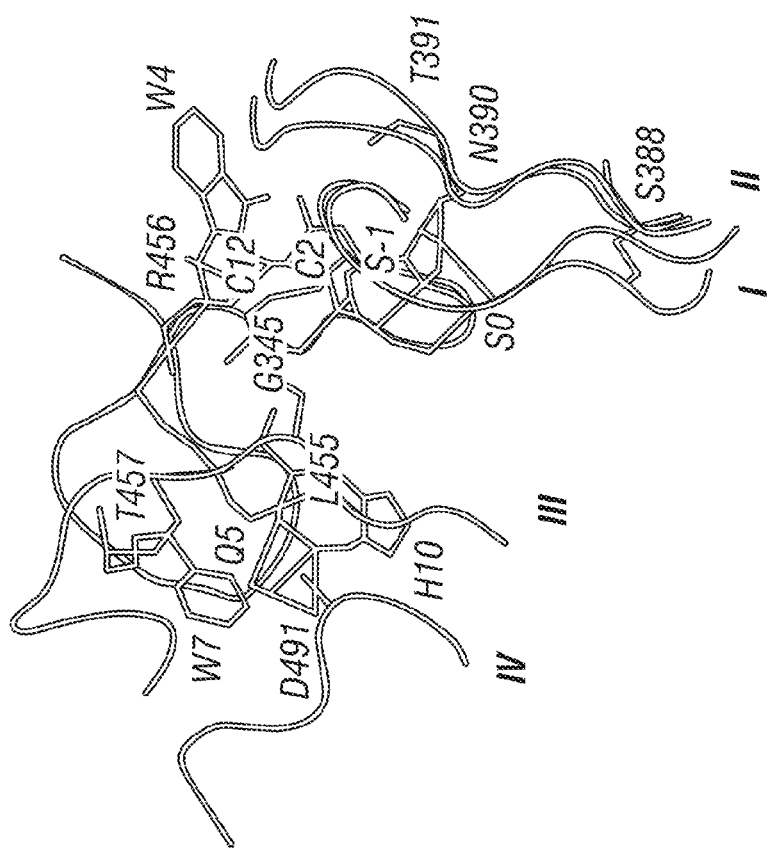

The statistics of important intermolecular hydrogen bonds for all complexes are listed in Tables 5A-D. Statistics of residue intermolecular energies are plotted in FIG. 6; non-polar interactions (side chain contacts) are shown in FIG. 7.

Table 5:

Intermolecular hydrogen-bond occupancies (%) for the various complexes studied in this work. These occupancies have been computed from the analysis of 700 snapshots (per run), extracted at 10-ps intervals from the last 7-ns of the MD simulations. A hydrogen bond was present if the donor (D)-acceptor (A) distance was less than 3.5 Å and the corresponding angle (D-H-A) was larger than 90°.

TABLE 5A

Intermolecular hydrogen bond occupancies (%) of the $1^{st}$-generation complexes.

| Intermolecular Atom Pairs | | Hydrogen Bond Occupancy (%) | | | | | | |
|---|---|---|---|---|---|---|---|---|
| | | H1W3Y4:R | Q1W3Y4:R1 | Q1W3Y4:R2 | W3P4:R | T1W3F4:R | S1W3:R | T1W3:R |
| His/Gln1 Side-NE2 | Asn390 Side-OD1 | 0.9 | 5 | 14 | 0 | 0 | 0 | 0 |
| XXX1 Side-OY | Asn390 Side-ND2 | 28 | 0.6 | 5 | 1 | 7 | 13 | 10 |
| Gln1 Side-OE | Asn390 Side-ND2 | 0 | 40 | 0.9 | 0 | 0 | 0 | 0 |
| XXX1 Side-OY$^a$ | Thr391 Main-N | 0 | 0 | 0 | 0 | 0.1 | 15 | 1 |
| XXX1 Main-N$^a$ | Asn390 Side-OD1 | 1 | 10 | 16 | 4 | 2 | 5 | 1 |
| Cys2 Main-O | Asn390 Side-ND2 | 0.1 | 0.7 | 0 | 23 | 0.1 | 0.4 | 0 |
| Cys2 Main-N | Asn390 Side-OD1 | 0.1 | 71 | 0.4 | 16 | 0.7 | 0.6 | 0.3 |
| Trp3 Side-NE1 | Gly/Ala345 Main-O | 0 | 0 | 0 | 0 | 13 | 0.1 | 0 |
| Trp3 Side-NE1 | Asp491 Main-O | 25 | 0 | 0 | 0 | 0 | 0 | 0 |
| Trp3 Side-NE1 | Asp491 Side-OD* | 44 | 0 | 0 | 0.1 | 0 | 0 | 0 |
| Trp4 Side-NE1 | Asn390 Main-O | 0 | 0 | 0 | 0 | 0 | 0 | 19 |
| Trp4 Side-NE1 | Thr391 Main-O | 0 | 0 | 0 | 0 | 0 | 0 | 53 |
| XXX4 Main-O$^a$ | Arg456 Side-NH* | 0 | 74 | 1 | 0 | 0.9 | 1 | 5 |
| Tyr4 Side-OH | Pro/Asn393 Side-ND2 | 22 | 0 | 7 | 0 | 0 | 0 | 0 |
| XXX4 Main-O$^a$ | Arg456 Side-NE | 1 | 95 | 1 | 0 | 7 | 3 | 2 |
| XXX4 Main-N$^a$ | Gly/Ala345 Main-O | 2 | 94 | 2 | 0 | 5 | 3 | 0.4 |
| Gln5 Side-OE | Met/Thr457 Main-N | 77 | 80 | 11 | 40 | 50 | 84 | 30 |
| Gln5 Side-NE2 | Leu455 Main-O | 16 | 53 | 18 | 50 | 32 | 66 | 60 |
| Asp6 Side-OD | Arg456 Side-NH* | 0 | 0.1 | 0 | 0 | 0 | 0 | 35 |
| Trp7 Side-NE1 | Met/Thr457 Main-O | 99 | 98 | 99 | 83 | 98 | 94 | 100 |
| Ala9 Main-N | Asp491 Side-OD* | 63 | 70 | 27 | 62 | 97 | 96 | 48 |
| His10 Side-ND1 | Leu/His454 Side-NE2 | 0 | 13 | 0 | 0 | 0 | 0 | 0 |
| His10 Side-NE2 | Leu/His454 Side-ND1 | 0 | 0.9 | 0.1 | 0 | 63 | 0 | 7 |
| His10 Side-ND1 | Asp491 Side-OD* | 87 | 3 | 20 | 17 | 0 | 52 | 27 |
| His10 Main-N | Asp491 Side-OD* | 58 | 14 | 17 | 33 | 79 | 35 | 31 |

TABLE 5B

Intermolecular hydrogen bond occupancies (%) of the $2^{nd}$-generation complexes.

| Intermolecular Atom Pairs | | Hydrogen Bond Occupancy (%) | | | | | | | | | |
|---|---|---|---|---|---|---|---|---|---|---|---|
| | | R1W3: R1 | R1W3: R2 | R1: H1 | R1: H2 | R1: R | R1H11: R1 | R1H11: R2 | R1K9H11: R1 | R1K9H11: R2 | R1K10H11: R1 | R1K10H11: R2 |
| Arg1 Side-NH | Ser388 Main-O | 0 | 0 | 0 | 0 | 1 | 0 | 0 | 0.7 | 0 | 0 | 16 |
| Arg1 Side-NH | Asp349 Side-OD | 93 | 77 | 100 | 100 | 0 | 64 | 0 | 42 | 88 | 0 | 0 |
| Arg1 Side-NH | Ser388 Side-OG | 67 | 39 | 23 | 68 | 11 | 42 | 0.6 | 27 | 55 | 0 | 3 |
| Arg1 Side-NH | Leu/His454 Side-NE2 | 0 | 28 | 0 | 0 | 0.3 | 2 | 1 | 0.1 | 1 | 0 | 0 |
| Arg1 Side-OY | Asn390 Side-ND2 | 0.9 | 0.7 | 51 | 86 | 11 | 2 | 11 | 21 | 20 | 0 | 31 |
| Arg1 Side-NH | Ser437 Side-OG | 1 | 18 | 2 | 31 | 0 | 6 | 0 | 0.1 | 7 | 0 | 1 |
| Arg1 Side-OY | Thr391 Main-N | 0 | 0 | 0 | 0 | 0 | 0 | 45 | 0 | 0 | 0 | 0 |
| Arg1 Side-NH | Phe348 Main-O | 11 | 14 | 0.1 | 1 | 0 | 0 | 0 | 0 | 14 | 0 | 0 |
| Arg1 Main-N | Asn390 Side-OD1 | 2 | 3 | 0 | 0 | 14 | 0.9 | 12 | 0 | 0 | 59 | 0.3 |
| Cys2 Main-N | Asn390 Side-OD1 | 0.4 | 0.3 | 34 | 78 | 32 | 31 | 5 | 18 | 0.7 | 0.1 | 24 |
| Trp4 Side-NE1 | Thr391 Main-O | 0 | 0 | 28 | 23 | 5 | 12 | 13 | 0.6 | 0.6 | 0.3 | 0.1 |
| Trp4 Side-NE1 | Asn393 Side-ND2 | 2 | 0 | 0 | 0 | 2 | 6 | 2 | 26 | 0.1 | 0 | 0 |
| Trp4 Main-O | Arg456 Side-NH* | 4 | 0.6 | 53 | 54 | 29 | 94 | 75 | 77 | 11 | 0.3 | 4 |
| Trp4 Main-O | Arg456 Side-NE | 16 | 7 | 95 | 96 | 51 | 96 | 93 | 90 | 38 | 18 | 30 |
| Trp4 Main-N | Gly/Ala345 Main-O | 8 | 1 | 100 | 99 | 75 | 80 | 93 | 85 | 54 | 81 | 35 |
| Gln5 Side-OE | Met/Thr457 Main-N | 29 | 60 | 100 | 97 | 84 | 72 | 90 | 99 | 90 | 12 | 75 |

TABLE 5B-continued

Intermolecular hydrogen bond occupancies (%) of the $2^{nd}$-generation complexes.

| Intermolecular Atom Pairs | | R1W3: R1 | R1W3: R2 | R1: H1 | R1: H2 | R1: R | R1H11: R1 | R1H11: R2 | R1K9H11: R1 | R1K9H11: R2 | R1K10H11: R1 | R1K10H11: R2 |
|---|---|---|---|---|---|---|---|---|---|---|---|---|
| Gln5 Side-NE2 | Leu455 Main-O | 54 | 20 | 75 | 91 | 89 | 25 | 40 | 85 | 90 | 52 | 54 |
| Asp6 Main-O | Arg/Ala/Pro459 Side-NH | 0 | 0 | 19 | 12 | 0 | 0 | 0 | 0 | 0 | 0 | 0 |
| Asp6 Side-OD | Arg/Ala/Pro459 Side-NH | 0 | 0 | 2 | 12 | 0 | 0 | 0 | 0 | 0 | 0 | 0 |
| Trp7 Side-NE1 | Met/Thr457 Main-O | 97 | 99 | 99 | 98 | 99 | 99 | 99 | 100 | 100 | 99 | 97 |
| Ala/Lys9 Main-N | Asp491 Side-OD* | 99 | 90 | 98 | 98 | 98 | 79 | 41 | 99 | 22 | 7 | 74 |
| Lys10 Side-NZ | Asp491 Side-OD* | 0 | 0 | 0 | 0 | 0 | 0 | 0 | 0 | 0 | 46 | 0 |
| His10 Side-ND1 | Asp491 Side-OD* | 22 | 39 | 99 | 90 | 87 | 24 | 0 | 96 | 2 | 0 | 0 |
| His/Lys10 Main-N | Asp491 Side-OD* | 81 | 84 | 92 | 97 | 97 | 25 | 30 | 96 | 20 | 3 | 61 |

TABLE 5C

Intermolecular hydrogen bond occupancies (%) of the $3^{rd}$-generation complexes.

| Intermolecular Atom Pairs | | W1:H1 | W1:H2 | W1:R | W1:M | W13:H | W13:M | W1W13:H | W1W13:M |
|---|---|---|---|---|---|---|---|---|---|
| Trp1 Side-NE1 | Ser388 Main-O | 0 | 0 | 46 | 0 | 0 | 0 | 0 | 0 |
| Trp1 Side-OY | Asn390 Side-ND2 | 5 | 1 | 0.4 | 19 | 4 | 0 | 49 | 19 |
| Trp1 Side-NE1 | Ser388 Side-OG | 0 | 0.1 | 13 | 0.9 | 0 | 0 | 0 | 0 |
| Trp1 Side-NE1 | Leu/His454 Side-NE2 | 0 | 0 | 0 | 58 | 0 | 0 | 0 | 34 |
| Trp1 Main-N | Asn390 Side-ND2 | 0 | 0.1 | 0.3 | 6 | 2 | 0 | 17 | 6 |
| Trp1 Main-N | Asn390 Side-OD1 | 0 | 3 | 18 | 23 | 5 | 0 | 3 | 34 |
| Cys2 Main-O | Asn390 Side-ND2 | 0 | 47 | 33 | 0.3 | 0.1 | 11 | 3 | 11 |
| Cys2 Main-N | Asn390 Side-OD1 | 86 | 65 | 19 | 11 | 48 | 49 | 96 | 20 |
| Trp4 Side-NE1 | Asn390 Side-OD1 | 0 | 22 | 10 | 61 | 0.7 | 0 | 0 | 0 |
| Trp4 Side-NE1 | Thr391 Main-O | 23 | 16 | 9 | 20 | 23 | 0 | 30 | 3 |
| Trp4 Main-O | Arg456 Side-NH* | 64 | 36 | 53 | 82 | 67 | 31 | 45 | 10 |
| Trp4 Main-O | Arg456 Side-NE | 99 | 97 | 93 | 95 | 79 | 94 | 26 | |
| Trp4 Main-N | Gly/Ala345 Main-O | 100 | 99 | 96 | 97 | 100 | 92 | 100 | 43 |
| Gln5 Side-OE | Met/Thr457 Main-N | 96 | 97 | 62 | 87 | 99 | 84 | 100 | 44 |
| Gln5 Side-NE2 | Leu455 Main-O | 92 | 73 | 50 | 97 | 91 | 79 | 82 | 55 |
| Asp6 Main-O | Arg 459 Side-NE | 0 | 12 | 0 | 0 | 0 | 0 | 0.1 | 0 |
| Asp6 Main-O | Arg 459 Side-NH | 31 | 42 | 0 | 0 | 6 | 0 | 10 | 0 |
| Asp6 Side-OD | Arg459 Side-NH | 60 | 21 | 0 | 0 | 8 | 0 | 3 | 0 |
| Asp6 Side-OD | Arg456 Side-NH* | 0 | 0 | 0 | 59 | 0 | 0 | 0 | 0 |
| Trp7 Side-NE1 | Met/Thr457 Main-O | 99 | 99 | 88 | 98 | 99 | 99 | 100 | 96 |
| Ala9 Main-N | Asp491 Side-OD* | 98 | 98 | 96 | 97 | 99 | 77 | 98 | 83 |
| His10 Side-NE2 | Leu/His454 Side-ND1 | 0 | 0 | 1 | 44 | 0 | 0 | 0 | 0 |
| His10 Side-ND1 | Asp491 Main-O | 0 | 0 | 13 | 0 | 0 | 0 | 0 | 0 |
| His10 Side-ND1 | Asp491 Side-OD* | 91 | 0 | 0.1 | 0 | 0.1 | 81 | 44 | 92 |
| His10 Main-N | Asp491 Side-OD* | 90 | 99 | 37 | 67 | 99 | 88 | 99 | 83 |
| Arg11 Main-N | Asp491 Side-OD* | 0 | 0 | 0 | 0.1 | 0.1 | 4 | 0 | 12 |

TABLE 5D

Intermolecular hydrogen bond occupancies (%) of the $4^{th}$-generation complexes.

| Intermolecular Atom Pairs | | S-1S0:H1 | S-1S0:H2 | S-1S0:R1 | S-1S0:R2 | S-1S0:M1 | S-1S0:M2 |
|---|---|---|---|---|---|---|---|
| Ser-1 Main-O | Asn390 Side-ND2 | 0 | 0 | 0 | 0 | 48 | 0 |
| Ser-1 Side-OY | Thr/Asp/Asn374 Main-N | 0 | 0 | 0 | 0 | 0 | 22 |
| Ser-1 Side-OG | Asn390 Side-ND2 | 18 | 8 | 0 | 0 | 0 | 12 |
| Ser-1 Main-O | Ser388 Side-OG | 0 | 0 | 58 | 4 | 0 | 0 |
| Ser-1 Side-OG | Glu372 Side-OE | 13 | 0 | 0 | 0 | 0 | 0 |
| Ser-1 Side-OY | Lys386 Side-NZ | 0 | 0 | 13 | 13 | 0 | 0 |

TABLE 5D-continued

Intermolecular hydrogen bond occupancies (%) of the 4th-generation complexes.

| Intermolecular Atom Pairs | | Hydrogen Bond Occupancy (%) | | | | | |
|---|---|---|---|---|---|---|---|
| | | S-1S0:H1 | S-1S0:H2 | S-1S0:R1 | S-1S0:R2 | S-1S0:M1 | S-1S0:M2 |
| Ser-1 Main-N | Glu372 Side-OE | 10 | 2 | 0 | 0 | 0 | 0 |
| Ser-1 Side-OY | Ser388 Side-OG | 0 | 0 | 2 | 12 | 0 | 0 |
| Ser-1 Side-OG | Ser388 Main-O | 39 | 6 | 0 | 0 | 0 | 0 |
| SerO Main-O | Asn390 Side-ND2 | 66 | 58 | 94 | 90 | 78 | 97 |
| SerO Side-OG | Asn390 Side-ND2 | 0 | 0 | 12 | 20 | 0 | 1 |
| SerO Side-OG | Ser388 Side-OG | 0 | 0 | 0 | 0 | 14 | 0 |
| Cys2 Main-N | Asn390 Side-OD1 | 96 | 94 | 94 | 92 | 93 | 87 |
| Trp4 Side-NE1 | Thr391 Main-O | 28 | 22 | 0.1 | 0.1 | 1 | 0.3 |
| Trp4 Main-O | Arg456 Side-NH* | 39 | 62 | 36 | 38 | 21 | 30 |
| Trp4 Main-O | Arg456 Side-NE | 97 | 99 | 86 | 79 | 79 | 82 |
| Trp4 Main-N | Gly/Ala345 Main-O | 100 | 99 | 81 | 61 | 93 | 90 |
| Gln5 Side-OE | Met/Thr457 Main-N | 98 | 83 | 87 | 96 | 80 | 96 |
| Gln5 Side-NE2 | Leu455 Main-O | 52 | 9 | 81 | 90 | 49 | 89 |
| Asp6 Main-O | Arg459 Side-NH | 2 | 34 | 0 | 0 | 0 | 0 |
| Trp7 Side-NE1 | Met/Thr457 Main-O | 96 | 100 | 99 | 98 | 99 | 98 |
| Ala9 Main-N | Asp491 Side-OD* | 89 | 85 | 99 | 100 | 99 | 99 |
| His10 Side-ND1 | Asp491 Side-OD* | 80 | 0 | 98 | 100 | 99 | 100 |
| His10 Main-N | Asp491 Side-OD* | 63 | 0.6 | 85 | 89 | 77 | 53 |

Non-Primate Complexes.

First Generation.

The analogs of this generation were studied in complex with the rat protein and showed a similar dynamical behavior with the W4A9:rC3 complex. The ligand lost intermolecular interactions with Sectors 388-393 and 488-492, as documented in Tables 5-6 and FIGS. 6-7. The only exception was run Q1W3Y4:R1, in which sector 388-383 remained near the starting conformation; this behavior was not reproduced in the second run (Q1W3Y4:R2). The computed affinities (Table 6) were in the range −37 to −41 kcal/mol, significantly worse than the corresponding affinities of W4A9 for rC3 (−46 kcal/mol) and hC3 (−55 kcal/mol).

TABLE 6

Association free energies for complexes not included in table 3 of main text.

| | Binding Free Energy | | | | | | |
|---|---|---|---|---|---|---|---|
| Run | Total | | Polar Component[a] | | Non-polar Component[a] | | Polar Interaction[b] |
| | | Std Dev | | Std Dev | | Std Dev | Std Dev |

Generation 1

| H1W3Y4:R | −40.7 | 0.9 | 3.4 | 0.1 | −44.1 | 0.8 | −28.3 | 5.4 |
| Q1W3Y4:R1 | −51.0 | 0.8 | 9.6 | 1.0 | −60.6 | 0.2 | −32.5 | 0.9 |
| Q1W3Y4:R2 | −29.4 | 6.1 | 3.5 | 0.2 | −32.9 | 6.4 | −10.0 | 7.2 |
| Average | −40.2 | 11.7 | 6.5 | 3.1 | −46.7 | 14.6 | −21.2 | 12.3 |
| W3P4:R | −37.7 | 7.7 | 4.6 | 0.8 | −42.3 | 8.6 | −14.4 | 3.4 |
| T1W3F4:R | −37.3 | 1.1 | 6.3 | 0.0 | −43.5 | 1.1 | −27.6 | 4.8 |
| S1W3:R | −41.1 | 1.0 | 3.2 | 0.9 | −44.2 | 0.0 | −24.5 | 2.2 |
| T1W3:R | −38.6 | 0.4 | 3.7 | 2.5 | −42.3 | 2.9 | −20.2 | 1.6 |

Generation 2

| R1W3:R1 | −47.8 | 0.2 | 3.2 | 0.4 | −50.9 | 0.6 | −46.2 | 2.4 |
| R1W3:R2 | −47.8 | 0.3 | 3.5 | 0.8 | −51.3 | 0.4 | −42.8 | 2.9 |
| Average | −47.8 | 0.3 | 3.3 | 0.6 | −51.1 | 0.6 | −44.5 | 3.1 |
| R1:R | −50.9 | 0.3 | 3.4 | 1.5 | −54.3 | 1.8 | −41.9 | 1.7 |
| R1H11:R1 | −45.6 | 1.2 | 4.2 | 3.1 | −49.8 | 4.3 | −44.1 | 2.6 |
| R1H11:R2 | −47.5 | 0.4 | 5.4 | 0.3 | −52.9 | 0.1 | −30.3 | 2.8 |
| Average | −46.5 | 1.3 | 4.8 | 2.3 | −51.3 | 3.4 | −37.2 | 7.4 |
| R1K9H11:R1 | −48.6 | 0.1 | 2.7 | 0.7 | −51.2 | 0.5 | −20.6 | 0.9 |
| R1K9H11:R2 | −45.3 | 0.5 | 3.7 | 0.5 | −49.1 | 1.0 | −25.8 | 4.4 |

TABLE 6-continued

Association free energies for complexes not included in table 3 of main text.

| | Binding Free Energy | | | | | | |
|---|---|---|---|---|---|---|---|
| Run | Total | Std Dev | Polar Component[a] | Std Dev | Non-polar Component[a] | Std Dev | Polar Interaction[b] | Std Dev |
| Average | −46.9 | 1.7 | 3.2 | 0.8 | −50.1 | 1.4 | −23.2 | 4.1 |
| R1K10H11:R1 | −49.9 | 1.9 | 3.9 | 0.0 | −53.8 | 1.9 | −55.5 | 9.7 |
| R1K10H11:R2 | −46.9 | 0.5 | 4.6 | 2.0 | −51.5 | 1.6 | −38.1 | 0.7 |
| Average Generation 3 | −48.4 | 2.1 | 4.2 | 1.5 | −52.7 | 2.1 | −46.8 | 11.0 |
| W1:R | −47.8 | 0.9 | 7.2 | 0.9 | −55.0 | 0.0 | −31.0 | 7.1 |
| W1:M | −51.1 | 0.9 | 5.7 | 0.6 | −56.9 | 0.4 | −44.7 | 0.4 |
| W13:H | −51.4 | 2.4 | 5.6 | 0.1 | −57.0 | 2.5 | −46.8 | 2.8 |
| W13:M | −50.6 | 1.4 | 4.8 | 0.4 | −55.4 | 1.8 | −40.4 | 4.7 |
| W1W13:H | −61.4 | 2.8 | 7.1 | 1.3 | −68.5 | 1.5 | −45.0 | 2.1 |
| W1W13:R | −48.9 | 3.0 | 5.6 | 0.9 | −54.5 | 2.1 | −34.1 | 7.5 |

All values are averaged over 700 snapshots (last 7-ns). Averages over multiple runs are underlined.
[a]Polar and non-polar components are defined in Eq. (2).
[b]The polar interaction components [Eq. (3)] measure the strength of intermolecular polar (Coulomb and GB) interactions in the complexes.

Second Generation.

All analogs of this group were studied in complex with the rat protein. With the parent analog R1W3 two runs were conducted (R1W3:R1-2), in which Arg1 formed a frequent salt bridge with Asp349; an example of this interaction is shown in FIG. 1A, for the R1 complex with hC3. The Arg1-Asp349 salt bridge improved R1W3 affinity for rC3 (−47.8 kcal/mol), relative to W4A9 and all other first-generation analogs (Table 6). Still, it was by ~8 kcal/mol weaker than the corresponding affinity of W4A9 for hC3 (−55 kcal/mol). For this reason, additional substitutions were introduced at positions 9-11 (R1, R1H11, R1K9H11, R1K10H11). The native Val at position 3 was also restored, based on the observation that the Trp3 side chain formed extensive non-polar contacts with Met346, Pro347, His454 in the R1W3 runs, but the ligand main chain moiety 1-4 was somewhat shifted with respect to its position in the crystallographic complex; this displacement hindered the formation of hydrogen bonds between the main chain of residues 2 or 4 and the protein.

The interactions of the first analog (R1) with rC3 were similar to the ones of the W4A9:rC3 complex; the analog moiety 1-3 formed somewhat improved non polar contacts with protein residues Met346, Pro347, Ser388 and Asn390. The computed affinity for rC3 was −50.9 kcal/mol (Table 6), improved by ~−5 kcal/mol compared to W4A9, and by ~−2 kcal/mol compared to R1W3. The additional substitutions at positions 9-11 (complexes R1K9H11:R, R1K10H11:R, R1H11:R in Table 6) had a worsening effect of affinity, presumably, the original W4A9 residues (A9, H10) were already optimal choices at these positions.

Third Generation.

Various rat and mouse complexes (W1:R, W1:M, W13:M, W1W13:M) were simulated and improved interactions were observed with respect to the first two generations, and computed an overall enhancement of affinity by ~−2 to −5 kcal/mol, relative to the W4A9 affinity for rC3. This overall enhancement with respect to the first two generations is mainly attributed to improved non-polar interactions between Trp1 and residues Pro347, Ser388, Asn390, His454 and partly Leu492 (an example of these interactions is shown in FIG. 1D, for the W1 complex with hC3. An additional intramolecular (ligand) n-cation interaction between Arg11 and Trp13 was observed in the W13:M and W1W13:M simulations; in both complexes, this interaction seemed to stabilize the bound conformation (especially in the region 8-13) of the ligand despite the displacement of sector 388-393, assisting thus the formation of intermolecular hydrogen bonds, between Ala9 or His10 and Asp491. Nevertheless, a complete recovery of the W4A9:hC3 hydrogen bond (Table 5C) and non-polar interactions (FIG. 6) was not achieved.

Fourth Generation.

The results of the first three generations suggest that the introduction of polar, ionic or aromatic interactions at position 1 does not increase the computed affinity for rC3/mC3 to the level of W4A9 affinity for hC3. In the fourth generation, the ligand outside the Cys2-Cys12 ring was explored by adding two residues at the N-terminal end. This extension could augment ligand affinity for r/mC3 in several ways: first, it could assist sector 388-393 to retain the conformation seen in the crystallographic complex W4A9:hC3; even if sector 388-393 were displaced, the extension might form novel interactions, replacing the disrupted hydrogen-bonds between residues 1 and 2 and Asn390. A diserine extension was used to exploit the hydrogen-bonding capacity of the serine side chains. Starting from the N-terminal end of the original compound (position 1), the inserted serines are denoted "Ser0" and "Ser-1" in what follows.

The displacement of sector 388-393 was somewhat smaller relative to other non-primate complexes (runs S-1S0:R and S-1S0:M in Table 4. Notably, the hydrogen bond Cys2 NH-Asn390 OD was maintained and a novel, stable hydrogen bond was formed between the main chain of Ser0 and Asn390 (FIG. 1E, FIG. 8C and Table 5D). The first hydrogen bond is observed for the first time in simulations of a non-primate complex, and is reproduced in all four non-primate runs of this generation (Table 5D); the second hydrogen bond is new, due to the extension.

Some interactions were reduced relative to the W4A9: hC3 complex, particularly non-polar contacts of ligand residues Trp4 and Cys12 with Asn390 and His393 and of Asp6, Trp7 with Pro459 (FIGS. 6-7 and 8B); on the other hand, residue Ser-1 formed novel contacts with sector 371-376 (FIGS. 1(E-F), 8C-D). Nevertheless, the similarity between the diserine extension rC3 and mC3 complexes and the W4A9:hC3 complex is high, and is additionally verified by residue interaction free-energy difference values which are close to zero [FIG. 2(A, B)].

The computed affinities of the diserine analog for non-primate C3 were −54.8 to −56.7 kcal/mol, near the affinity of W4A9 for hC3 and by ~9-11 kcal/mol stronger than its affinity for rC3.

Human Complexes.

Second Generation.

Simulations were performed with R1, the strongest non-primate binding analog in this group (runs R1H1/2 in Table 5B). All interactions of the human complex W4A9:hC3 were reproduced [FIGS. 1(A, B) and 3A]. Furthermore, the Arg1-Asp349 salt bridge (FIG. 1A) was always present, and intermolecular side chain interactions of Arg1 with Pro347, Asp349 and Ser388, or Va13, Gln5 with Asp491, were slightly improved.

The computed affinity for hC3 is −59.3 kcal/mol, improved by ~−3 kcal/mol relative to W4A9 (Table 3). Notably, this is mainly due to the polar component, reflecting the contribution to stability due to the Arg1-Asp349 salt bridge.

Third Generation.

Analog W1, which exhibited the strongest affinity and best solubility was further studied. The Trp1 side chain interacted frequently with His10 and Leu492 (FIG. 1D) in both runs (W1:H1 and W1:H2); furthermore, Asp6 formed an electrostatic interaction with Arg459. Despite these additional interactions, all interactions of the human complex W4A9:hC3 were reproduced [FIGS. 1(C, D) and 3B] and the computed hC3 affinity was −55.7 kcal/mol, by ~4 kcal/mol weaker than the affinity of R1 (second generation) and comparable to the W4A9 affinity (−56 kcal/mol). These results suggest that the Trp1 side chain did not fully exploit its interaction capabilities, presumably due to the lack of a suitable binding pocket in its proximity (unlike Trp4 and Trp7, which intercalate between specific protein sectors).

In both complexes, a n-cation Arg11-Trp13 interaction was observed. In the complex W13:H, this interaction seemed to interfere with the Cys2-Asn390 hydrogen bond, resulting in a somewhat reduced affinity (−51.1 kcal/mol; Table 6), relative to the W4A9 complex (−56 kcal/mol). In complex W1W13:H, the same interaction seemed to stabilize the ligand conformation, facilitating non-polar interactions of Trp1 with residues Pro347, Ser388, Asn390, Leu454 and Leu492 (FIGS. 6-7); the computed W1W13 affinity was considerably increased (−61.4 kcal/mol). Apart from the intramolecular n-cation interaction, Trp13 was solvent-exposed on its other side, without making interactions with the protein.

Fourth Generation.

The key Cys2-Asn390 interaction was retained in both runs (S-1S0:H1/2 in Table 5D). Furthermore, the main-chain of Ser0 formed an additional hydrogen bond with Asn390; this bond was somewhat less stable than the corresponding interaction in the non-primate complexes (Table 5D), presumably due to the increased proximity of Asn390 to the ligand (FIG. 8A-B). In the second run, the intermolecular hydrogen bonds of His10 were not well reproduced (Table 5D, FIG. 8A), resulting in less favorable polar interactions compared to the W4A9:hC3 complex (FIG. 3C). The predicted affinity (−57.3 kcal/mol) is somewhat stronger relative to W4A9, albeit not as good as for the R1 analog (Table 3).

To summarize, the simulations suggested that the diserine analog may be a promising "dual-specificity" inhibitor, estimated to bind with similar strength both human and non-primate C3. In the simulations, the analog forms intermolecular interactions with C3 via its main-chain moiety, whereas the serine side chains remain mostly solvent-exposed. Thus, possibly avenues to improve this compound could be to optimize the side-chains of the extension, and/or increase further the extension length.

Example 2

Biological Assays

Peptide Synthesis.

Compstatin family peptides were custom synthesized and characterized using liquid chromatography-mass spectrometry by Abgent Inc. (San Diego, Calif., USA). The parent compstatin peptide (control) was purchased either from Abgent (for C3b, C5b-9 ELISAs and hemolytic assay) or from TOCRIS Bioscience (Bristol, UK; for RPE cell-based assay). The peptides were acetylated at the N-terminus and amidated at the C-terminus, with the exception of parent compstatin control, which was not acetylated at the N-terminus. All peptides were cyclized through a disulfide bridge between Cys2 and Cys12. Peptides containing methylated tryptophan (methylated-Trp) were synthesized using Fmoc-1-methyl-DL-tryptophan, and the resulting mixture of peptides containing D-methylated-Trp and L-methylated-Trp were subsequently purified to obtain peptides containing only the L-enantiomer. Additional characterization of the peptides was performed using HPLC and NMR. The peptide sequences are shown in Table 7.

TABLE 7

| Peptide | Sequence[a] -10 123 | 456789 | 0123[c] | Molec. Mass[b] | $IC_{50}$ (mM) | SEQ ID NO: |
|---|---|---|---|---|---|---|
| | N-terminus modification analogs | | | | | |
| I | Ac- RCV | WQDWGA | HRCT-$NH_2$ | 1656.0 | 0.25 | 5 |
| II | Ac- meWCV | WQDWGA | HRCT-$NH_2$ | 1700.4 | 0.24 | 6 |
| III | Ac- RCV | meWQDWGA | HRCT-$NH_2$ | 1669.8 | 0.30 | 7 |
| | N-terminus extension analogs | | | | | |
| IV | Ac-SS-ICV | WQDWGA | HRCT-$NH_2$ | 1787.7 | 0.33 | 8 |
| V | Ac-WW-RCV | WQDWGA | HRCT-$NH_2$ | 2029.0 | 0.46 | 9 |
| VI | Ac-RS-ICV | meWQDWGA | HRCT-$NH_2$ | 1870.6 | 0.62 | 10 |
| VII | Ac-RS-RCV | meWQDWGA | HRCT-$NH_2$ | 1913.4 | 0.47 | 11 |
| VIII | Ac-SS-RCV | meWQDWGA | HRCT-$NH_2$ | 1844.3 | 0.42 | 12 |
| Peptide 2.1 | Ac- ICV | meWQDWG{Nal}HRCT-$NH_2$ | | | | 14 |
| Peptide 2.2 | Ac- ICV | WQDWG{Nal}HRCT-$NH_2$ | | | | 15 |
| Peptide 2.3 | Ac- ICV | WQDWG{Rea}HRCT-$NH_2$ | | | | 16 |
| Peptide 2.4 | Ac- ICV | WQDWG{Aal}HRCT-$NH_2$ | | | | 17 |
| Peptide 2.5 | Ac- ICV | WQDWG{Sea}HRCT-$NH_2$ | | | | 18 |
| Peptide 3.1 | Ac-ER-ICV | WQDWGA | HRCT-$NH_2$ | | | 19 |
| Peptide 3.2 | Ac-NN-LCV | WQDWGA | HRCT-$NH_2$ | | | 20 |
| Peptide 3.3 | Ac-NR-LCV | WQDWGA | HRCT-$NH_2$ | | | 21 |
| Peptide 3.4 | Ac-RS-ICV | WQDWGA | HRCT-$NH_2$ | | | 22 |
| Peptide 4.1 | Ac-ER-ICV | WQDWG{Nal}HRCT-$NH_2$ | | | | 23 |
| Peptide 4.2 | Ac-NN-LCV | WQDWG{Nal}HRCT-$NH_2$ | | | | 24 |
| Peptide 4.3 | Ac-NR-LCV | WQDWG{Nal}HRCT-$NH_2$ | | | | 25 |
| Peptide 4.4 | Ac-RS-ICV | WQDWG{Nal}HRCT-$NH_2$ | | | | 26 |
| Peptide 4.5 | Ac-ER-ICV{Nal}QDWG{Nal}HRCT-$NH_2$ | | | | | 27 |
| Peptide 4.6 | Ac-NN-LCV{Nal}QDWG{Nal}HRCT-$NH_2$ | | | | | 28 |
| Peptide 4.7 | Ac-NR-LCV{Nal}QDWG{Nal}HRCT-$NH_2$ | | | | | 29 |
| Peptide 4.8 | Ac-RS-ICV{Nal}QDWG{Nal}HRCT-$NH_2$ | | | | | 30 |
| Peptide 5.1 | Ac-SS ICV{Nal}QDWGA | | HRCT-$NH_2$ | | | 31 |

TABLE 7-continued

| Peptide | -10 | Sequence[a] 123 456789 | 0123[c] | Molec. Mass[b] | IC$_{50}$ (mM) | SEQ ID NO: |
|---|---|---|---|---|---|---|
| Peptide 5.2 | Ac-RS | ICV{Nal}QDWGA | HRCT-NH$_2$ | | | 32 |
| Peptide 5.3 | Ac-RS | RCV{Nal}QDWGA | HRCT-NH$_2$ | | | 33 |
| Peptide 5.4 | Ac-SS | RCV{Nal}QDWGA | HRCT-NH$_2$ | | | 34 |
| Peptide 5.5 | Ac-ER | ICV{Nal}QDWGA | HRCT-NH$_2$ | | | 35 |
| Peptide 5.6 | Ac-NN | LCV{Nal}QDWGA | HRCT-NH$_2$ | | | 36 |
| Peptide 5.7 | Ac-NR | LCV{Nal}QDWGA | HRCT-NH$_2$ | | | 37 |
| Peptide 5.8 | Ac-DN | FCV{Nal}QDWGA | HRCT-NH$_2$ | | | 38 |
| Peptide 5.9 | Ac-NQ | DCV{Nal}QDWGA | HRCT-NH$_2$ | | | 39 |
| Peptide 5.10 | Ac-NR | DCV{Nal}QDWGA | HRCT-NH$_2$ | | | 40 |
| Peptide 5.11 | Ac-ER | WCV{Nal}QDWGA | HRCT-NH$_2$ | | | 41 |
| Peptide 5.12 | Ac-NN | NCV{Nal}QDWGA | HRCT-NH$_2$ | | | 42 |
| Peptide 6.1 | Ac-SS | ICV YQDWGA | HRCT-NH$_2$ | | | 43 |
| Peptide 6.2 | Ac-RS | ICV YQDWGA | HRCT-NH$_2$ | | | 44 |
| Peptide 6.3 | Ac-RS | RCV YQDWGA | HRCT-NH$_2$ | | | 45 |
| Peptide 6.4 | Ac-SS | RCV YQDWGA | HRCT-NH$_2$ | | | 46 |
| Peptide 6.5 | Ac-ER | ICV YQDWGA | HRCT-NH$_2$ | | | 47 |
| Peptide 6.6 | Ac-NN | LCV YQDWGA | HRCT-NH$_2$ | | | 48 |
| Peptide 6.7 | Ac-NR | LCV YQDWGA | HRCT-NH$_2$ | | | 49 |
| Peptide 6.8 | Ac-DN | FCV YQDWGA | HRCT-NH$_2$ | | | 50 |
| Peptide 6.9 | Ac-NQ | DCV YQDWGA | HRCT-NH$_2$ | | | 51 |
| Peptide 6.10 | Ac-NR | DCV YQDWGA | HRCT-NH$_2$ | | | 52 |
| Peptide 6.11 | Ac-ER | WCV YQDWGA | HRCT-NH$_2$ | | | 53 |
| Peptide 6.12 | Ac-NN | NCV YQDWGA | HRCT-NH$_2$ | | | 54 |
| Control analogs | | | | | | |
| IX | Ac- | ICV WQDWGA | HRCT-NH$_2$ | 1614.0 | 0.24 | 13 |
| Parent | | ICV VQDWGH | HRCT-NH$_2$ | 1549.8 | | 1 |

[a]Tryptophans methylated at the indole amide position are shown as meW. The peptides are cyclized with a disulfide bridge between C2 and C12. Ac denotes acetylation and NH$_2$ denotes amidation.
[b]From mass spectrometry.
[c]Numbering indicates sequence position, starting from position -1 and ending at position 13.
Nal refers to 1-naphthylalanine or 2-naphthylalanine in this Table.

C3b and C5b-9 ELISAs.

Inhibition of the complement alternative pathway (AP) by compstatin family peptides was assayed by ELISA. Peptides were dissolved in phosphate buffered saline (PBS, 150 mM). Initial peptide concentrations were calculated using the Beer-Lambert Law with an extinction coefficient of 5,500 (1/M·cm) for Trp and 5,470 (1/M·cm) for methylated-Trp present in the sequence, at 280 nm. Nunc Maxisorp 96-well plates were coated with 1 μg lipopolysaccharides (LPS) from *Salmonella enteriditis* for ~16 h at room temperature. Plates were washed three times with PBS/0.05% Tween-20 (PBS-T) between each step. Plates were blocked with 4% bovine serum albumin (BSA) in PBS-T for 1 h at 37° C. Serial peptide dilutions were performed in 96-well plates, using gelatin veronal-buffered saline with 5 mM MgCl2 and 10 mM EGTA (GVBS-MgEGTA). Normal human serum (Complement Technology Inc., Tyler, Tex., USA) was diluted in GVBS-MgEGTA and mixed with compstatin serial dilutions to a final concentration of 30%. Serum diluted in GVBS-MgEGTA and GVBS (containing 20 mM EDTA) were used as positive and negative controls for complement activation, respectively. Dilutions were preincubated for 15 minutes at room temperature, transferred to ELISA plates, and incubated for 1 h at 37° C. Generation of C3b and C5b-9 were assayed using horseradish peroxidase (HRP)-conjugated anti-C3 (MP Biomedicals, Solon, Ohio, USA) and anti-05b-9 aEll (Abcam, Cambridge, Mass., USA), respectively. Plates were washed and incubated with either anti-C3-HRP (1:5000 in 1% BSA/PBS-T) or anti-05b-9 (1:1000 in 1% BSA/PBS-T) for 1 h at 37° C. For C5b-9 detection, primary antibody incubation was followed by incubation with anti-mouse-HRP (BioRad, Hercules, Calif., USA) for 1 h at 37° C. (1:5000 in 1% BSA/PBS-T). Bound C3b and C5b-9 were quantified using a 3,3',5,5'-tetramethylbenzidine substrate solution containing urea hydrogen peroxide in 0.11 M sodium acetate buffer, followed by a 1 N $H_2SO_4$ acid stop. Plates were measured spectrophotometrically at 450 nm. Percent inhibition of C3b and C5b-9 deposition was plotted against peptide concentration and the data was fitted to a logistic dose response curve with Prism software (GraphPad, San Diego, Calif., USA) to determine $IC_{50}$ values.

Hemolytic Assays.

Inhibition of complement was also measured via lysis of erythrocytes. Rabbit erythrocytes (Complement Technology Inc., Tyler, Tex., USA) were washed in PBS and resuspended in veronal-buffered saline with 5 mM $MgCl_2$ and 10 mM EGTA (VBS-MgEGTA). Peptide and serum dilutions were prepared as described above, and $1 \times 10^7$ erythrocytes were added to each serum/peptide mixture. Erythrocytes diluted in sterile deionized water and in VBS-MgEGTA were used as positive and negative controls for lysis, respectively. Plates were incubated for 20 minutes at 37° C., and centrifuged at 2500×g for 10 minutes. Supernatants were diluted 1:2 and absorbance was measured at 405 nm.

RPE Cell Culture.

The in vitro drusen biogenesis model was employed. Human fetal RPE cells (Advanced Bioscience Resources, Alameda, Calif.) were cultured on Millipore HA porous supports (Millipore, Cat # PIHA 01250) in Miller medium (Maminishkis et al., 2006) supplemented with 5% fetal calf serum (FCS). Cultures derived from three different donor eyes were employed. Cells were rinsed with warm, sterile PBS and the insert membrane was excised with a scalpel and cut into small (~4 mm²) pieces which were placed in wells of a 96-well plate. To minimize effects of inter-culture variability, samples prepared from a single membrane were utilized for each experiment. The samples were rinsed in PBS and then exposed individually to the library of compstatin family peptides at 1 µM in FCS-free Miller medium containing 10% human complement serum (Innovative Research, Cat # IPLA-CSER AB, Lot # L12402). In preliminary experiments, compstatin family Peptides I, III, VI, VII, VIII, IX, and Parent (Table 7), were tested in the RPE cell assay at 100 µM and titrated by C5b-9 ELISA over a concentration range of 0.04-130 µM. The 1 µM concentration employed was selected based on these results, showing it to be in the linear range of inhibitory concentrations. Also from this assessment, Peptide VI, as well as Peptides I and III, were selected for further studies. Peptides I and III were chosen for comparative studies to Peptide VI, because they contain an arginine residue at position 1. The goal was to determine whether peptides containing arginine at position −1 (Peptide VI) or at position 1 (Peptides I and III) were potent complement inhibitors using the RPE cell assay and had improved aqueous solubility compared to previously known potent analogs. Negative control cells were exposed to Miller medium+5% FCS; positive control cells were exposed to Miller medium+10% human complement serum without inhibitory peptides. Experimental and control medium/inhibitor solutions were pre-mixed on a rocker at room temperature for 30 min, then warmed to 37° C., prior to placement on the samples and incubation for ~24 hrs at 37° C. in a 7.0% $CO_2$ incubator. Following the incubation period, the medium was removed and stored frozen prior to ELISA analysis. The cell/membrane samples were rinsed in PBS, fixed in cold 4% paraformaldehyde (PFA) in PBS for 20 min, and stored in 0.4% PFA until use in immunohistochemical assays.

Immunohistochemistry.

Fixed samples were rinsed several times in PBS, embedded in 10% agarose (Type XI, Sigma-Aldrich, Cat # A3038) and sectioned at 100 µm on a vibratome. Sections were blocked with normal donkey serum (1/20 in PBT: PBS containing 0.5% bovine serum albumin and 0.1% Triton X-100) overnight at 4° C. The sections were then co-incubated in two primary antibodies (polyclonal goat anti-ApoE, Millipore Cat # AB947; 1/1000 in PBT, and mouse monoclonal anti-05b-9 aEll, Dako Cat # M0777; 1/200 in PBT) overnight at 4° C., then rinsed in PBT and co-incubated in secondary antibodies (Alexa Fluor 546-conjugated donkey anti-goat IgG and Alexa Fluor 488-conjugated donkey anti-mouse IgG, both 1/200 in PBT; Life Technologies Cat # A-11056 and # A-21202) overnight at 4° C. Sections were rinsed in PBT, stained with Hoechst 33342 (Life Technologies Cat # H3570), and mounted on slides with Prolong Gold (Life Technologies Cat # P36930).

Confocal Imaging and Analysis.

Figure 9:
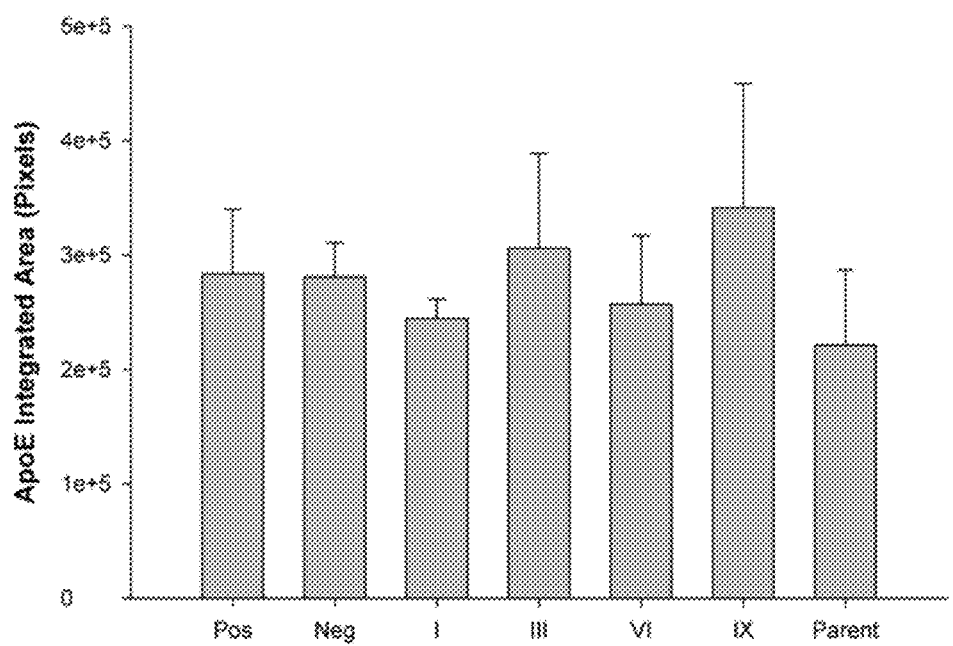
FIG. 9 shows mean areas of ApoE-immunolabeled deposits for the seven treatment conditions analyzed (+/−S.E.M.). Analysis of the data using a one-way ANOVA identified no statistically significant difference in the deposit load among the treatment groups [$F(6,14)=0.363$, $p=0.89$].

Samples were imaged on an Olympus FV1000 confocal laser scanning microscope. A total of 154 single-plane images were acquired at a resolution of 1024×768 pixels and the digital image files were saved in 24-bit tiff format. Digital image analysis was performed with MetaMorph software (Molecular Devices, Sunnyvale, Calif.). For the analysis, a standard measurement region, which included both the RPE cell monolayer and all of the adjacent sub-cellular deposits, was applied to each image. The Set Threshold Color Tool was utilized to analyze each color channel separately; the threshold tool creates a boundary around the objects being measured (i.e., sub-cellular deposits) on the basis of color intensity. The upper threshold was set so that the entire deposit area was selected; then the lower threshold was set to exclude background fluorescence. These settings allowed the isolation of deposit-associated fluorescence and independent measurement of the area and intensity of C5b9 immunofluorescence in the green channel and ApoE immunofluorescence in the red channel (see Table 8). The ApoE threshold was standardized using the negative control samples. The positive control samples, which contained the highest levels of C5b-9 immunoreactivity, were used to standardize the C5b-9 threshold. Positive and negative control standards and the associated thresholds were independently established for each cell line for each experiment. The sum of the pixel intensities within the threshold limits (integrated area) was used in statistical analyses. For each image, the integrated area of C5b-9 was normalized to the ApoE area and the ratio of C5b-9/ApoE intensity was expressed as a percentage of the positive control sample. Statistical analysis of the data from each of the treatment groups was performed using a one-way ANOVA calculated using Tukey's test for multiple comparisons. A p value <0.05 was considered to be of statistical significance. To assess variability in the amounts of sub-cellular deposits, the ApoE fluorescence data was analyzed and area values for the seven treatment groups were compared. This analysis demonstrated that there was not a statistically significant difference in the ApoE deposit load among the seven treatment groups examined [$F(6,14)$=0.363, p=0.89] (FIG. 9).

TABLE 8

Values for deposit-associated ApoE (red channel) and C5b9 (green channel) immunofluorescence expressed as Integrated Area (number of pixels within threshold limits).

| Treatment | RPE 081309 | | RPE 072810 | | RPE 020207 | |
|---|---|---|---|---|---|---|
| | Green (C5b9) | Red (ApoE) | Green (C5b9) | Red (ApoE) | Green (C5b9) | Red (ApoE) |
| NEG | 1227 | 271921 | 0 | 270631 | 11044 | 471483 |
| | 0 | 115310 | 0 | 203638 | 350 | 316249 |
| | 0 | 257144 | 0 | 228310 | 1485 | 295858 |
| | 0 | 236157 | 0 | 282685 | 2109 | 277092 |
| | 667 | 334368 | 0 | 460238 | 1332 | 326242 |
| | 0 | 289352 | 0 | 268701 | | |
| | 0 | 228958 | 0 | 547973 | | |
| | 165 | 193082 | | | | |
| | 217 | 234147 | | | | |
| | 134 | 185392 | | | | |
| POS | 195975 | 200823 | 79644 | 234048 | 161028 | 257788 |
| | 156381 | 187516 | 178100 | 249431 | 257593 | 461853 |
| | 150140 | 400977 | 92615 | 180108 | 432669 | 518787 |
| | 123568 | 96618 | 75700 | 126290 | 474049 | 392046 |
| | 304872 | 141348 | 163413 | 336703 | 416701 | 349999 |
| | 293779 | 92994 | 152674 | 362497 | | |
| | 316743 | 267384 | 52233 | 105424 | | |
| | 204554 | 346549 | | | | |
| | 244514 | 279570 | | | | |
| | 113386 | 193596 | | | | |
| Parent | 103729 | 133476 | 134879 | 196284 | 304292 | 391731 |
| | 90563 | 115233 | 58962 | 155130 | 249947 | 221704 |
| | 179821 | 193229 | 53218 | 177885 | 422922 | 554772 |
| | 90919 | 216139 | 39859 | 67316 | 170221 | 255922 |
| | 24316 | 41510 | 111725 | 357499 | 263572 | 304692 |
| | 79906 | 130991 | 73645 | 244396 | | |
| | 132786 | 74119 | 142326 | 835731 | | |
| | 64906 | 38401 | | | | |
| | 92050 | 159702 | | | | |
| | 132751 | 113375 | | | | |
| I | 237321 | 306320 | 29212 | 268039 | 176716 | 153503 |
| | 132425 | 242578 | 90290 | 366235 | 242797 | 291725 |
| | 118233 | 222388 | 115001 | 217137 | 191127 | 339862 |
| | 63000 | 190384 | 52273 | 372133 | 88155 | 263661 |
| | 107777 | 233173 | 52677 | 199902 | 92684 | 161177 |
| | 131264 | 244426 | 31245 | 142671 | | |
| | 132259 | 350286 | 34314 | 115426 | | |
| | 144301 | 396916 | | | | |
| | 110544 | 276665 | | | | |
| | 35076 | 285904 | | | | |
| III | 54578 | 223189 | 15147 | 290849 | 200200 | 523907 |
| | 34684 | 289842 | 28013 | 379390 | 216413 | 544722 |
| | 24847 | 103719 | 16543 | 243662 | 140704 | 531422 |
| | 30140 | 133246 | 3046 | 234223 | 101057 | 425980 |
| | 38691 | 164727 | 14768 | 397343 | 54519 | 323152 |
| | 58008 | 165315 | 9070 | 154739 | | |
| | 36286 | 242843 | 6313 | 168982 | | |
| | 36489 | 180332 | | | | |
| | 53639 | 226904 | | | | |
| | 33736 | 311378 | | | | |
| VI | 16992 | 121449 | 1723 | 76377 | 86318 | 470242 |
| | 29873 | 140408 | 9908 | 129610 | 70370 | 382683 |
| | 33617 | 470247 | 2073 | 133868 | 77727 | 335606 |
| | 22663 | 173917 | 814 | 156501 | 91254 | 317390 |
| | 79150 | 355786 | 9705 | 544668 | 59969 | 313633 |
| | 71140 | 285517 | 12657 | 515781 | | |
| | 41761 | 290355 | 4083 | 274517 | | |
| | 40086 | 213096 | | | | |
| | 59931 | 240676 | | | | |
| | 45701 | 210462 | | | | |
| IX | 46031 | 177430 | 26592 | 507947 | 39379 | 318144 |
| | 53416 | 203692 | 42861 | 555720 | 55410 | 170845 |
| | 44126 | 214342 | 33836 | 1006424 | 49677 | 304862 |
| | 31556 | 161833 | 48984 | 754923 | 61352 | 123360 |
| | 72956 | 382437 | 41284 | 753283 | 149508 | 400680 |
| | 28250 | 233287 | 59567 | 441362 | | |
| | 31684 | 235044 | 19401 | 274320 | | |
| | 34381 | 246857 | | | | |
| | 23565 | 94624 | | | | |
| | 18200 | 102936 | | | | |

Soluble C5b-9 ELISA of the RPE Cell-Based Assay Medium.

Experimental medium solutions were diluted 1/625 in assay diluent and quadruplicate ELISAs were performed using an OptEIA C5b-9 ELISA kit (BD Biosciences, Cat #558315). Plates were read at 450 nm, with absorbance at 570 nm subtracted for wavelength correction, on a BioRad Benchmark plate reader. C5b-9 concentrations were calculated using a standard curve generated using purified human C5b-9. Data was expressed as a percentage relative to the positive (human serum only) control. Means and standard errors for data from the three RPE donor cells were calculated and graphed using SigmaPlot 11.0 (Systat Software, San Jose, Calif.), and one-way ANOVA was calculated using Tukey's test for multiple comparisons.

RP-HPLC Study.

The effect of the hydrophobic content of compstatin family peptides on relative lipophilicity was evaluated using RP-HPLC, a widely applied indirect technique for the determination of the lipophilicity of drugs and drug candidates. The determination of log P by RP-HPLC is based on the measurement of the retention factor k between the mobile and stationary phase (Eq. 7) of the investigated compound:

$$\log k = \log \frac{t_R - t_0}{t_0} \quad (7)$$

where $t_R$ is the retention time of the analyte, and to is the elution time of an unretained analyte. The logarithm of the retention factor is linearly correlated with the logarithm of the partition coefficient $$\log P = a \log k + b \quad (8).$$

where a and b are the slope and intercept of the linear equation.

The determination of log P values requires calibration using structurally related compounds, and is beyond the scope of this study. Instead the log k values were used to indicate the relative lipophilicities of this compstatin peptide family.

Figure 10:
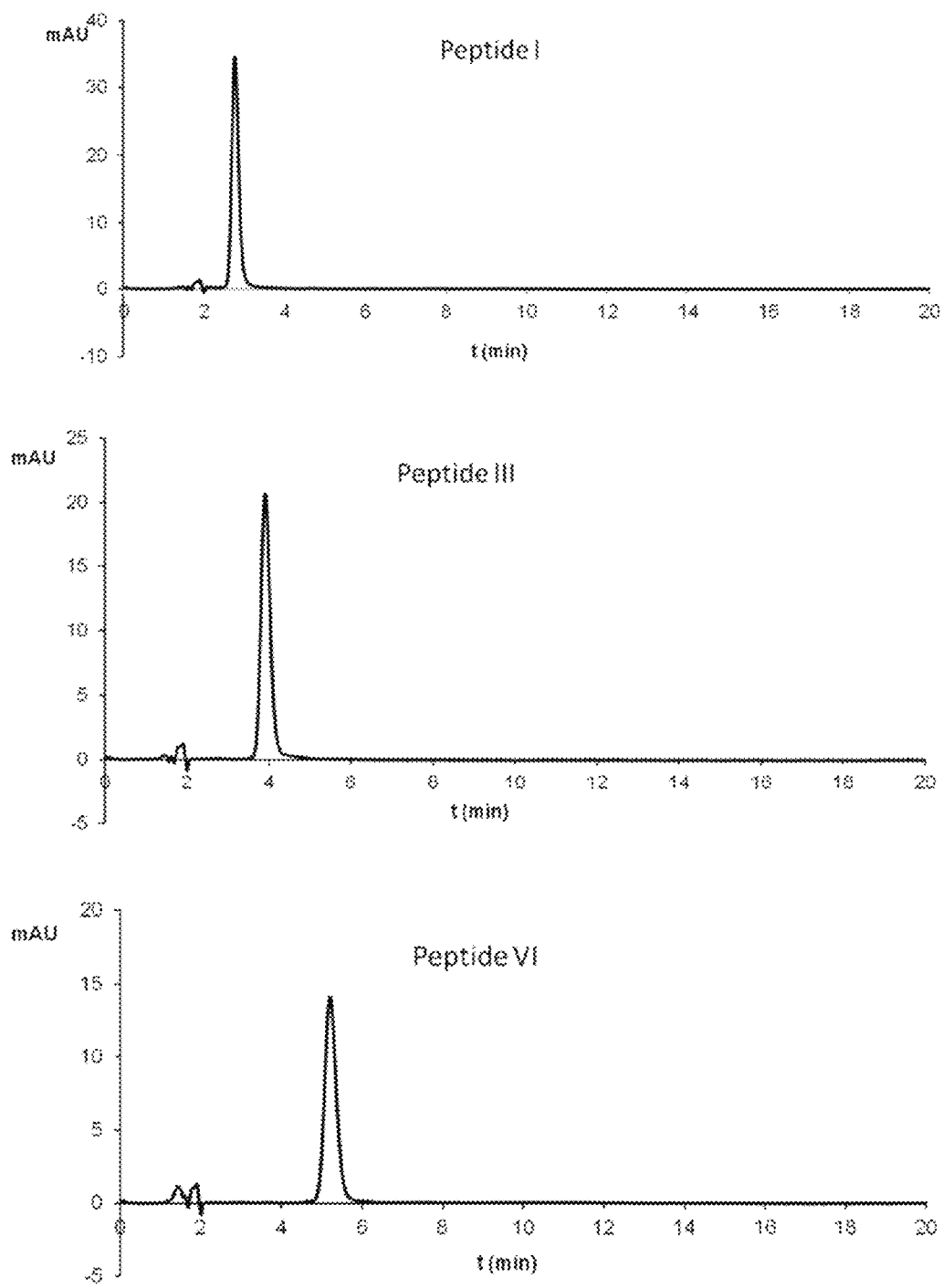
FIG. 10 shows HPLC chromatogram of the compstatin family peptides, used to perform the C3b and C5b-9 ELISAs, and hemolytic assays.
Figure 10:
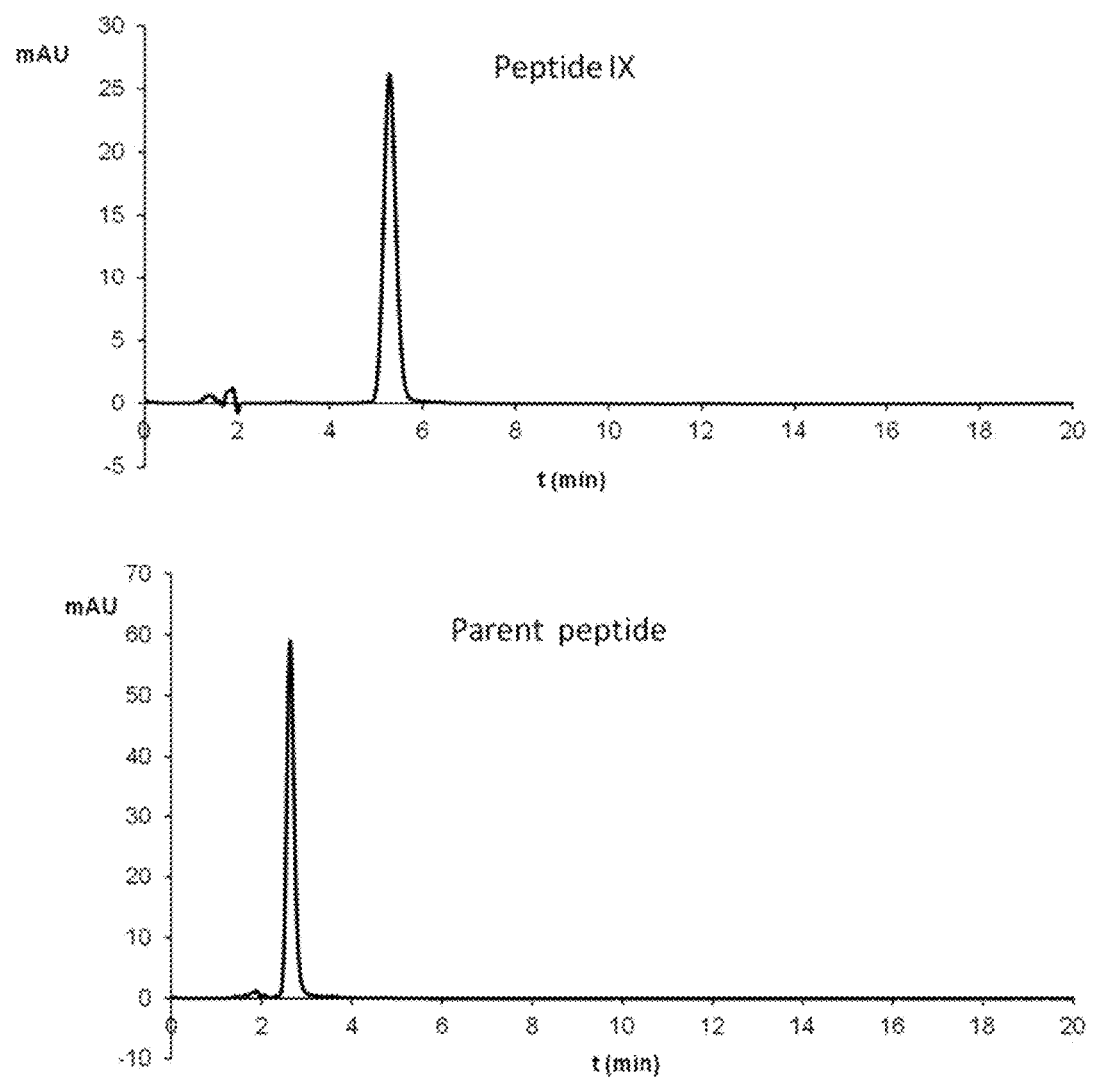

HPLC experiments were carried out using an Agilent 1100 HPLC with UV detection at 280 nm at 25° C. Separations were performed on a Waters (Milford, Mass.) 4.6× 150 mm XTerra MS C18 column with 5 μm pore size using a mobile phase of A: 10 mM phosphate buffer pH=7.4 containing 1% TFA, and B: acetonitrile. The purity of the peptides was verified by an isocratic separation at 28% B and a flow rate of 1 mL/min. Solutions containing 0.6-0.8 mg/mL of Peptides I, III, VI, IX and the parent peptide were prepared in methanol and diluted 5-times with the eluent. All five peptides eluted as single peaks indicating a high degree of purity (FIG. 10).

Figure 11:
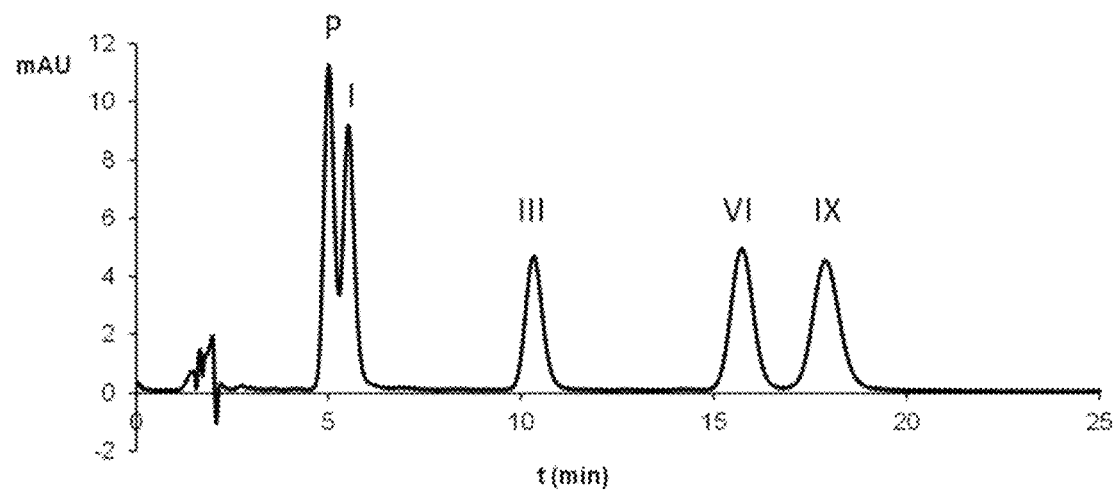
FIG. 11 shows HPLC separation showing the relative lipophilicities of the compstatin family peptides used to perform the C3b and C5b-9 ELISAs, and hemolytic assays. P denotes parent.

For the determination of the relative lipophilicities a solution containing each of the peptides was prepared from the stock solutions and injected in triplicate. Isocratic elution at 24% B and a flow rate of 1 mL/min resulted in separation of the Peptides I, III, VI, IX and Parent (FIG. 11). A 0.5 mg/mL solution of aspartic acid was used as the unretained analyte for the determination of the column dead time, 1.439±0.003 min.

Sodium phosphate monobasic, aspartic acid, methanol and acetonitrile were obtained from Fisher Scientific (Pittsburgh, Pa.). Trifluoroacetic acid (TFA) was purchased from Acros (Geel, Belgium). HPLC-grade Burdick and Jackson water was used for the HPLC analysis (Morristown, N.J.).

NMR Study.

NMR spectroscopy was used to confirm peptide purity. Although the HPLC separations suggested that the peptides were of high purity as a single chromatographic peak was observed for each sample, the possibility of coelution of the desired peptide and structurally related impurities cannot be discounted. Because of the sensitivity of chemical shifts to subtle structural changes, $^1$H NMR spectroscopy provides an excellent measure of peptide purity. $^1$H NMR spectra were acquired for separate solutions of each peptide prepared by dissolving 1 mg samples into 600 μL 50 mM phosphate buffer containing 10% $D_2O$ and 0.4 mM 2,2-dimethyl-2-silapentane-5-sulfonate-$d_6$ sodium salt (DSS) as a reference compound. The pH of the phosphate buffer was set to 6.5 using NaOD. $^1$H NMR spectra were recorded at 22° C. with a Bruker Avance spectrometer operating at $^1$H frequency of 600.01 MHz using a triple resonance inverse probe. Excitation sculpting was used for water suppression (Bruker pulse program zgesgp) (Hwang and Shaka, 1995). Spectra were collected into 32,768 points using 64 scans with a spectral window of 12 ppm, were processed in 65,536 points and multiplied with an exponential function equivalent to 0.5 Hz line broadening.

Deuterium oxide and NaOD were obtained from Cambridge Isotope Laboratories (Andover, Mass.), DSS was purchased from Sigma Chemical Company (St. Louis, Mo.). Water was HPLC grade from Burdick & Jackson (Honeywell, Morristown, N.J.).

The samples used to measure C3b and C5b-9 ELISAs and hemolytic lysis assays presented here (Peptides I, III, VI, IX, and Parent) were tested with HPLC and NMR, as discussed above and were found to be pure. The samples used for the RPE cell assays were from an older preparation and some appeared to have an impurity in HPLC experiments, which was not due to aggregates. The impurity populations of the old Peptides III and VI was estimated to be 15% and 33% using the HPLC chromatograms. Nevertheless, the relative potencies of the peptides were similar in C3b ELISA experiments using the two sample preparations.

Molecular Dynamics Simulations.

Molecular dynamics simulations were performed for Peptides III and VI, using explicit water solvation as described in Example 1, above. The molecular mechanics program CHARMM c35b5 was used for the simulations, with the CHARMM22 all-atom force field, including a CMAP backbone ϕ/ψ energy correction and indole parameters. Match server was used to derive the topology and parameters for the methylated tryptophan aromatic ring. As described above, loop C3 369-378 was unrestrained during the simulations since it is in proximity to the N-terminus of the peptides. For Peptide III, five 7-ns trajectories, starting from the same initial conformation with different equilibration times, were generated to a total of 35 ns simulation time. For Peptide VI, five 10-ns trajectories, starting from the same initial conformation with different equilibration times, were generated to a total of 50 ns simulation time. A total of 700 and 1,000 snapshots were analyzed for III and VI, respectively, extracted every 50 ps per trajectory. Percent occupancies were calculated for hydrogen bonds, as well as averaged intermolecular interaction energies, using homemade scripts. Molecular visualization was performed using the program VMD.

Initial Coordinates.

For Peptide III, the protein and ligand atoms (with the exception of Arg1 side chain), were initially placed according to the crystallographic structure of the Ac-V4W/H9A Compstatin: human C3 complex (PDB code 2QKI). The Arg1 side chain was placed with the aid of program SCWRL 4.0 (Krivov et al., 2009). For Peptide VI, the protein and ligand atoms (with the exception of the Arg-1 side chain) were initially placed at a structure taken from the simulation of the Ac-SS-ICVWQDWGAHRCT-NH$_2$ (SEQ ID NO:8): human C3 complex; that simulation itself was based on the crystallographic structure of the Ac-V4W/H9A Compstatin: human C3 complex (PDB code 2QKI). The employed structure had the lowest association free energy, as determined in the Molecular Mechanics-Generalized Born/Surface Area (MM-GBSA) approximation (see Eq. (4,5)). The Arg-1 side chain was placed with the aid of program SCWRL 4.0.

Computation of Interaction Free Energies of Protein and Ligand Residue Pairs.

The interaction free energies between two (R and R') residues are computed in the MM-GB/SA approximation using the equation:

$$\Delta G_{RR'}^{inte} \underbrace{\sum_{i \in R} \sum_{j \in R'} (E_{ij}^{Coul} + E_{ij}^{GB})}_{\Delta G_{RR'}^{polar}} + \underbrace{\sum_{i \in R} \sum_{j \in R'} E_{ij}^{vW} + \sigma \sum_{i \in R, R'} \Delta S_i}_{\Delta G_{RR'}^{nonpolar}}. \quad (9)$$

The first and second group of terms on the right-hand side of Eq. (9) describe, respectively, polar and nonpolar interactions between R and R', where Coul denotes Coulombic, GB denotes generalized Born, S is the solvent accessible surface area, and σ is a surface tension coefficient. In the calculations, R corresponded to a ligand residue and R' corresponded to a protein residue. To compute the GB term in Eq. (9), all protein and ligand atoms were included and set the charge to zero for atoms other than those belonging to residues RR', R and R', respectively, in each calculation of the terms on the right-hand side terms of Eq. (9). The last term contains the difference in solvent accessible surface areas of groups R and R' in the complex and unbound states. Free-energy values were averaged over all trajectories. The total interaction free energies were decomposed into polar and nonpolar interaction free energy components and the results are presented in two-dimensional maps.

In preliminary C3b ELISA experiments, Peptides I-IX demonstrated comparable potencies, within up to 3-fold ICH differences. For preliminary RPE cell culture experiments Peptides I, III, VI, VII, and VIII were selected (see Table 7), which contained Arg at the N-terminus or N-terminal extension, together with control Peptide IX and Parent. Based on the preliminary RPE cell assay studies a reduced number of peptides (Peptides I, III, and VI) was selected, for more quantitative C3b and C5b-9 ELISA, hemolytic assay, and RPE cell-based assay studies, together with control Peptide IX and Parent for comparison.

Analysis of Complement Inhibition by C3b and C5b-9 ELISA, and Erythrocyte Lysis Assay.

Figure 12C:
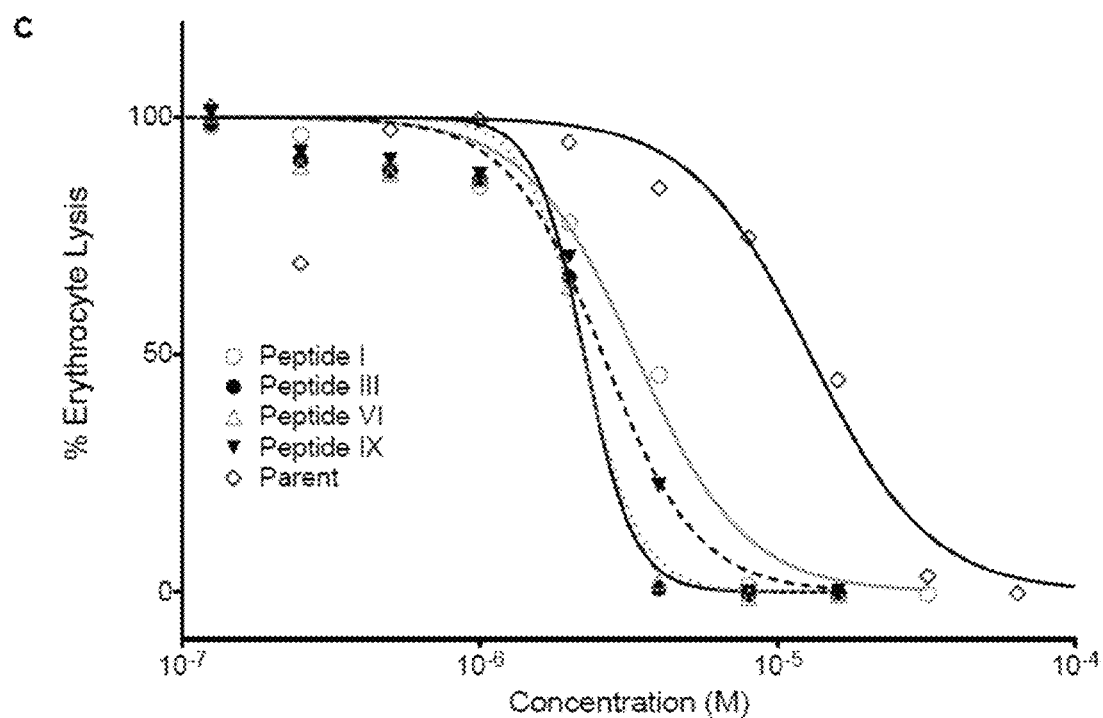

Since compstatin family peptides are known to selectively inhibit the complement alternative pathway (AP), ELISAs and erythrocyte lysis assays were performed to examine AP inhibition. In all assays, MgEGTA was used to chelate Ca' ions required for classical/lectin pathway complement activation, while providing Mg' necessary for AP activation. ELISAs allow for direct detection of C3b and C5b-9 formed during AP activation, while erythrocyte lysis assays provide a functional assessment of AP-mediated hemolysis in serum. FIG. 12 shows the C3b and C5b-9 ELISA and erythrocyte lysis data for Peptides I, III, VI, IX, and Parent. Table 9 summarizes the IC$_{50}$ values derived from the three different assays. Parent exhibited significantly less complement inhibition than all other peptides in all three assays. Newly-designed peptides (Peptides I, III, and VI) showed similar $IC_{50}$ values to Peptide IX, with Peptide I having a slightly higher $IC_{50}$ than the others in all cases. The relative potencies of the peptides, based on the measured ICH values, are consistent across all three assays (Peptide III~Peptide VI~Peptide IX>Peptide I>Parent). Based on the assay conditions used in this study, peptides inhibited C5b-9 formation with moderately better efficacy than formation of C3b, while slightly higher concentrations were necessary to inhibit AP-mediated hemolysis. It is also noteworthy that while C3b and C5b-9 inhibition by Parent was about 10- to 15-fold less than other peptides in ELISA, only a 4- to 6-fold difference was observed for hemolysis.

TABLE 9

Compstatin peptide $IC_{50}$ values from C3b and C5b-9 ELISA, and hemolytic assay.

| Peptide | $IC_{50}$ (μM)[a] | 95% confidence interval |
|---|---|---|
| C3b ELISA | | |
| I | 2.58 | 2.27-2.94 |
| III | 1.42 | 1.14-1.77 |
| VI | 1.74 | 1.50-2.02 |
| IX | 1.90 | 1.71-2.10 |
| Parent | 35.04 | 31.26-39.29 |
| C5b-9 ELISA | | |
| I | 2.02 | 1.66-2.46 |
| III | 1.07 | 0.85-1.36 |
| VI | 1.13 | 0.94-1.34 |
| IX | 1.04 | 0.80-1.33 |
| Parent | 18.61 | 15.65-22.14 |
| Hemolytic assay | | |
| I | 3.33 | 2.99-3.72 |
| III | 2.25 | 2.08-2.43 |
| VI | 2.23 | 2.05-2.42 |
| IX | 2.59 | 2.28-2.95 |
| Parent | 12.90 | 11.71-14.21 |

[a]Means from three independent experiments.

Complement Inhibition in the RPE Cell Model.

Exposure of RPE cell cultures to human serum leads to complement activation, as evidenced by the formation of subcellular deposit-associated C5b-9 (Johnson et al., 2011). Deposit-associated C5b-9 immunofluorescence was quantified using confocal microscopy and normalized to the fluorescence signal for ApoE (a ubiquitous deposit marker). In the presence of active compstatin family peptides, the amount of deposit-associated C5b-9 is reduced, proportionally to the peptide potencies. FIG. 13 shows examples of confocal immunofluorescence images of sub-RPE deposit-associated C5b-9.

Figure 14:
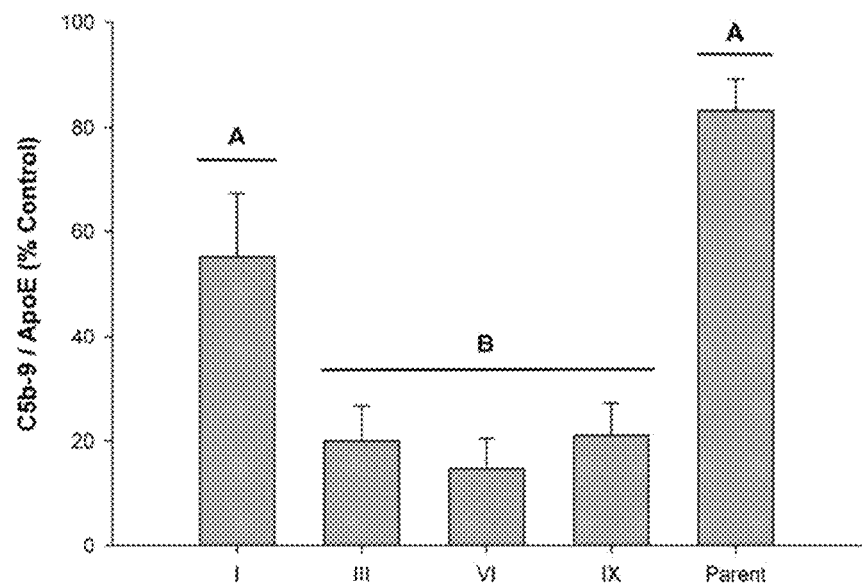
FIG. 14 shows confocal analysis of C5b-9 deposition. The ratio of deposit-associated C5b-9 fluorescence, a variable measure of complement activation, to ApoE fluorescence, a relatively constant deposit marker, is shown relative to the positive (human serum only) control. All peptides, except for the parent compound, significantly decrease complement activation. Although Peptide I decreases complement activation compared to the parent compound (group A), the difference is not statistically significant. Peptides III, VI, and IX (group B) are the most effective, and are all significantly different ($p<0.001$) from the parent compound and from peptide I. Bars represent the means (±S.E.M.) of the combined data from RPE cultures derived from three different donors.

Table 10 and FIG. 14 show the results of the RPE cell experiments for the aforementioned peptides. Peptides III, VI, and IX showed significantly more complement inhibition than Parent, reducing the C5b-9 deposits to approximately 15-20% of the positive control (human serum without inhibitory peptides). The effect of methylated-Trp4 in complement inhibition is evident when comparing the confocal imaging data of Peptides III and VI against those of Peptide I, which contains unmethylated Trp (Table 7). The confocal microscopy data reveal a large range of inhibition at the level of the sub-RPE deposits, and markedly discriminate the potencies of the peptides.

TABLE 10

Compstatin peptide inhibition from the RPE cell-based assay data.

| Peptide | Confocal Imaging % of positive control | Assay medium C5b-9 ELISA % of positive control |
|---|---|---|
| I | 55.27 (12.30)[a] | 61.37 (2.34)[a] |
| III | 19.98 (6.84) | 50.02 (0.82) |
| VI | 14.85 (5.61) | 44.60 (3.16) |
| Controls | | |
| IX | 21.11 (6.26) | 51.99 (2.21) |
| Parent | 83.19 (5.92) | 88.49 (0.76) |
| Negative (no human serum) | 0.34 (0.30) | 2.62 (0.79) |
| Positive (human serum) | 100 | 100 |

[a]Mean (S.E.M.).

The one-way ANOVA revealed a significant effect of the complement inhibitory peptides on deposit-associated C5b-9 formation [$F(5,12)=26.4$, $p<0.001$]. In the presence of Parent, deposit-associated complement activation was reduced to 83% of the positive control (mean±S.E.M.=83.2±5.9), but this difference was not statistically significant. However, Peptides I (55.3±12.3), III (20.0±6.8), VI (14.9±5.6), and IX (21.1±6.3), all exhibited significantly more inhibition, and all were statistically different from Parent ($p<0.001$). Peptides III, VI, and IX exhibited the greatest potencies and were not significantly different from each other.

Overall, the relative potencies derived from the RPE cell-based assay, C3b and C5b-9 ELISAs, and hemolytic assay experiments are in agreement and they follow the order Peptide III~Peptide VI~Peptide IX>Peptide I>Parent.

Analysis of Complement Inhibition by Soluble C5b-9 ELISA of the RPE Cell-Based Assay Medium.

Figure 15:
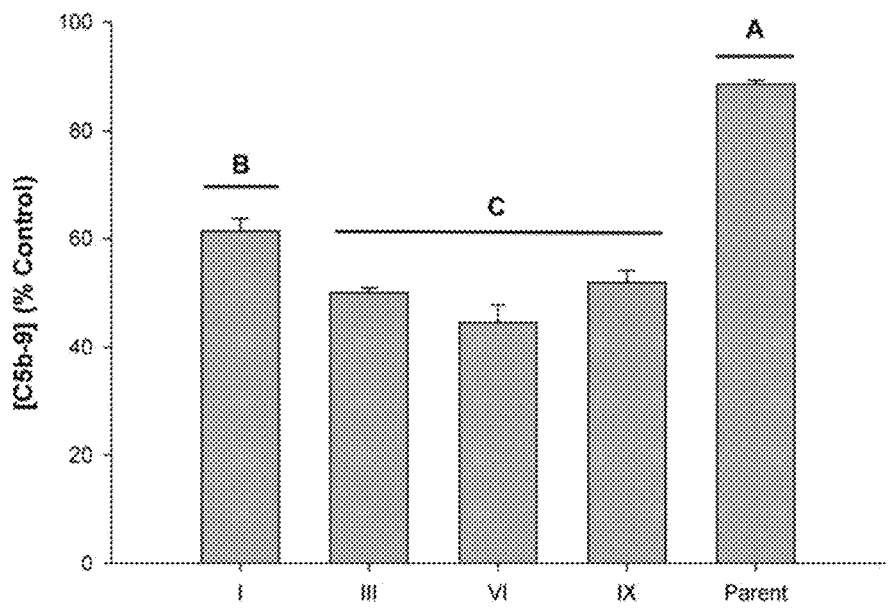
FIG. 15 shows C5b-9 ELISA. Relative to the positive control, all inhibitory peptides significantly decrease the amount of soluble C5b-9 present in the assay medium. Peptide I is more effective than the parent peptide, but less inhibitory than peptides III, VI, and IX which are the most effective inhibitors and are all significantly different ($p<0.001$) from the parent peptide and peptide I. Bars represent the means (±S.E.M.) of the combined data from RPE cultures derived from three different donors.

C5b-9 ELISAs of the RPE cell assay medium was also performed (Table 10, FIG. 15). A narrow range of inhibition was observed in these C5b-9 data, compared to the confocal microscopy data, likely reflecting background turnover of complement in the liquid phase as opposed to that directly associated with the sub-RPE deposits. Nevertheless, the one-way ANOVA showed a significant effect of the inhibitory peptides on soluble C5b-9 formation [$F(5,12)=144.2$, $p<0.001$]. This parallel analysis of soluble C5b-9 in the experimental medium solutions also showed the level of inhibition by Parent to be less than that of the experimental peptides. In the presence of Parent, C5b-9 levels were reduced to 89% of the positive control (mean±S.E.M.=88.5±0.76, $p=0.011$). All of the experimental peptides were more inhibitory, I (61.4±2.3), III (50.0±0.8), VI (44.6±3.2), IX (51.9±2.2) and all were statistically different from Parent ($p<0.001$).

Lipophilicity Measurements Using RP-HPLC.

RP-HPLC was used to measure the hydrophobicity/lipophilicity content of the compstatin family peptides. The retention of a compound in RP-HPLC depends on its hydrophobicity/lipophilicity content, and is correlated to the octanol-water partition ratio. Lipophilicity describes the partitioning of a compound between an aqueous and a lipidic/hydrophobic environment, and is an essential physicochemical parameter to determine pharmacokinetic behavior according to ADME (absorption, distribution, metabolism, excretion) characterization. Because the compstatin family peptides consist of a hydrophobic and a polar surface, their ability to bind to the hydrophobic cavity of C3, while maintaining a solvent-exposed face has been evaluated here as lipohilicity content, measured by RP-HPLC. In addition, lipohilicity is inversely proportional to aqueous solubility, and therefore can be used to estimate solubility of the peptides in their free (unbound) state.

Table 11 shows the retention times ($t_R$) and retention factors (k) for Peptides I, III, VI, IX, and Parent. These, and data for the whole set of peptides of Table 7, suggest that the major factors governing hydrophobicity of the peptides are the number of tryptophan and methylated-tryptophan residues in the sequence, which increases hydrophobicity, and the net charge of the peptide, which decreases hydrophobicity. Peptides containing two or more tryptophans are the most lipophilic, and introduction of arginines in the sequence results in decreasing lipohilicity. Parent is the least lipophilic (Table 11).

TABLE 11

Chromatographic parameters of compstatin peptides in the order of increasing lipophilicity.

| Peptide | Sequence Peptide | | No. of Charges[a] | No. of W | $t_R^b$ (min) | $k^c$ | logk |
|---|---|---|---|---|---|---|---|
| Parent | | ICV VQDWGHHRCT-NH$_2$ | 2+[d], 1-, 2H | 1W | 4.995 ± 0.003 | 2.472 ± 0.006 | ± 0.393 |
| I | Ac- | RCV WQDWGAHRCT-NH$_2$ | 2+, 1-, 2H | 2W | 5.507 ± 0.014 | 2.828 ± 0.012 | ± 0.451 |
| III | Ac- | RCVmeWQDWGAHRCT-NH$_2$ | 2+, 1-, 1H | 1W, 1meW | 10.307 ± 0.023 | 6.165 ± 0.021 | ± 0.790 |
| VI | Ac-RS- | ICVmeWQDWGAHRCT-NH$_2$ | 2+, 1-, 1H | 1W, 1meW | 15.700 ± 0.022 | 9.913 ± 0.026 | ± 0.996 |
| IX | Ac- | ICV WQDWGAHRCT-NH$_2$ | 1+[d], 1-, 1H | 2W | 17.880 ± 10.028 | 11.429 ± 0.031 | ±1.058 |

[a]The number of histidines (marked with H) is included, because they may be positively charged or neutral, depending on their pK$_a$ values.
[b]Retention time.
[c]Retention factor (k).
[d]Includes positive charge of the unblocked backbone of the N-terminus.

The relative lipohilicities of Peptides I, III, VI, IX, and Parent are inversely consistent with solubilities as determined via concentration measurement (absorbance at 280 nm) of saturated peptide solutions, with Peptides I, III, and Parent having approximate aqueous solubilities of >1 mM, Peptide VI>500 µM, and Peptide IX<500 µM.

Molecular Dynamics Simulations.

MD studies, above, have provided insights into the role of arginine at position 1 (Peptide I, Table 7) and the diserine extension at positions 0 and −1 (Peptide IV, Table 7). The MD studies have shown that an Arg1 substitution (Peptide I) maintains the interactions with C3 observed in control Peptide IX, with a new salt bridge being observed between Arg1 and C3 Asp349. As the presence of a methyl group at Trp4 has been reported to enhance binding affinity compared to control Peptide IX, an MD simulations was performed of C3-bound Peptide III, which has a methyl group at Trp4 compared to Peptide I. Similarly, Peptide IV also maintains the interactions with C3 observed in control Peptide IX, with a new hydrogen bond being observed between Ser0 and C3 Asn390. These additional interactions involving N-terminal residues, contribute to increased computed binding affinity with regard to Peptide IX-C3 complex. Critical analysis of the contacts of the diserine extension with C3 residues led us to replace serine by arginine at position −1, and additionally investigate Peptide VI in complex with C3 using MD simulations. Besides increased intermolecular contacts and computed binding affinities, the introduction of the polar-charged arginine residues at positions 1 (Peptide III) or −1 (Peptide VI) also contribute to increased peptide solubilities, a desired property of the new designs.

Figure 16B:
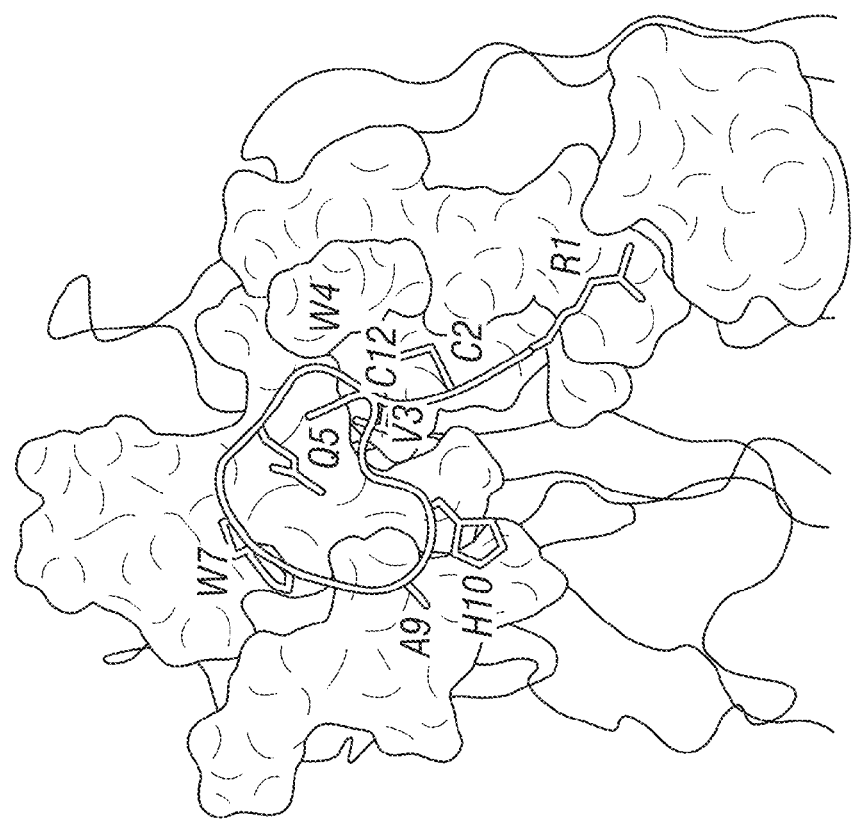
Figure 16A:
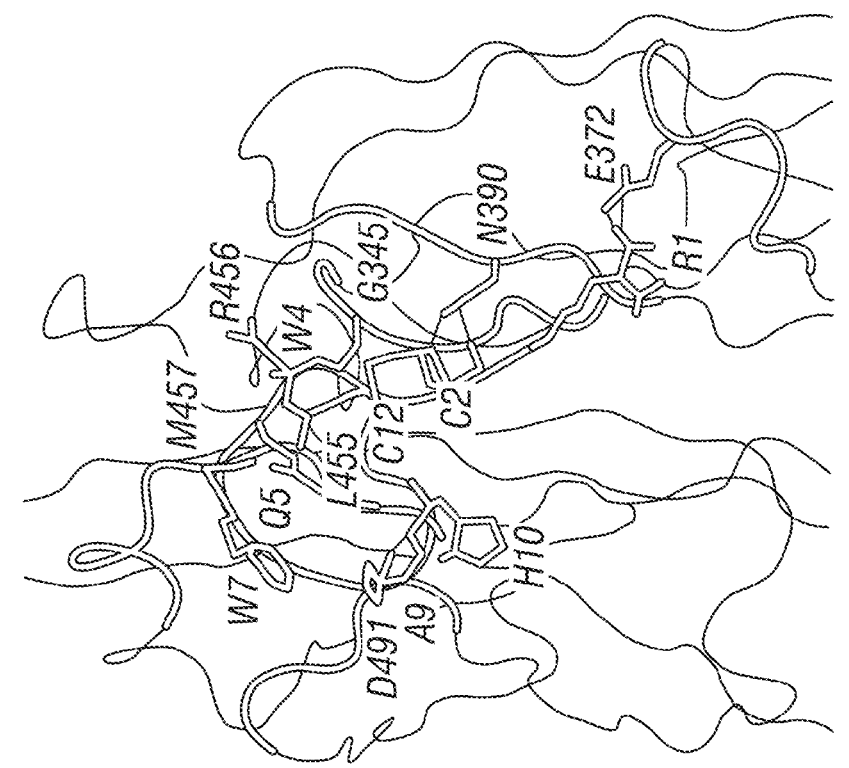
Figure 16F:
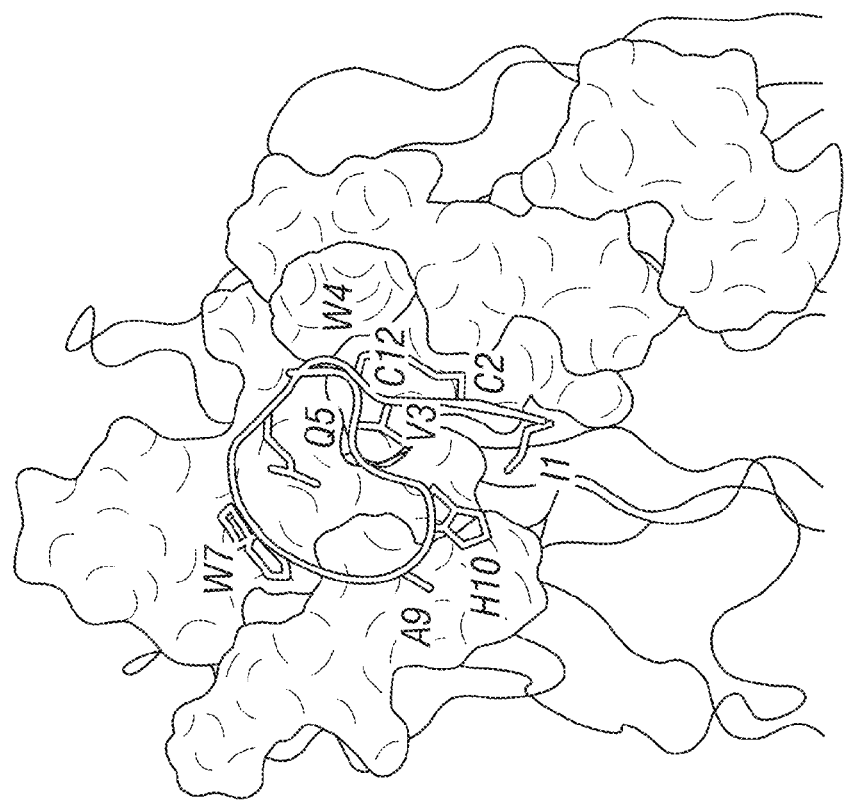
Figure 16E:
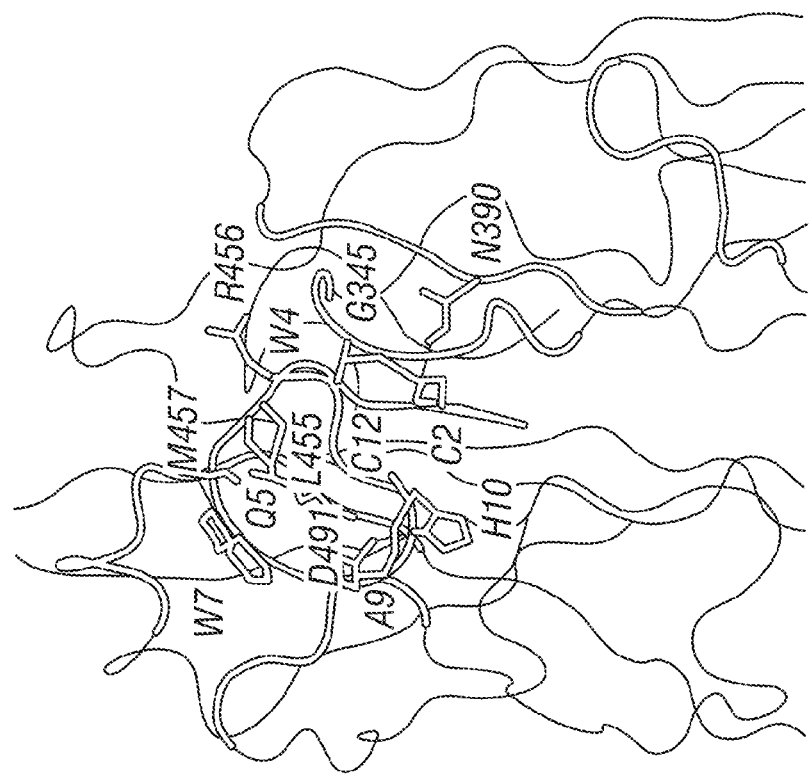
Figure 18:
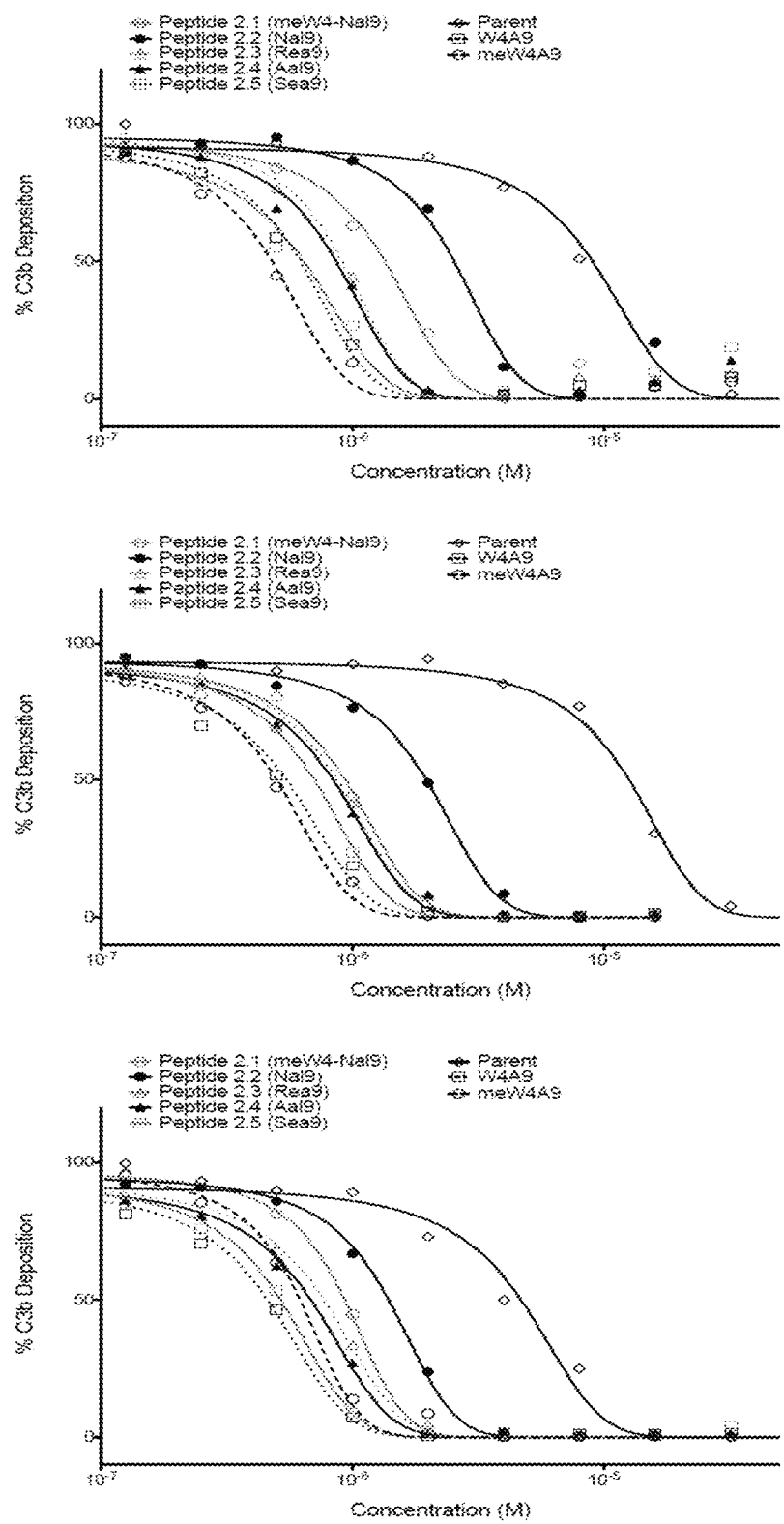
FIG. 18 shows ELISA and hemolytic assay data used to extract the $IC_{50}$ values of peptide of the disclosure. C3b ELISA data, representing the inhibition of cleavage of C3 to C3a and C3b by compstatin peptides, quantified as inhibition of the formation of C3b. C5b-9 ELISA data, representing inhibition of the formation of the C5b-9 terminal complex of complement activation. Hemolytic assay data, representing inhibition of rabbit erythrocyte hemolysis by the C5b-9 terminal complex activation.
Figure 19:
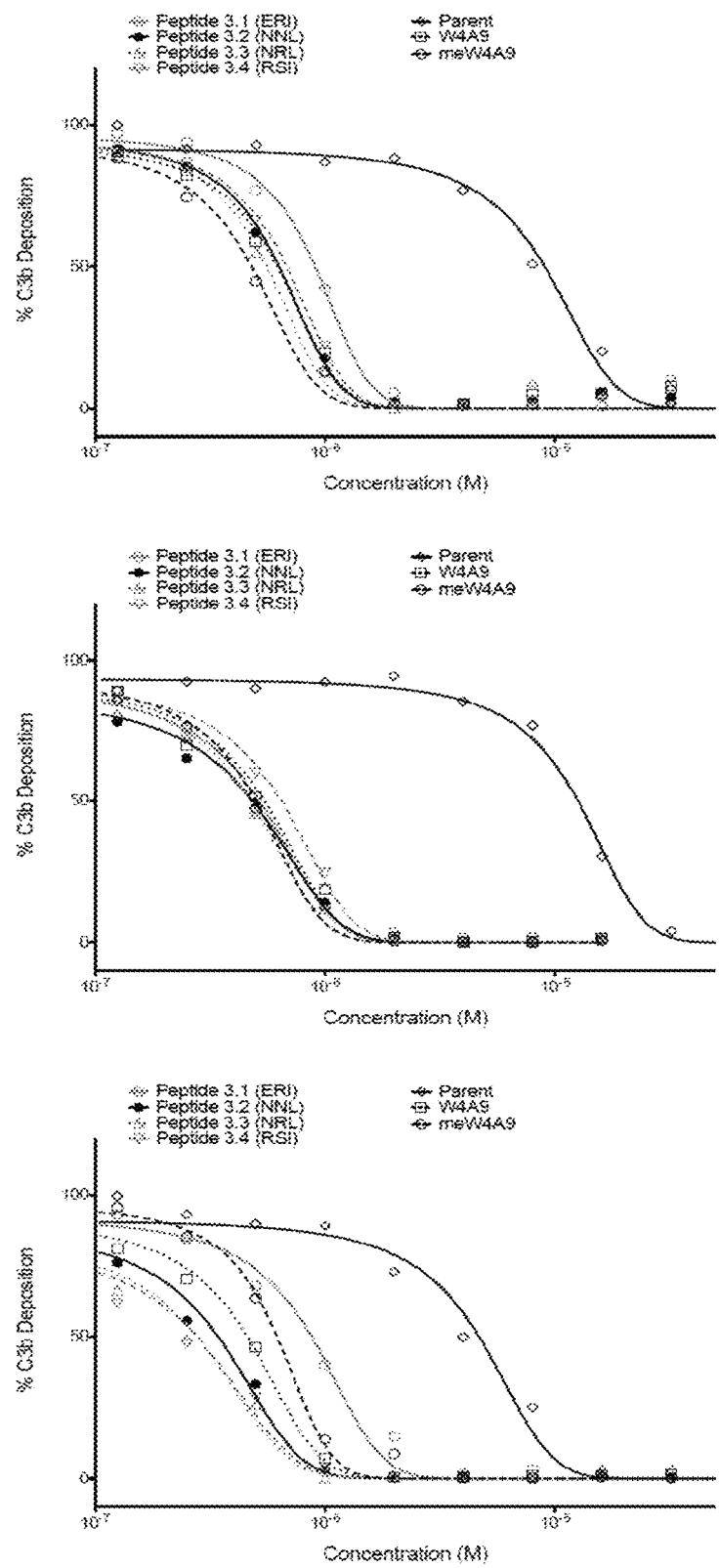
FIG. 19 shows ELISA and hemolytic assay data used to extract the $IC_{50}$ values of peptide of the disclosure. C3b ELISA data, representing the inhibition of cleavage of C3 to C3a and C3b by compstatin peptides, quantified as inhibition of the formation of C3b. C5b-9 ELISA data, representing inhibition of the formation of the C5b-9 terminal complex of complement activation. Hemolytic assay data, representing inhibition of rabbit erythrocyte hemolysis by the C5b-9 terminal complex activation.
Figure 20:
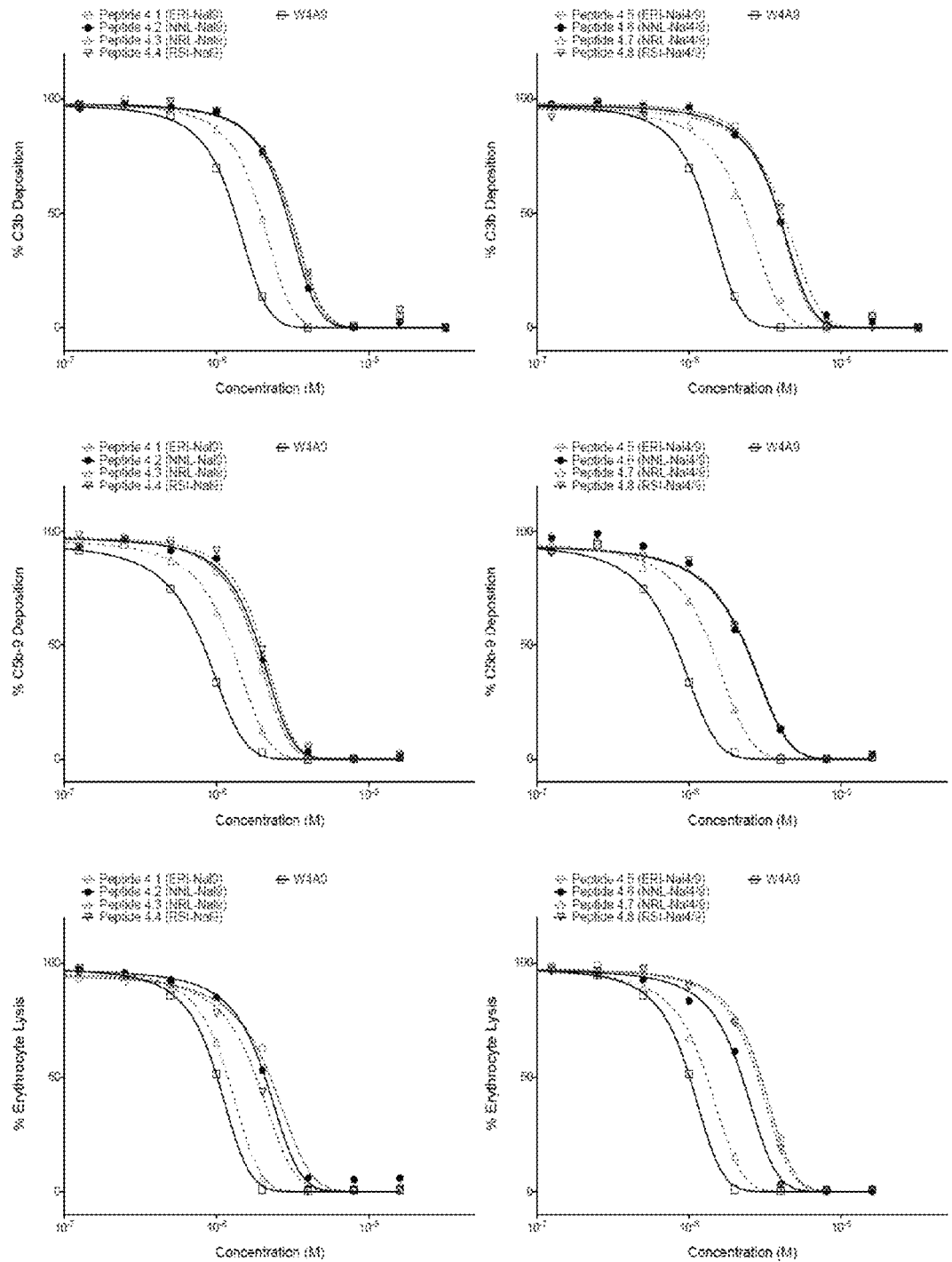
FIG. 20 shows ELISA and hemolytic assay data used to extract the $IC_{50}$ values of peptide of the disclosure. C3b ELISA data, representing the inhibition of cleavage of C3 to C3a and C3b by compstatin peptides, quantified as inhibition of the formation of C3b. C5b-9 ELISA data, representing inhibition of the formation of the C5b-9 terminal complex of complement activation. Hemolytic assay data, representing inhibition of rabbit erythrocyte hemolysis by the C5b-9 terminal complex activation.

MD simulations were performed to understand the molecular interactions of the two most promising new peptides (Peptides III and VI). FIG. 15 shows representative MD structures of Peptides III, VI and control Peptide IX, depicting intermolecular hydrogen bonding patterns and nonpolar pockets within the binding site. Typically, the β-residue compstatin peptides form intermolecular contacts with four C3 sectors, as is the case for control Peptide IX (FIG. 16E, F). For Peptide III, the incorporation of a methyl group at Trp4, in conjunction with an Ile1Arg substitution, leads to additional intramolecular interactions between peptide residues and additional intermolecular peptide-C3 interactions, compared to control Peptide IX. The methyl group of Trp4 fits between the disulfide bridge Cys2-Cys12 of the ligand and residues His392 and Pro393 of C3. Owing to the favorable Cys2-methylated-Trp4 interaction, the N-terminus of the ligand is displaced (FIG. 16A, B, towards segments on the right-hand side of each panel) with regard to Peptide IX (FIG. 16C, D); the root mean square displacement of atom Arg1 Cα is 2.3 Å. Therefore, the side chain of Arg1 of Peptide III is favored to form a new highly interacting salt bridge with Glu372 of the fifth C3 sector (FIG. 16A; Table 12). This finding is in contrast to the Arg1-Asp349 salt bridge, which is present in the absence of methyl group at Trp4 (Peptide I). For Peptide VI, the two-residue Arg-Ser N-terminal extension forms additional contacts with a fifth C3 sector (FIG. 16C, D; Table 12). These contacts include a strong salt bridge between the side chains of Arg-1 and C3 residue Glu372 of the fifth sector, and contribute to increased stability of the complex compared to control Peptide IX. FIG. 17 shows the interaction free energy maps of intermolecular interactions between protein residues and ligand residues. Panels 17A, B present the polar and Panels 17C, D present the nonpolar interaction free energies of Peptides III and VI, respectively. The strongest pairwise intermolecular interactions, are formed between the newly introduced Arg1/Arg-1 residues of Peptides III and IV, respectively, and C3 Glu372 (FIG. 17). Similarly to Peptide III, the Trp4 methyl group of Peptide VI fits between the disulfide bridge residues Cys2-Cys12 of the ligand and residues His392 and Pro393 of C3. It is worth noting that Ile1 of Peptide VI is not destabilized from its initial position as it is attracted to C3 residues Pro347 and Asn390 on the one side, and C3 residues Leu454, Leu492, as well as compstatin residue His10, on the other side.

TABLE 12

Intermolecular hydrogen-bond occupancies for Peptides III and VI in complex with C3, from the analysis of molecular dynamics trajectories. Percent occupancies have been computed from the analysis of 140/200 snapshots (per trajectory), extracted at 50-ps intervals from the five 7/10-ns molecular dynamics trajectories, respectively for Peptides III/VI. A hydrogen bond was present if the donor (D)-acceptor (A) distance was less than 3.5 Å and the corresponding angle (D-H-A) was larger than 90°. "Main" and "Side" refer to main chain and side chain donors/acceptors.

| Intermolecular Atom Pairs | | Hydrogen Bond Occupancy (%) Peptide III | Hydrogen Bond Occupancy (%) Peptide VI |
|---|---|---|---|
| Arg-1 Side-NH1/2 | Asn371 Main-O | — | 21 |
| Arg-1 Side-NH1/2 | Glu372 Side-OE1/2 | — | 100 |
| Arg-1 Side-NE | Glu372 Side-OE1/2 | — | 98 |
| Ser0 Main-O | Asn390 Side-ND2 | — | 77 |
| Ile/Arg1 Side-NH1/2 | Glu372 Side-OE1/2 | 77 | — |
| Ile/Arg1 Side-NE | Glu372 Side-OE1/2 | 33 | — |
| Arg1 Side-NH1/2 | Ser388 Main-O | 37 | — |

TABLE 12-continued

Intermolecular hydrogen-bond occupancies for Peptides III and VI in complex with C3, from the analysis of molecular dynamics trajectories. Percent occupancies have been computed from the analysis of 140/200 snapshots (per trajectory), extracted at 50-ps intervals from the five 7/10-ns molecular dynamics trajectories, respectively for Peptides III/VI. A hydrogen bond was present if the donor (D)-acceptor (A) distance was less than 3.5 Å and the corresponding angle (D-H-A) was larger than 90°. "Main" and "Side" refer to main chain and side chain donors/acceptors.

| Intermolecular Atom Pairs | | Hydrogen Bond Occupancy (%) Peptide III | Hydrogen Bond Occupancy (%) Peptide VI |
|---|---|---|---|
| Cys2 Main-N | Asn390 Side-OD1 | 76 | 91 |
| Cys2 Main-N | Asn390 Side-ND2 | 9 | 12 |
| Cys2 Main-O | Asn390 Side-ND2 | 50 | — |
| Trp4 Main-O | Arg456 Side-NH1/2 | 52 | 52 |
| Trp4 Main-O | Arg456 Side-NE | 97 | 96 |
| Trp4 Main-N | Gly345 Main-O | 100 | 100 |
| Gln5 Side-OE1 | Met457 Main-N | 96 | 95 |
| Gln5 Side-NE2 | Leu455 Main-O | 64 | 57 |
| Asp6 Main-N | Arg459 Side NH1/2 | 4 | 12 |
| Trp7 Side-NE1 | Met457 Main-O | 96 | 99 |
| Ala9 Main-N | Asp491 Side-OD1/2 | 88 | 100 |
| His10 Side-N | Asp491 Side-OD1/2 | 74 | 91 |
| His10 Main-ND1 | Asp491 Side-OD1/2 | 79 | 100 |

The following table 13 provides $IC_{50}$ values for compstatin analogs listed in Table 7.

| Peptide | | Sequence[a] -10123 4 5678 9 0123[c] | | | C3b ELISA IC50 (µM) | C5b-9 ELISA IC50 (µM) | Lysis IC50 (µM) | SEQ ID NO. |
|---|---|---|---|---|---|---|---|---|
| Peptide I | Ac- | RCV | W QDWG | A HRCT-NH2 | 2.6 ± 0.3 | 2.0 ± 0.4 | 3.3 ± 0.4 | 5 |
| Peptide III | Ac- | RCV | {meW}QDWG | A HRCT-NH2 | 1.4 ± 0.3 | 1.1 ± 0.3 | 2.2 ± 0.2 | 7 |
| Peptide VI | Ac-RSICV | {meW}QDWG | A HRCT-NH2 | 1.7 ± 0.3 | 1.1 ± 0.2 | 2.2 ± 0.2 | 10 |
| Parent | | ICV | V QDWG | H HRCT-NH2 | 35.0 ± 4.2 | 18.6 ± 3.5 | 12.9 ± 1.3 | 1 |
| Peptide IX | Ac- | ICV | W QDWG | A HRCT-NH2 | 1.9 ± 0.2 | 1.0 ± 0.3 | 2.6 ± 0.3 | 13 |
| Peptide 2.1 | Ac- | ICV | {meW}QDWG | {Nal}HRCT-NH2 | 1.4 ± 0.3 | 0.9 ± 0.1 | 0.9 ± 0.1 | 14 |
| Peptide 2.2 | Ac- | ICV | W QDWG | {Nal}HRCT-NH2 | 2.4 ± 0.4 | 2.0 ± 0.4 | 1.4 ± 0.1 | 15 |
| Peptide 2.3 | Ac- | ICV | W QDWG | {Rea}HRCT-NH2 | 0.9 ± 0.1 | 0.9 ± 0.1 | 0.8 ± 0.1 | 16 |
| Peptide 2.4 | Ac- | ICV | W QDWG | {Aal}HRCT-NH2 | 0.9 ± 0.1 | 0.8 ± 0.1 | 0.7 ± 0.1 | 17 |
| Peptide 2.5 | Ac- | ICV | W QDWG | {Sea}HRCT-NH2 | 0.6 ± 0.1 | 0.7 ± 0.1 | 0.5 ± 0.1 | 18 |
| Peptide 3.1 | Ac-ERICV | W QDWG | A HRCT-NH2 | 0.9 ± 0.1 | 0.5 ± 0.1 | 0.9 ± 0.2 | 19 |
| Peptide 3.2 | Ac-NNLCV | W QDWG | A HRCT-NH2 | 0.6 ± 0.1 | 0.5 ± 0.1 | 0.3 ± 0.1 | 20 |
| Peptide 3.3 | Ac-NRLCV | W QDWG | A HRCT-NH2 | 0.6 ± 0.1 | 0.5 ± 0.1 | 0.3 ± 0.1 | 21 |
| Peptide 3.4 | Ac-RSICV | W QDWG | A HRCT-NH2 | 0.7 ± 0.1 | 0.6 ± 0.1 | 0.3 ± 0.1 | 22 |
| Peptide I | Ac- | RCV | W QDWG | A HRCT-NH2 | 1.1 ± 0.1 | 1.0 ± 0.1 | 1.2 ± 0.1 | 5 |
| Peptide III | Ac- | RCV | {meW}QDWG | A HRCT-NH2 | 0.5 ± 0.1 | 0.6 ± 0.1 | 0.6 ± 0.1 | 7 |
| Peptide VI | Ac-RSICV | {meW}QDWG | A HRCT-NH2 | 0.6 ± 0.1 | 0.6 ± 0.1 | 0.3 ± 0.1 | 10 |
| Parent | | | V QDWG | H HRCT-NH2 | 6.9 ± 1.0 | 12.6 ± 1.2 | 4.7 ± 0.9 | 1 |
| meW4A9 | Ac- | ICV | {meW}QDWG | A HRCT-NH2 | 0.5 ± 0.1 | 0.5 ± 0.1 | 0.6 ± 0.1 | |
| W4A9 | Ac- | ICV | W QDWG | A HRCT-NH2 | 0.6 ± 0.1 | 0.5 ± 0.1 | 0.5 ± 0.1 | 13 |

-continued

| Peptide | Sequence<br>-10123 | 4 5678 | 9 0123<sup>c</sup> | C3b ELISA IC50 (µM) | C5b-9 ELISA IC50 (µM) | Lysis IC50 (µM) | SEQ ID NO. |
|---|---|---|---|---|---|---|---|
| Linear | ICV | V QDWG | H HRCT-NH2 | Inactive | Inactive | Inactive | |
| Peptide 4.1 | Ac-ERICV | W QDWG | {Nal}HRCT-NH2 | 3.0 ± 0.1 | 1.8 ± 0.1 | 2.3 ± 0.2 | 23 |
| Peptide 4.2 | Ac-NNLCV | W QDWG | {Nal}HRCT-NH2 | 2.9 ± 0.1 | 1.9 ± 0.1 | 2.1 ± 0.2 | 24 |
| Peptide 4.3 | Ac-NRLCV | W QDWG | {Nal}HRCT-NH2 | 2.0 ± 0.1 | 1.2 ± 0.1 | 1.2 ± 0.1 | 25 |
| Peptide 4.4 | Ac-RSICV | W QDWG | {Nal}HRCT-NH2 | 3.1 ± 0.1 | 2.0 ± 0.1 | 1.8 ± 0.1 | 26 |
| Peptide 4.5 | Ac-ERICV | {Nal}QDWG | {Nal}HRCT-NH2 | 3.8 ± 0.2 | 2.4 ± 0.2 | 3.0 ± 0.2 | 27 |
| Peptide 4.6 | Ac-NNLCV | {Nal}QDWG | {Nal}HRCT-NH2 | 3.9 ± 0.2 | 2.3 ± 0.2 | 2.2 ± 0.1 | 28 |
| Peptide 4.7 | Ac-NRLCV | {Nal}QDWG | {Nal}HRCT-NH2 | 2.3 ± 0.2 | 1.4 ± 0.1 | 1.3 ± 0.1 | 29 |
| Peptide 4.8 | Ac-RSICV | {Nal}QDWG | {Nal}HRCT-NH2 | 4.1 ± 0.2 | 2.4 ± 0.2 | 2.8 ± 0.2 | 30 |
| W4A9 | Ac- ICV | W QDWG | A HRCT-NH2 | 1.3 ± 0.1 | 0.8 ± 0.1 | 1.1 ± 0.1 | 13 |
| Linear | ICV | V QDWG | H HRCT-NH2 | Inactive | Inactive | Inactive | |

A number of embodiments have been described herein. Nevertheless, it will be understood that various modifications may be made without departing from the spirit and scope of this disclosure. Accordingly, other embodiments are within the scope of the following claims.

What is claimed is:

1. A compstatin analog comprising the sequence $X_1X_2X_3CVX_4QDWGX_5HRCT$, wherein $X_1$ and $X_2$ may or may not be present, if $X_1$ and/or $X_2$ are present $X_1$ is selected from S, W, R, E or N and $X_2$ is selected from S, W, R or N; wherein $X_3$ is selected from W, meW, R, I or L, wherein $X_4$ is W, meW, Nmw, V, Y or a non-natural amino acid analog of alanine; wherein $X_5$ is A or a non-natural amino acid analog of alanine; wherein the analog is acetylated at the N-terminus and amidated at the C-terminus; and wherein the compstatin analog is capable of binding mouse, rat or human C3.

2. A compstatin analog of claim 1, wherein $X_1$ and $X_2$ comprise a diserine extension.

3. The compstatin analog of claim 1, wherein the compound is capable of binding rat or mouse C3.

4. The compstatin analog of claim 1, wherein $X_3$ is R, and $X_4$ is W.

5. The compstatin analog of claim 4, wherein the compound is capable of binding rat or mouse C3.

6. The compstatin analog of claim 1, wherein the analog comprises a sequence selected from the group consisting of (a) Ac-meWCVWQDWGAHRCT-NH$_2$ (SEQ ID NO:6), (b) Ac-RCVmeWQDWGAHRCT-NH$_2$ (SEQ ID NO:7), (c) Ac-WWRCVWQDWGAHRCT-NH$_2$ (SEQ ID NO:9), (d) Ac-RSICVmeWQDWGAHRCT-NH$_2$ (SEQ ID NO:10), (e) Ac-RSRCVmeWQDWGAHRCT-NH$_2$ (SEQ ID NO:11), (f) Ac-SSRCVmeWQDWGAHRCT-NH$_2$ (SEQ ID NO:12), (g) Ac-ICVmeWQDWG(Nal)HRCT-NH$_2$ (SEQ ID NO:14); (h) Ac-ICVWQDWG(Nal)HRCT-NH$_2$ (SEQ ID NO:15), (i) Ac-ICVWQDWG(Rea)HRCT-NH$_2$ (SEQ ID NO:16); (j) Ac-ICVWQDWG(Aal)HRCT-NH$_2$ (SEQ ID NO:17); (k) Ac-ICVWQDWG(Sea)HRCT-NH$_2$ (SEQ ID NO:18); (l) Ac-ERICVWQDWGAHRCT-NH$_2$ (SEQ ID NO:19), (m) Ac-NNLCVWQDWGAHRCT-NH$_2$ (SEQ ID NO:20); (n) Ac-NRLCVWQDWGAHRCT-NH$_2$ (SEQ ID NO:21); (o) Ac-RSICVWQDWGAHRCT-NH$_2$ (SEQ ID NO:22); (p) Ac-ERICVWQDWG(Nal)HRCT-NH$_2$ (SEQ ID NO:23); (q) Ac-NNLCVWQDWG(Nal)HRCT-NH$_2$ (SEQ ID NO:24); (r) Ac-NRLCVWQDWG(Nal)HRCT-NH$_2$ (SEQ ID NO:25); (s) Ac-RSICVWQDWG(Nal)HRCT-NH$_2$ (SEQ ID NO:26); (t) Ac-ERICV(Nal)QDWG(Nal)HRCT-NH$_2$ (SEQ ID NO:27); (u) Ac-NNLCV(Nal)QDWG(Nal)HRCT-NH$_2$ (SEQ ID NO:28); (v) Ac-NRLCV(Nal)QDWG(Nal)HRCT-NH$_2$ (SEQ ID NO:29); and (w) Ac-RSICV(Nal)QDWG(Nal)HRCT-NH$_2$ (SEQ ID NO:30).

7. The compstatin analog of claim 1, wherein the peptide is cyclized through a disulfide bond between the cysteine residues.

8. A method of using a compstatin analog of claim 1 for treating age-related macular degeneration or other complement system-mediated diseases, comprising contacting an individual in need of treatment with the compstatin analog to inhibit the activation of human or primate C3.

9. The method of claim 8, wherein the disease is selected from a group consisting of asthma, adult respiratory distress syndrome, hemolytic anemia, rheumatoid arthritis, rejection of xenotransplantation, stroke and heart attack.

10. The method of claim 8, wherein the compstatin analog inhibits the classical complement pathway.

11. The method of claim 8, wherein the compstatin analog inhibits the alternative complement pathway.

12. The method of claim 8, wherein the compstatin analog inhibits both the classical and alternate pathways.

13. The method of claim 8, wherein the composition is administered intravenously.

14. The method of claim 9, wherein the composition is administered intravitreally.

15. A composition comprising a compstatin analog of claim 1 and a pharmaceutically acceptable carrier.

* * * * *

SEQUENCE LISTING

<160> NUMBER OF SEQ ID NOS: 55

<210> SEQ ID NO 1
<211> LENGTH: 13
<212> TYPE: PRT
<213> ORGANISM: Homo sapiens

<400> SEQUENCE: 1

Ile Cys Val Val Gln Asp Trp Gly His His Arg Cys Thr
1               5                   10

<210> SEQ ID NO 2
<211> LENGTH: 206
<212> TYPE: PRT
<213> ORGANISM: Homo sapiens

<400> SEQUENCE: 2

Ser Pro Tyr Gln Ile His Phe Thr Lys Thr Pro Lys Tyr Phe Lys Pro
1               5                   10                  15

Gly Met Pro Phe Asp Leu Met Val Phe Val Thr Asn Pro Asp Gly Ser
            20                  25                  30

Pro Ala Tyr Arg Val Pro Val Ala Val Gln Gly Glu Asp Thr Val Gln
        35                  40                  45

Ser Leu Thr Gln Gly Asp Gly Val Ala Lys Leu Ser Ile Asn Thr His
    50                  55                  60

Pro Ser Gln Lys Pro Leu Ser Ile Thr Val Arg Thr Lys Lys Gln Glu
65                  70                  75                  80

Leu Ser Glu Ala Glu Gln Ala Thr Arg Thr Met Gln Ala Leu Pro Tyr
                85                  90                  95

Ser Thr Val Gly Asn Ser Asn Asn Tyr Leu His Leu Ser Val Leu Arg
            100                 105                 110

Thr Glu Leu Arg Pro Gly Glu Thr Leu Asn Val Asn Phe Leu Leu Arg
            115                 120                 125

Met Asp Arg Ala His Glu Ala Lys Ile Arg Tyr Tyr Thr Tyr Leu Ile
130                 135                 140

Met Asn Lys Gly Arg Leu Leu Lys Ala Gly Arg Gln Val Arg Glu Pro
145                 150                 155                 160

Gly Gln Asp Leu Val Val Leu Pro Leu Ser Ile Thr Thr Asp Phe Ile
            165                 170                 175

Pro Ser Phe Arg Leu Val Ala Tyr Tyr Thr Leu Ile Gly Ala Ser Gly
            180                 185                 190

Gln Arg Glu Val Val Ala Asp Ser Val Trp Val Asp Val Lys
            195                 200                 205

<210> SEQ ID NO 3
<211> LENGTH: 205
<212> TYPE: PRT
<213> ORGANISM: Rattus norvegicus

<400> SEQUENCE: 3

Ser Pro Tyr Gln Ile His Phe Thr Lys Thr Pro Lys Phe Phe Lys Pro
1               5                   10                  15

Ala Met Pro Phe Asp Leu Met Val Phe Val Thr Asn Pro Asp Gly Ser
            20                  25                  30

Pro Ala Arg Arg Val Pro Val Thr Gln Gly Ser Asp Ala Gln Ala
            35                  40                  45

Leu Thr Gln Asp Asp Gly Val Ala Lys Leu Ser Val Asn Thr Pro Asn
50                  55                  60

Asn Arg Gln Pro Leu Thr Ile Thr Val Ser Thr Lys Lys Glu Gly Ile
65                  70                  75                  80

Pro Asp Ala Arg Gln Ala Thr Arg Thr Met Gln Ala Gln Pro Tyr Ser
            85                  90                  95

Thr Met His Asn Ser Asn Asn Tyr Leu His Leu Ser Val Ser Arg Val
            100                 105                 110

Glu Leu Lys Pro Gly Asp Asn Leu Asn Val Asn Phe His Leu Arg Thr
            115                 120                 125

Asp Ala Gly Gln Glu Ala Lys Ile Arg Tyr Tyr Thr Tyr Leu Val Met
130                 135                 140

Asn Lys Gly Lys Leu Leu Lys Ala Gly Arg Gln Val Arg Glu Pro Gly
145                 150                 155                 160

Gln Asp Leu Val Val Leu Ser Leu Pro Ile Thr Pro Glu Phe Ile Pro
            165                 170                 175

Ser Phe Arg Leu Val Ala Tyr Tyr Thr Leu Ile Gly Ala Asn Gly Gln
            180                 185                 190

Arg Glu Val Val Ala Asp Ser Val Trp Val Asp Val Lys
            195                 200                 205

<210> SEQ ID NO 4
<211> LENGTH: 205
<212> TYPE: PRT
<213> ORGANISM: Mus musculus

<400> SEQUENCE: 4

Ser Pro Tyr Gln Ile His Phe Thr Lys Thr Pro Lys Phe Phe Lys Pro
1               5                   10                  15

Ala Met Pro Phe Asp Leu Met Val Phe Val Thr Asn Pro Asp Gly Ser
            20                  25                  30

Pro Ala Ser Lys Val Leu Val Thr Gln Gly Ser Asn Ala Lys Ala
            35                  40                  45

Leu Thr Gln Asp Asp Gly Val Ala Lys Leu Ser Ile Asn Thr Pro Asn
 50                  55                  60

Ser Arg Gln Pro Leu Thr Ile Thr Val Arg Thr Lys Lys Asp Thr Leu
 65                  70                  75                  80

Pro Glu Ser Arg Gln Ala Thr Lys Thr Met Glu Ala His Pro Tyr Ser
                 85                  90                  95

Thr Met His Asn Ser Asn Asn Tyr Leu His Leu Ser Val Ser Arg Met
                100                 105                 110

Glu Leu Lys Pro Gly Asp Asn Leu Asn Val Asn Phe His Leu Arg Thr
            115                 120                 125

Asp Pro Gly His Glu Ala Lys Ile Arg Tyr Tyr Thr Tyr Leu Val Met
        130                 135                 140

Asn Lys Gly Lys Leu Leu Lys Ala Gly Arg Gln Val Arg Glu Pro Gly
145                 150                 155                 160

Gln Asp Leu Val Val Leu Ser Leu Pro Ile Thr Pro Glu Phe Ile Pro
                165                 170                 175

Ser Phe Arg Leu Val Ala Tyr Tyr Thr Leu Ile Gly Ala Ser Gly Gln
                180                 185                 190

Arg Glu Val Val Ala Asp Ser Val Trp Val Asp Val Lys
            195                 200                 205

<210> SEQ ID NO 5
<211> LENGTH: 13
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (13)..(13)
<223> OTHER INFORMATION: C-terminally amidated

<400> SEQUENCE: 5

Arg Cys Val Trp Gln Asp Trp Gly Ala His Arg Cys Thr
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: Xaa is a methylated Tryptophan and N-terminally
      acetylated
<220> FEATURE:
<221> NAME/KEY: MISC_FEATURE
<222> LOCATION: (13)..(13)
<223> OTHER INFORMATION: C-terminally amidated

<400> SEQUENCE: 6

Xaa Cys Val Trp Gln Asp Trp Gly Ala His Arg Cys Thr
 1               5                  10

<210> SEQ ID NO 7
<211> LENGTH: 13

```
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (4)..(4)
<223> OTHER INFORMATION: Xaa is methylated Tryptophan
<220> FEATURE:
<221> NAME/KEY: MISC_FEATURE
<222> LOCATION: (13)..(13)
<223> OTHER INFORMATION: C-terminally amidated

<400> SEQUENCE: 7

Arg Cys Val Xaa Gln Asp Trp Gly Ala His Arg Cys Thr
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 8

Ser Ser Ile Cys Val Trp Gln Asp Trp Gly Ala His Arg Cys Thr
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 9

Trp Trp Arg Cys Val Trp Gln Asp Trp Gly Ala His Arg Cys Thr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is methylated tryptophan
```

```
<220> FEATURE:
<221> NAME/KEY: MISC_FEATURE
<222> LOCATION: (15)..(15)
<223> OTHER INFORMATION: C-terminally amidated

<400> SEQUENCE: 10

Arg Ser Ile Cys Val Xaa Gln Asp Trp Gly Ala His Arg Cys Thr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is methylated tryptophan
<220> FEATURE:
<221> NAME/KEY: MISC_FEATURE
<222> LOCATION: (15)..(15)
<223> OTHER INFORMATION: C-terminally amidated

<400> SEQUENCE: 11

Arg Ser Arg Cys Val Xaa Gln Asp Trp Gly Ala His Arg Cys Thr
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is methylated tryptophan
<220> FEATURE:
<221> NAME/KEY: MISC_FEATURE
<222> LOCATION: (15)..(15)
<223> OTHER INFORMATION: C-terminally amidated

<400> SEQUENCE: 12

Ser Ser Arg Cys Val Xaa Gln Asp Trp Gly Ala His Arg Cys Thr
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (13)..(13)
<223> OTHER INFORMATION: C-terminallyl amidated

<400> SEQUENCE: 13

Ile Cys Val Trp Gln Asp Trp Gly Ala His Arg Cys Thr
```

<210> SEQ ID NO 14
<211> LENGTH: 13
<212> TYPE: PRT
<213> ORGANISM: Artificial Sequence
<220> FEATURE:
<223> OTHER INFORMATION: Sythesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (4)..(4)
<223> OTHER INFORMATION: Xaa is methylated tryptophan
<220> FEATURE:
<221> NAME/KEY: MISC_FEATURE
<222> LOCATION: (9)..(9)
<223> OTHER INFORMATION: Xaa is 1-napththylalanine or 2-naphthylalanine
<220> FEATURE:
<221> NAME/KEY: MISC_FEATURE
<222> LOCATION: (13)..(13)
<223> OTHER INFORMATION: C-terminally amidated

<400> SEQUENCE: 14

Ile Cys Val Xaa Gln Asp Trp Gly Xaa His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (9)..(9)
<223> OTHER INFORMATION: Xaa is 1-naphthylalanine or 2-naphthylalanine
<220> FEATURE:
<221> NAME/KEY: MISC_FEATURE
<222> LOCATION: (13)..(13)
<223> OTHER INFORMATION: C-terminally amidated

<400> SEQUENCE: 15

Ile Cys Val Trp Gln Asp Trp Gly Xaa His Arg Cys Thr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (9)..(9)
<223> OTHER INFORMATION: Xaa is an unnatural Sea amino acid
<220> FEATURE:
<221> NAME/KEY: MISC_FEATURE
<222> LOCATION: (13)..(13)
<223> OTHER INFORMATION: C-terminally amidated

<400> SEQUENCE: 16

Ile Cys Val Trp Gln Asp Trp Gly Xaa His Arg Cys Thr Asn His

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (9)..(9)
<223> OTHER INFORMATION: Xaa is an unnatural Aal amino acid
<220> FEATURE:
<221> NAME/KEY: MISC_FEATURE
<222> LOCATION: (13)..(13)
<223> OTHER INFORMATION: C-terminally amidated

<400> SEQUENCE: 17

Ile Cys Val Trp Gln Asp Trp Gly Xaa His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (9)..(9)
<223> OTHER INFORMATION: Xaa is an unnatural Sea amino acid
<220> FEATURE:
<221> NAME/KEY: MISC_FEATURE
<222> LOCATION: (13)..(13)
<223> OTHER INFORMATION: C-terminally amidated

<400> SEQUENCE: 18

Ile Cys Val Trp Gln Asp Trp Gly Xaa His Arg Cys Thr
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 19

Glu Arg Ile Cys Val Trp Gln Asp Trp Gly Ala His Arg Cys Thr
1               5                   10                  15

<210> SEQ ID NO 20
<211> LENGTH: 15
<212> TYPE: PRT
<213> ORGANISM: Artificial Sequence
<220> FEATURE:

```
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 20

Asn Asn Leu Cys Val Trp Gln Asp Trp Gly Ala His Arg Cys Thr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 21

Asn Arg Leu Cys Val Trp Gln Asp Trp Gly Ala His Arg Cys Thr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 22

Arg Ser Ile Cys Val Trp Gln Asp Trp Gly Ala His Arg Cys Thr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (11)..(11)
<223> OTHER INFORMATION: Xaa is Xaa is 1-naphthylalanine or
      2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 23
```

```
Glu Arg Ile Cys Val Trp Gln Asp Trp Gly Xaa His Arg Cys Thr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 24

Asn Asn Leu Cys Val Trp Gln Asp Trp Gly Xaa His Arg Cys Thr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 25

Asn Arg Leu Cys Val Trp Gln Asp Trp Gly Xaa His Arg Cys Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 26

Arg Ser Ile Cys Val Trp Gln Asp Trp Gly Xaa His Arg Cys Thr
1               5                   10                  15
```

```
<210> SEQ ID NO 27
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 27

Glu Arg Ile Cys Val Xaa Gln Asp Trp Gly Xaa His Arg Cys Thr
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 28

Asn Asn Leu Cys Val Xaa Gln Asp Trp Gly Xaa His Arg Cys Thr
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
```

<222> LOCATION: (15)..(15)
<223> OTHER INFORMATION: C-terminally amidated

<400> SEQUENCE: 29

Asn Arg Leu Cys Val Xaa Gln Asp Trp Gly Xaa His Arg Cys Thr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (11)..(11)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 30

Arg Ser Ile Cys Val Xaa Gln Asp Trp Gly Xaa His Arg Cys Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 31

Ser Ser Ile Cys Val Xaa Gln Asp Trp Gly Ala His Arg Cys Thr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE

```
<222> LOCATION: (15)..(15)
<223> OTHER INFORMATION: C-terminally amidated

<400> SEQUENCE: 32

Arg Ser Ile Cys Val Xaa Gln Asp Trp Gly Ala His Arg Cys Thr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 33

Arg Ser Arg Cys Val Xaa Gln Asp Trp Gly Ala His Arg Cys Thr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 34

Ser Ser Arg Cys Val Xaa Gln Asp Trp Gly Ala His Arg Cys Thr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 35
```

```
Glu Arg Ile Cys Val Xaa Gln Asp Trp Gly Ala His Arg Cys Thr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 36

Asn Asn Leu Cys Val Xaa Gln Asp Trp Gly Ala His Arg Cys Thr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Sythesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 37

Asn Arg Leu Cys Val Xaa Gln Asp Trp Gly Ala His Arg Cys Thr
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 38

Asp Asn Phe Cys Val Xaa Gln Asp Trp Gly Ala His Arg Cys Thr
1               5                   10                  15
```

<210> SEQ ID NO 39
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 39

Asn Gln Asp Cys Val Xaa Gln Asp Trp Gly Ala His Arg Cys Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 40

Asn Arg Asp Cys Val Xaa Gln Asp Trp Gly Ala His Arg Cys Thr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 41

Glu Arg Trp Cys Val Xaa Gln Asp Trp Gly Ala His Arg Cys Thr
1               5                   10                  15

<210> SEQ ID NO 42
<211> LENGTH: 15
<212> TYPE: PRT

```
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (6)..(6)
<223> OTHER INFORMATION: Xaa is 1-naphthylalanine or 2-naphthylalanine
<220> FEATURE:
<221> NAME/KEY: MISC_FEATURE
<222> LOCATION: (15)..(15)
<223> OTHER INFORMATION: C-terminally amidated

<400> SEQUENCE: 42

Asn Asn Asn Cys Val Xaa Gln Asp Trp Gly Ala His Arg Cys Thr
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 43

Ser Ser Ile Cys Val Tyr Gln Asp Trp Gly Ala His Arg Cys Thr
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 44

Arg Ser Ile Cys Val Tyr Gln Asp Trp Gly Ala His Arg Cys Thr
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated
```

```
<400> SEQUENCE: 45

Arg Ser Arg Cys Val Tyr Gln Asp Trp Gly Ala His Arg Cys Thr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 46

Ser Ser Arg Cys Val Tyr Gln Asp Trp Gly Ala His Arg Cys Thr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 47

Glu Arg Ile Cys Val Tyr Gln Asp Trp Gly Ala His Arg Cys Thr
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 48

Asn Asn Leu Cys Val Tyr Gln Asp Trp Gly Ala His Arg Cys Thr
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
```

```
<220> FEATURE:
<221> NAME/KEY: MISC_FEATURE
<222> LOCATION: (15)..(15)
<223> OTHER INFORMATION: C-terminally amidated

<400> SEQUENCE: 49

Asn Arg Leu Cys Val Tyr Gln Asp Trp Gly Ala His Arg Cys Thr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 50

Asp Asn Phe Cys Val Tyr Gln Asp Trp Gly Ala His Arg Cys Thr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 51

Asn Gln Asp Cys Val Tyr Gln Asp Trp Gly Ala His Arg Cys Thr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 52

Asn Arg Asp Cys Val Tyr Gln Asp Trp Gly Ala His Arg Cys Thr
1               5                   10                  15

<210> SEQ ID NO 53
<211> LENGTH: 15
<212> TYPE: PRT
<213> ORGANISM: Artificial Sequence
<220> FEATURE:
```

```
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 53

Glu Arg Trp Cys Val Tyr Gln Asp Trp Gly Ala His Arg Cys Thr
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: N-terminally acetylated
<220> FEATURE:
<221> NAME/KEY: MISC_FEATURE
<222> LOCATION: (15)..(15)
<223> OTHER INFORMATION: C-terminally amidated

<400> SEQUENCE: 54

Asn Asn Asn Cys Val Tyr Gln Asp Trp Gly Ala His Arg Cys Thr
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Consensus peptide sequence
<220> FEATURE:
<221> NAME/KEY: MISC_FEATURE
<222> LOCATION: (1)..(2)
<223> OTHER INFORMATION: Xaa at positions 1 and 2  may or may not be
      present, if Xaa at position 1 and/or Xaa at positions 2 are
      present each are independently (a) any amino acid, (b) a polar
      amino acid (K, R, H, D, E, C, Y, N, Q, S, T, W, A, G) or (c) S,
      W, meW, R, E or N
<220> FEATURE:
<221> NAME/KEY: MISC_FEATURE
<222> LOCATION: (3)..(3)
<223> OTHER INFORMATION: Xaa is W, meW, R, I or L
<220> FEATURE:
<221> NAME/KEY: MISC_FEATURE
<222> LOCATION: (6)..(6)
<223> OTHER INFORMATION: Xaa is W or meW
<220> FEATURE:
<221> NAME/KEY: MISC_FEATURE
<222> LOCATION: (11)..(11)
<223> OTHER INFORMATION: Xaa is 1-naphthylalanine or 2-naphthylalanine,
      Rea or Sea

<400> SEQUENCE: 55

Xaa Xaa Xaa Cys Val Xaa Gln Asp Trp Gly Xaa His Arg Cys Thr
1               5                   10                  15
```